United States Patent
Andersen et al.

(10) Patent No.: US 7,153,658 B2
(45) Date of Patent: Dec. 26, 2006

(54) METHODS AND COMPOSITIONS FOR DETECTING TARGETS

(75) Inventors: Mark R. Andersen, San Mateo, CA (US); Michael W. Hunkapiller, San Carlos, CA (US); Kenneth J. Livak, San Jose, CA (US); Eugene G. Spier, Palo Alto, CA (US); H. Michael Wenz, Redwood City, CA (US)

(73) Assignee: Applera Corporation, Foster City, CA (US)

( * ) Notice: Subject to any disclaimer, the term of this patent is extended or adjusted under 35 U.S.C. 154(b) by 241 days.

(21) Appl. No.: 10/665,671

(22) Filed: Sep. 19, 2003

(65) Prior Publication Data

US 2004/0121371 A1 Jun. 24, 2004

Related U.S. Application Data

(60) Provisional application No. 60/412,225, filed on Sep. 19, 2002.

(51) Int. Cl.
  *C12Q 1/68* (2006.01)
  *C07H 21/02* (2006.01)
  *C07H 21/04* (2006.01)

(52) U.S. Cl. .................... 435/6; 536/23.1; 536/24.3
(58) Field of Classification Search ................ 435/6; 536/23.1, 24.3
See application file for complete search history.

(56) References Cited

U.S. PATENT DOCUMENTS

| | | | |
|---|---|---|---|
| 5,824,469 A | 10/1998 | Horwitz et al. | |
| 5,952,202 A | 9/1999 | Aoyagi et al. | |
| 5,989,871 A | 11/1999 | Grossman et al. | |
| 5,994,058 A | 11/1999 | Senapathy | |
| 6,027,889 A * | 2/2000 | Barany et al. | 435/6 |
| 6,084,102 A | 7/2000 | Kutyavin et al. | |
| 6,130,073 A | 10/2000 | Edderding | |
| 6,270,967 B1 | 8/2001 | Whitcombe et al. | |
| 6,312,892 B1 | 11/2001 | Barany et al. | |
| 6,331,393 B1 | 12/2001 | Laird et al. | |
| 6,350,580 B1 | 2/2002 | Sorge | |
| 6,387,621 B1 * | 5/2002 | Wittwer | 435/6 |
| 6,528,254 B1 * | 3/2003 | Sorge | 435/6 |
| 6,955,901 B1 * | 10/2005 | Schouten | 435/91.1 |
| 2004/0110134 A1 | 6/2004 | Wenz et al. | |
| 2004/0214196 A1 | 10/2004 | Aydin | |
| 2004/0235005 A1 | 11/2004 | Friedlander et al. | |
| 2005/0272071 A1 | 12/2005 | Lao et al. | |

FOREIGN PATENT DOCUMENTS

| | | |
|---|---|---|
| EP | 1 130 113 A | 9/2001 |
| WO | WO 96/15271 A | 5/1996 |
| WO | WO 01/06012 A | 1/2001 |
| WO | WO 01/57269 A | 8/2001 |
| WO | WO 01/92579 A | 12/2001 |
| WO | WO 2005/026389 A | 3/2005 |

OTHER PUBLICATIONS

Holland et al., PNAS 88 : 7276-7280 (1991).*
Vogelstein et al., PNAS 96 : 9236-9241 (1999).*
Kutyavin et al., Nucleic Acids Research 28(2) : 655-661 (2000).*
Chen et al. Vox Sanguinis 72 (3) : 192-196 (1997).*
U.S. Appl. No. 09/584,905, filed Mar. 30, 2000.
International Search Report dated Mar. 28, 2005 issued in International Appl. No. PCT/US03/29867, 9 pages.
Supplementary European Search Report dated Nov. 14, 2005, issued in European Appl. No. 03759406.6, 5 pages.

\* cited by examiner

*Primary Examiner*—Ethan Whisenant
(74) *Attorney, Agent, or Firm*—Scott R. Bortner; Andrew K. Finn

(57) ABSTRACT

The present invention relates to methods and kits for detecting the presence or absence of (or quantitating) target nucleic acid sequences using ligation and amplification. The invention also relates to methods, reagents, and kits that employ addressable portions and labeled probes.

26 Claims, 23 Drawing Sheets

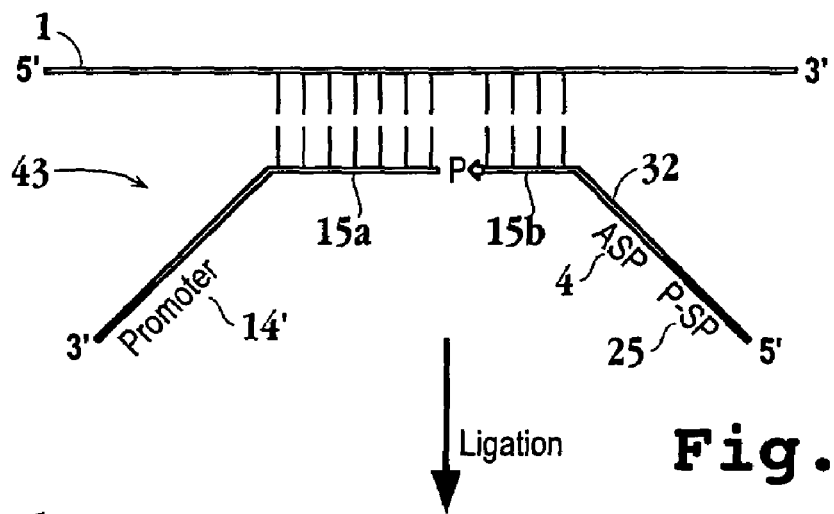
Fig. 5A
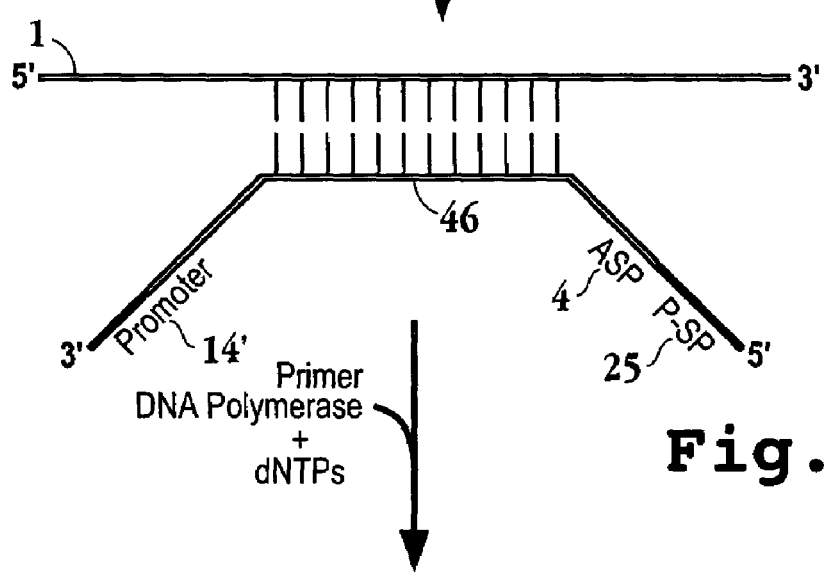
Fig. 5B
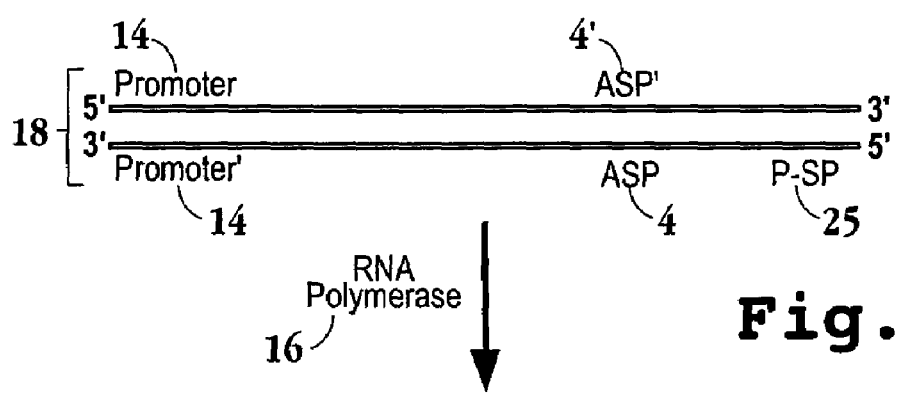
Fig. 5C
Transcription products to which labeled probes hybridize ~17
Fig. 5D

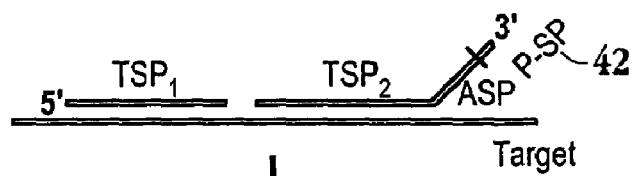
Fig. 14A
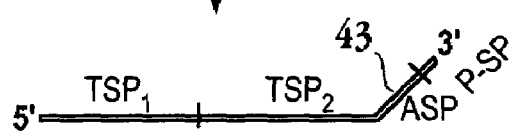
Fig. 14B
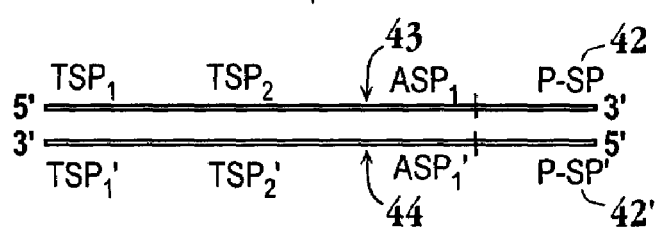
Fig. 14C
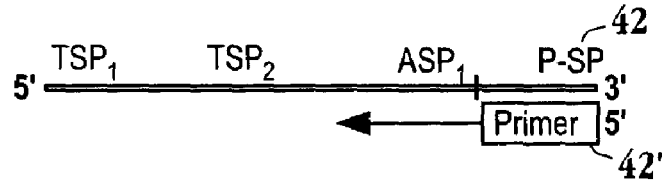
Fig. 14D
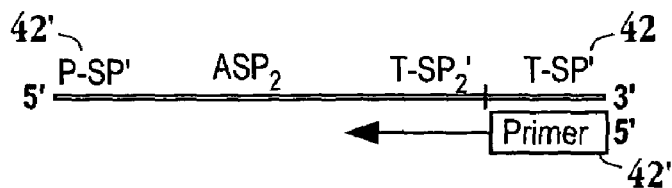

Target with "C" at pivotal nucleotide allows FEN cleavage and ligation of Probes A and Z Target with "C" at pivotal nucleotide allows FEN cleavage and ligation of Probes A and Z Target with "C" at pivotal nucleotide allows FEN cleavage and ligation of Probes Z and A

SEQUENCE LISTING

<160> NUMBER OF SEQ ID NOS: 25

<210> SEQ ID NO 1
<211> LENGTH: 49
<212> TYPE: DNA
<213> ORGANISM: Homo sapiens

<400> SEQUENCE: 1
ttgcctgctc gacttagatc aaaggagacg cggctgcttt cagcctcat            49

<210> SEQ ID NO 2
<211> LENGTH: 49
<212> TYPE: DNA
<213> ORGANISM: Homo sapiens

<400> SEQUENCE: 2
ttgcctgctc gacttagagg gtcacagtag gtggtgcttt cagcctcac            49

<210> SEQ ID NO 3
<211> LENGTH: 33
<212> TYPE: DNA
<213> ORGANISM: Homo sapiens

<400> SEQUENCE: 3
ggggatagtg gctgcatcac tggatagcga cgt                             33

<210> SEQ ID NO 4
<211> LENGTH: 49
<212> TYPE: DNA
<213> ORGANISM: Homo sapiens

<400> SEQUENCE: 4
ttgcctgctc gacttagatc aaaggagacg cggcagtggt tttccaacg            49

<210> SEQ ID NO 5
<211> LENGTH: 51
<212> TYPE: DNA
<213> ORGANISM: Homo sapiens

<400> SEQUENCE: 5
ttgcctgctc gacttagagg gtcacagtag gtggacagtg gttttccaac a         51

<210> SEQ ID NO 6
<211> LENGTH: 32
<212> TYPE: DNA
<213> ORGANISM: Homo sapiens

```
-continued

<400> SEQUENCE: 6
tgaacacacc gggtatcact ggatagcgac gt                                    32

<210> SEQ ID NO 7
<211> LENGTH: 18
<212> TYPE: DNA
<213> ORGANISM: Homo sapiens

<400> SEQUENCE: 7
ttgcctgctc gacttaga                                                    18

<210> SEQ ID NO 8
<211> LENGTH: 18
<212> TYPE: DNA
<213> ORGANISM: Homo sapiens

<400> SEQUENCE: 8
acgtcgctat ccagtgat                                                    18

<210> SEQ ID NO 9
<211> LENGTH: 15
<212> TYPE: DNA
<213> ORGANISM: Homo sapiens

<400> SEQUENCE: 9
ccgcgtctcc tttga                                                       15

<210> SEQ ID NO 10
<211> LENGTH: 16
<212> TYPE: DNA
<213> ORGANISM: Homo sapiens

<400> SEQUENCE: 10
ccacctactg tgaccc                                                      16

<210> SEQ ID NO 11
<211> LENGTH: 70
<212> TYPE: DNA
<213> ORGANISM: Homo sapiens

<400> SEQUENCE: 11
ttgcctgctc gacttagatc cgcgtctcct ttgatttgta ccactctttt tcggtcaaaa      60
acgagatcaa                                                             70

<210> SEQ ID NO 12
<211> LENGTH: 71
<212> TYPE: DNA
<213> ORGANISM: Homo sapiens

<400> SEQUENCE: 12
ttgcctgctc gacttagatc cacctactgt gacctttgt accactcttt ttcggtcaaa       60
aacgagatca g                                                           71

<210> SEQ ID NO 13
<211> LENGTH: 37
<212> TYPE: DNA
<213> ORGANISM: Homo sapiens

<400> SEQUENCE: 13
taccagctta acacatagca tcactggata gcgacgt                               37
```

```
<210> SEQ ID NO 14
<211> LENGTH: 73
<212> TYPE: DNA
<213> ORGANISM: Homo sapiens

<400> SEQUENCE: 14
ttgcctgctc gacttagatc cgcgtctcct ttgatttgta ccactctttt tccaataact    60
aaaggtacaa cat                                                       73

<210> SEQ ID NO 15
<211> LENGTH: 73
<212> TYPE: DNA
<213> ORGANISM: Homo sapiens

<400> SEQUENCE: 15
ttgcctgctc gacttagatc cacctactgt gacccttgt accactcttt ttcaataact     60
aaaggtacaa cac                                                       73

<210> SEQ ID NO 16
<211> LENGTH: 37
<212> TYPE: DNA
<213> ORGANISM: Homo sapiens

<400> SEQUENCE: 16
ggcataataa tctccaaaga tcactggata gcgacgt                              37

<210> SEQ ID NO 17
<211> LENGTH: 68
<212> TYPE: DNA
<213> ORGANISM: Homo sapiens

<400> SEQUENCE: 17
ttgcctgctc gacttagatc cgcgtctcct ttgatttgta ccactctttt tccagtggtt    60
ttccaacg                                                             68

<210> SEQ ID NO 18
<211> LENGTH: 70
<212> TYPE: DNA
<213> ORGANISM: Homo sapiens

<400> SEQUENCE: 18
ttgcctgctc gacttagatc cacctactgt gacccttgt accactcttt ttcacagtgg     60
ttttccaaca                                                           70

<210> SEQ ID NO 19
<211> LENGTH: 32
<212> TYPE: DNA
<213> ORGANISM: Homo sapiens

<400> SEQUENCE: 19
tgaacacacc gggtatcact ggatagcgac gt                                   32

<210> SEQ ID NO 20
<211> LENGTH: 18
<212> TYPE: DNA
<213> ORGANISM: Homo sapiens

<400> SEQUENCE: 20
ttgcctgctc gacttaga                                                  18
```

```
<210> SEQ ID NO 21
<211> LENGTH: 18
<212> TYPE: DNA
<213> ORGANISM: Homo sapiens

<400> SEQUENCE: 21
acgtcgctat ccagtgat                                                    18

<210> SEQ ID NO 22
<211> LENGTH: 15
<212> TYPE: DNA
<213> ORGANISM: Homo sapiens

<400> SEQUENCE: 22
ccgcgtctcc tttga                                                       15

<210> SEQ ID NO 23
<211> LENGTH: 16
<212> TYPE: DNA
<213> ORGANISM: Homo sapiens

<400> SEQUENCE: 23
ccacctactg tgaccc                                                      16

<210> SEQ ID NO 24
<211> LENGTH: 15
<212> TYPE: DNA
<213> ORGANISM: Artificial
<220> FEATURE:
<223> OTHER INFORMATION: Synthetic DNA

<400> SEQUENCE: 24
catgccaatg acgga                                                       15

<210> SEQ ID NO 25
<211> LENGTH: 15
<212> TYPE: DNA
<213> ORGANISM: Artificial
<220> FEATURE:
<223> OTHER INFORMATION: Synthetic DNA

<400> SEQUENCE: 25
catgcgaatg acggc                                                       15
```

US 7,153,658 B2

METHODS AND COMPOSITIONS FOR DETECTING TARGETS

I. CROSS REFERENCE TO RELATED APPLICATIONS

This application claims the benefit under 35 U.S.C. § 119(e) of prior U.S. Provisional Patent Application No. 60/412,225, filed Sep. 19, 2002, which is incorporated herein by reference.

II. FIELD OF THE INVENTION

The invention relates to methods and compositions for the detection of targets in a sample.

III. BACKGROUND

The detection of the presence or absence of (or quantity of) one or more target sequences in a sample containing one or more target sequences is commonly practiced. For example, the detection of cancer and many infectious diseases, such as AIDS and hepatitis, routinely includes screening biological samples for the presence or absence of diagnostic nucleic acid sequences. Also, detecting the presence or absence of nucleic acid sequences is often used in forensic science, paternity testing, genetic counseling, and organ transplantation.

An organism's genetic makeup is determined by the genes contained within the genome of that organism. Genes are composed of long strands or deoxyribonucleic acid (DNA) polymers that encode the information needed to make proteins. Properties, capabilities, and traits of an organism often are related to the types and amounts of proteins that are, or are not, being produced by that organism.

A protein can be produced from a gene as follows. First, the DNA of the gene that encodes a protein, for example, protein "X", is converted into ribonucleic acid (RNA) by a process known as "transcription." During transcription, a single-stranded complementary RNA copy of the gene is made. Next, this RNA copy, referred to as protein X messenger RNA (mRNA), is used by the cell's biochemical machinery to make protein X, a process referred to as "translation." Basically, the cell's protein manufacturing machinery binds to the mRNA, "reads" the RNA code, and "translates" it into the amino acid sequence of protein X. In summary, DNA is transcribed to make mRNA, which is translated to make proteins.

The amount of protein X that is produced by a cell often is largely dependent on the amount of protein X mRNA that is present within the cell. The amount of protein X mRNA within a cell is due, at least in part, to the degree to which gene X is expressed. Whether a particular gene is expressed, and if so, to what level, may have a significant impact on the organism.

IV. SUMMARY OF THE INVENTION

In certain embodiments, methods are provided for detecting at least one target nucleic acid sequence in a sample. In certain embodiments, the methods comprise forming a ligation reaction composition comprising the sample and a ligation probe set for each target nucleic acid sequence. In certain embodiments, the probe set comprises: (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence; and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence. In certain embodiments, the probes in each set are suitable for ligation together when hybridized adjacent to one another on a complementary target nucleic acid sequence.

In certain embodiments, the methods further comprise forming a test composition by subjecting the ligation reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion.

In certain embodiments, the methods further comprise forming an amplification reaction composition comprising: the test composition;
a polymerase;
a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion;
a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and
at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the amplification reaction composition to at least one amplification reaction. In certain embodiments, the methods further comprise detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence, and wherein no threshold difference between the first detectable signal value and the second detectable signal value of the first labeled probe and no threshold difference between the first detectable signal value and the second detectable signal value of the second labeled probe indicates the absence of the target nucleic acid sequence.

In certain embodiments, methods are provided for detecting at least one target nucleic acid sequence in a sample. In certain embodiments, the methods comprise forming a ligation reaction composition comprising the sample and a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence. In certain embodiments, the probes in each set are suitable for ligation together when hybridized adjacent to one another on a complementary target nucleic acid sequence. In certain embodiments, at least one of the at least one first probe and the at least one second probe further comprises: (a) a first addressable portion located between the primer-specific portion and the target-specific portion, wherein the first addressable portion comprises a sequence, and (b) a second addressable portion located between the primer-specific portion and the target-specific portion, wherein the second addressable portion comprises a sequence.

In certain embodiments, the methods further comprise forming a test composition by subjecting the ligation reaction composition to at least one cycle of ligation, wherein adjacently hybridizing complementary probes are ligated to one another to form a ligation product comprising the 5' primer-specific portion, the first addressable portion, the second addressable portion, the target-specific portions, and the 3' primer-specific portion.

In certain embodiments, the methods further comprise forming an amplification reaction composition comprising:
the test composition;
a polymerase;
a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion;
a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and
at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the amplification reaction composition to at least one amplification reaction. In certain embodiments, the methods further comprise detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence, and wherein no threshold difference between the first detectable signal value and the second detectable signal value of the first labeled probe and no threshold difference between the first detectable signal value and the second detectable signal value of the second labeled probe indicates the absence of the target nucleic acid sequence.

In certain embodiments, methods are provided for detecting at least one target nucleic acid sequence in a sample. In certain embodiments, the methods comprise forming a reaction composition comprising the sample and a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence. In certain embodiments, the probes in each set are suitable for ligation together when hybridized adjacent to one another on a complementary target nucleic acid sequence, and one probe in each probe set further comprises an addressable portion located between the primer-specific portion and the target-specific portion, wherein the addressable portion comprises a sequence.

In certain embodiments, the reaction composition further comprises:
a polymerase;
a labeled probe, wherein the labeled probe has a first detectable signal value when it is not hybridized to a complementary sequence, and wherein the labeled probe comprises the sequence of the addressable portion or comprises a sequence complementary to the sequence of the addressable portion; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the reaction composition to at least one cycle of ligation, wherein adjacently hybridizing complementary probes are ligated to one another to form a ligation product comprising the 5' primer-specific portion, the target-specific portions, the addressable portion, and the 3' primer-specific portion.

In certain embodiments, the methods further comprise, after the at least one cycle of ligation, subjecting the reaction composition to at least one amplification reaction. In certain embodiments, the methods further comprise detecting a second detectable signal value at least one of during and after the amplification reaction, wherein a threshold difference between the first detectable signal value and the second detectable signal value indicates the presence of the target nucleic acid sequence, and wherein no threshold difference between the first detectable signal value and the second detectable signal value indicates the absence of the target nucleic acid sequence.

In certain embodiments, methods are provided for detecting at least one target nucleic acid sequence in a sample. In certain embodiments, the methods comprise forming a reaction composition comprising the sample and a ligation probe set for each target nucleic acid sequence. In certain embodiments, the probe set comprises: (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence; and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence. In certain embodiments, the probes in each set are suitable for ligation together when hybridized adjacent to one another on a complementary target nucleic acid sequence.

In certain embodiments, the reaction composition further comprises:
a polymerase;
a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion;
a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and
at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion.

In certain embodiments, the methods further comprise, after the at least one cycle of ligation, subjecting the reaction composition to at least one amplification reaction. In certain embodiments, the methods further comprise detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence, and wherein no threshold difference between the first detectable signal value and the second detectable signal value of the first labeled probe and no threshold difference between the first detectable signal value and the second detectable signal value of the second labeled probe indicates the absence of the target nucleic acid sequence.

In certain embodiments, methods are provided for detecting at least one target nucleic acid sequence in a sample. In certain embodiments, the methods comprise forming a reaction composition comprising the sample and a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence. In certain embodiments, the probes in each set are suitable for ligation together when hybridized adjacent to one another on a complementary target nucleic acid sequence. In certain embodiments, at least one of the at least one first probe and the at least one second probe further comprises:

(a) a first addressable portion located between the primer-specific portion and the target-specific portion, wherein the first addressable portion comprises a sequence, and (b) a second addressable portion located between the primer-specific portion and the target-specific portion, wherein the second addressable portion comprises a sequence.

In certain embodiments, the reaction composition further comprises:
a polymerase;
a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion;
a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and
at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion.

In certain embodiments, the methods further comprise, after the at least one cycle of ligation, subjecting the reaction composition to at least one amplification reaction. In certain embodiments, the methods further comprise detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence, and wherein no threshold difference between the first detectable signal value and the second detectable signal value of the first labeled probe and no threshold difference between the first detectable signal value and the second detectable signal value of the second labeled probe indicates the absence of the target nucleic acid sequence.

In certain embodiments, methods are provided for making a library of probes. In certain embodiments, the methods comprise synthesizing a first library of $4^X$ probes each comprising a primer-specific portion, a target-specific portion X nucleotides in length, and a first addressable portion located between the primer-specific portion and the target-specific portion, wherein each of the $4^X$ probes of the first library of $4^X$ probes comprises a different target-specific portion. In certain embodiments, X is 4 to 8.

In certain embodiments, methods are provided for selecting a probe. In certain embodiments, the methods comprise selecting from a first library of probes a probe that comprises a target-specific portion that is complementary to a desired portion of X nucleotides of a target nucleic acid sequence. In certain embodiments, X is 4 to 8. In certain embodiments, the first library of probes comprises $4^X$ probes that each comprise a primer-specific portion, a target-specific portion X nucleotides in length, and a first addressable portion located between the primer-specific portion and the target-specific portion, wherein each of the $4^X$ probes comprises a different target-specific portion.

In certain embodiments, a first library of $4^X$ probes is provided. In certain embodiments, each of the probes comprises a primer-specific portion, a target-specific portion X nucleotides in length, and a first addressable portion located between the primer-specific portion and the target-specific portion, wherein each of the $4^X$ probes of the first library of $4^X$ probes comprises a different target-specific portion. In certain embodiments, X is 4 to 8.

In certain embodiments, methods are provided for making a library of ($4^{(X-1)}$ multiplied by 6) pairs of probes, comprising synthesizing a library of ($4^{(X-1)}$ multiplied by 6) pairs of probes. In certain embodiments, one probe of each pair comprises a primer-specific portion, a target-specific portion comprising a sequence of X nucleotides, and a first addressable portion located between the primer-specific portion and the target-specific portion. In certain embodiments, the other probe of each pair comprises a primer-specific portion, a target-specific portion comprising a sequence of X nucleotides, and a second addressable portion located between the primer-specific portion and the target-specific portion. In certain embodiments, the sequence of X nucleotides of the target-specific portion of each probe in a pair of probes is identical except for one nucleotide difference. In certain embodiments, each of the ($4^{(X-1)}$ multiplied by 6) pairs of probes can be used to determine whether a target nucleic acid sequence comprising X nucleotides has one of two possible nucleic acid sequences, wherein the two possible nucleic acid sequences differ by one nucleotide at a single position, and wherein at least one separate pair of probes of the library is provided for each separate possible one nucleotide difference at one position in a target nucleic acid comprising X nucleotides. In certain embodiments, X is 4 to 8.

In certain embodiments, a library of ($4^{(X-1)}$ multiplied by 6) pairs of probes is provided. In certain embodiments, one probe of each pair comprises a primer-specific portion, a target-specific portion comprising a sequence of X nucleotides, and a first addressable portion located between the primer-specific portion and the target-specific portion. In certain embodiments, the other probe of each pair comprises a primer-specific portion, a target-specific portion comprising a sequence of X nucleotides, and a second addressable portion located between the primer-specific portion and the target-specific portion. In certain embodiments, the sequence of X nucleotides of the target-specific portion of each probe in a pair of probes is identical except for one nucleotide difference. In certain embodiments, each of the ($4^{(X-1)}$ multiplied by 6) pairs of probes can be used to determine whether a target nucleic acid sequence comprising X nucleotides has one of two possible nucleic acid sequences, wherein the two possible nucleic acid sequences differ by one nucleotide at a single position, and wherein at least one separate pair of probes of the library is provided for each separate possible one nucleotide difference at one position in a target nucleic acid comprising X nucleotides. In certain embodiments, X is 4 to 8.

In certain embodiments, kits are provided for detecting at least one target nucleic acid sequence. In certain embodiments, the kits comprise a ligation probe set for each target nucleic acid sequence. In certain embodiments, the probe set comprises: (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence; and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence. In certain embodiments, the probes in each set are suitable for ligation together when hybridized adjacent to one another on a complementary target nucleic acid sequence.

In certain embodiments, the kits further comprise:
a first labeled probe comprising the sequence of the first addressable portion or comprising a sequence complementary to the sequence of the first addressable portion; and
a second labeled probe comprising the sequence of the second addressable portion or comprising a sequence complementary to the sequence of the second addressable portion.

In certain embodiments, kits are provided for detecting at least one target nucleic acid sequence. In certain embodiments, the kits comprise a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence. In certain embodiments, the probes in each set are suitable for ligation together when hybridized adjacent to one another on a complementary target nucleic acid sequence. In certain embodiments, at least one of the at least one first probe and the at least one second probe further comprises: (a) a first addressable portion located between the primer-specific portion and the target-specific portion, wherein the first addressable portion comprises a sequence, and (b) a second addressable portion located between the primer-specific portion and the target-specific portion, wherein the second addressable portion comprises a sequence.

In certain embodiments, the kits further comprise:
a first labeled probe comprising the sequence of the first addressable portion or comprising a sequence complementary to the sequence of the first addressable portion; and
a second labeled probe comprising the sequence of the second addressable portion or comprising a sequence complementary to the sequence of the second addressable portion.

In certain embodiments, methods are provided for detecting at least one target nucleic acid sequence in a sample. In certain embodiments, the methods comprise forming a ligation reaction composition comprising the sample and a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence and wherein a minor groove binder is attached to the second probe. In certain embodiments, the probes in each set are suitable for ligation together when hybridized adjacent to one another on a complementary target nucleic acid sequence.

In certain embodiments, the methods further comprise forming a test composition by subjecting the ligation reaction composition to at least one cycle of ligation, wherein adjacently hybridizing complementary probes are ligated to one another to form a ligation product comprising the 5' primer-specific portion, the target-specific portions, and the 3' primer-specific portion.

In certain embodiments, the methods further comprise forming an amplification reaction composition comprising:

the test composition;

a polymerase; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the amplification reaction composition to at least one amplification reaction. In certain embodiments, the methods further comprise detecting the presence or absence of the at least one target nucleic acid sequence by detecting the presence or absence of the ligation product.

In certain embodiments, methods are provided for detecting at least one target nucleic acid sequence in a sample. In certain embodiments, the methods comprise forming a reaction composition comprising the sample and a ligation probe set for each target nucleic acid sequence. In certain embodiments, the probe set comprises (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence and wherein a minor groove binder is attached to the second probe. In certain embodiments, the probes in each set are suitable for ligation together when hybridized adjacent to one another on a complementary target nucleic acid sequence.

In certain embodiments, the reaction composition further comprises:

a polymerase; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product.

In certain embodiments, the methods further comprise subjecting the reaction composition to at least one cycle of ligation, wherein adjacently hybridizing complementary probes are ligated to one another to form a ligation product comprising the 5' primer-specific portion, the target-specific portions, and the 3' primer-specific portion.

In certain embodiments, the methods further comprise, after the at least one cycle of ligation, subjecting the reaction composition to at least one amplification reaction. In certain embodiments, the methods further comprise detecting the presence or absence of the at least one target nucleic acid sequence by detecting the presence or absence of the ligation product.

V. BRIEF DESCRIPTION OF THE DRAWINGS

The skilled artisan will understand that the drawings, described below, are for illustration purposes only. The figures are not intended to limit the scope of the invention in any way.

FIG. 1. Schematic showing of labeled probes according to certain exemplary embodiments.

FIG. 2 (2A–2E). Schematic showing an exemplary embodiment of certain embodiments comprising ligation and primer extension amplification.

FIG. 5 (5A–5D) schematically illustrates exemplary embodiments comprising ligation and primer extension followed by transcription.

Figure 6:
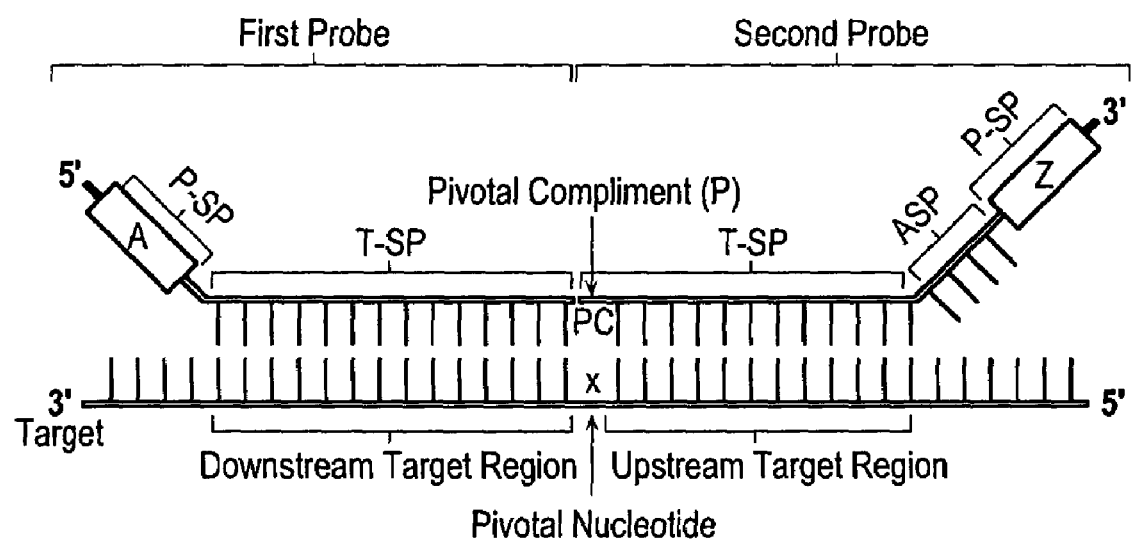

FIG. 6 is a schematic showing a ligation probe set according to certain embodiments of the invention.

Each probe includes a portion that is complementary to the target (the "target-specific portion," T-SP) and a portion that is complementary to or has the same sequence as a primer (the "primer-specific portion," P-SP). At least one probe in each probe set further comprises an addressable portion (ASP) that is located between the target-specific portion and the primer-specific portion (here, the second probe).

Each probe set comprises at least one first probe and at least one second probe that are designed to hybridize with the target with the 3' end of the first probe (here, probe A) immediately adjacent to and opposing the 5' end of the second probe (here, probe Z).

Figure 7:
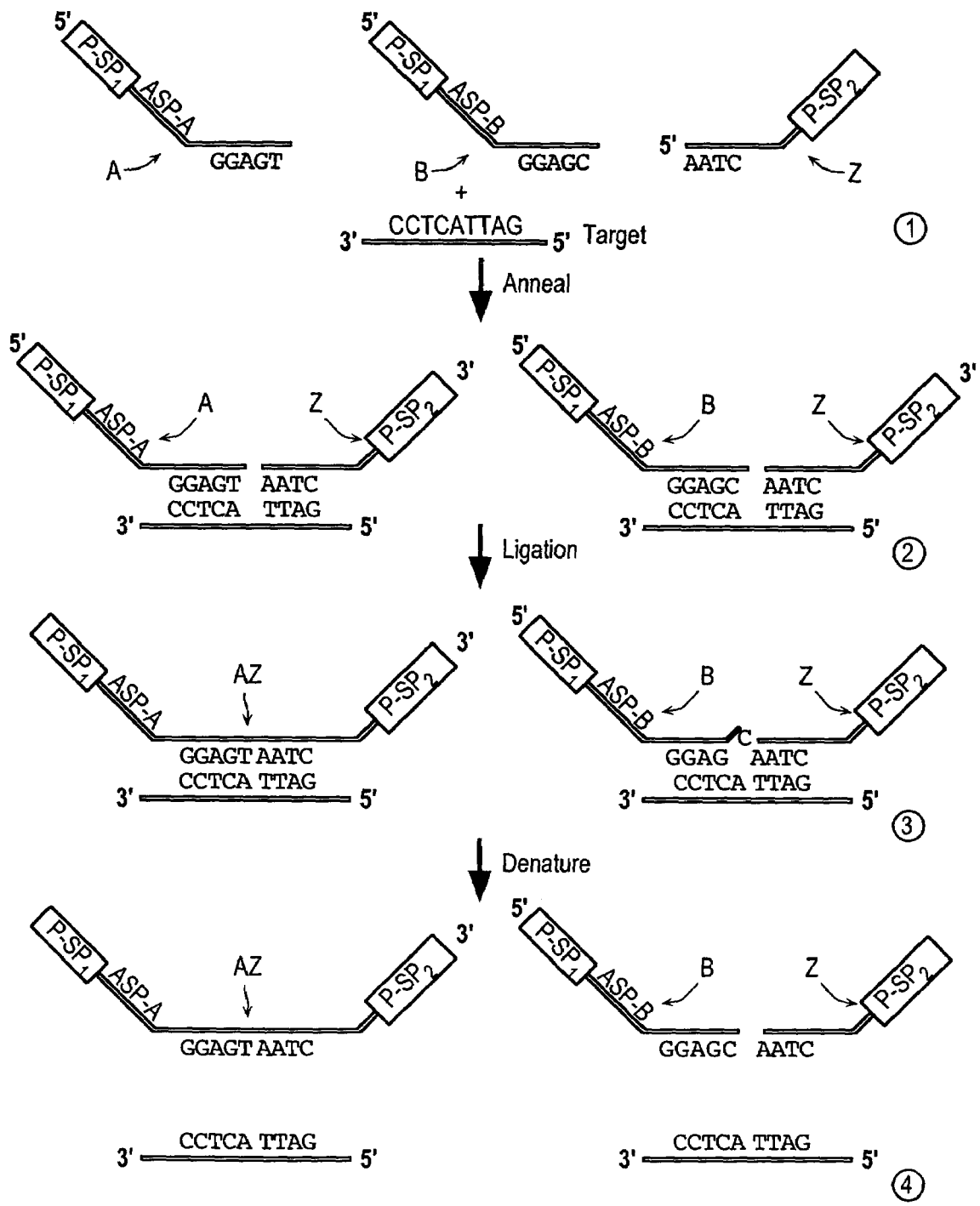

FIG. 7 depicts a method for differentiating between two potential alleles in a target locus using certain embodiments of the invention.

FIG. 7 at (1) shows: (i) a target-specific probe set comprising: two first probes (A and B) that have the same primer-specific portions (P-SP1), the same target-specific portions except for different pivotal complements (here, T at the 3' end probe A and C at the 3' end probe B) and different addressable portions ((ASP-A) and (ASP-B)); and one second probe (Z) comprising a target-specific portion and a primer-specific portion (P-SP2).

FIG. 7 at (2) shows the three probes annealed to the target. The target-specific portion of probe A is fully complementary with the 3' target region including the pivotal nucleotide. The pivotal complement of probe B is not complementary with the 3' target region. The target-specific portion of probe B, therefore, contains a base-pair mismatch at the 3' end. The target-specific portion of probe Z is fully complementary to the 5' target region.

FIG. 7 at (3) shows ligation of probes A and Z to form ligation product A-Z. Probes B and Z are not ligated together to form a ligation product due to the mismatched pivotal complement on probe B.

FIG. 7 at (4) shows denaturing the double-stranded molecules to release the A-Z ligation product and unligated probes B and Z.

FIG. 8 (8A–8C) is a schematic depicting certain embodiments of the invention.

FIG. 8(1) depicts a target sequence and a ligation probe set comprising: two first probes (A and B) that have the same primer-specific portions (P-SP1), the same target-specific portions except for different pivotal complements (here, T at the 3' end probe A and G at the 3' end probe B) and different addressable portions ((ASP-A) and (ASP-B)); and one second probe (Z) comprising a target-specific portion and a primer-specific portion (P-SP2).

FIG. 8(2) depicts the A and Z probes hybridized to the target equence under annealing conditions.

FIG. 8(3) depicts the ligation of the first and second probes in the presence of a ligation agent to form ligation product.

FIG. 8(4) depicts denaturing the ligation product:target complex to release a single-stranded ligation product; adding a primer set (P1 and P2) and two labeled probes (LBP-A and LBP-B); and annealing primer P2 to the ligation product.

FIG. 8(5) depicts the formation of a double-stranded nucleic acid product by extending the P2 primer in a template-dependent manner with a polymerase.

FIGS. 8(6)–(11) depict additional cycles of amplification.

Figure 9A:
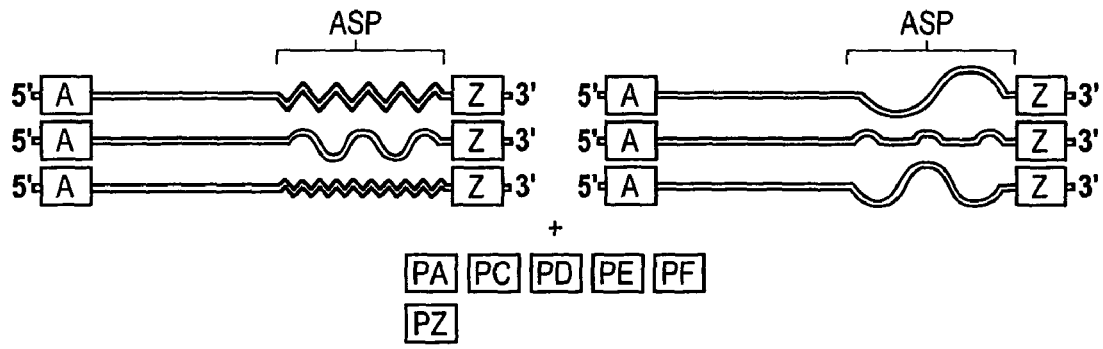
Figure 9B:
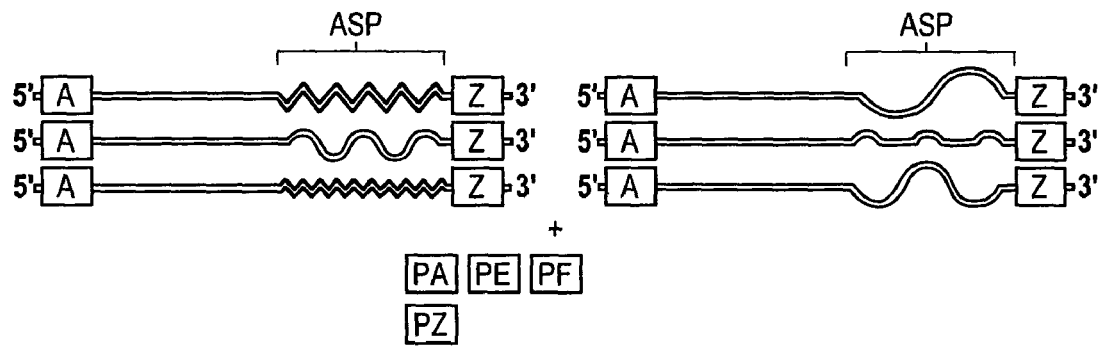
Figure 9C:
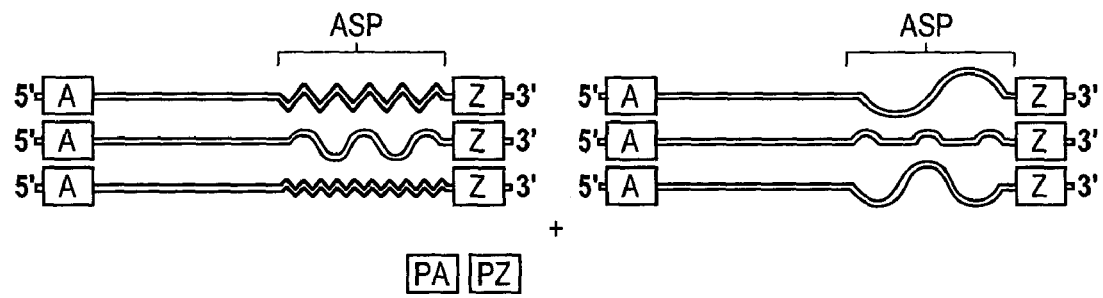

FIGS. 9(A)–(C) depicts various combinations of ligation products in which two or more ligation products comprise the same primer-specific portions.

Figure 10:
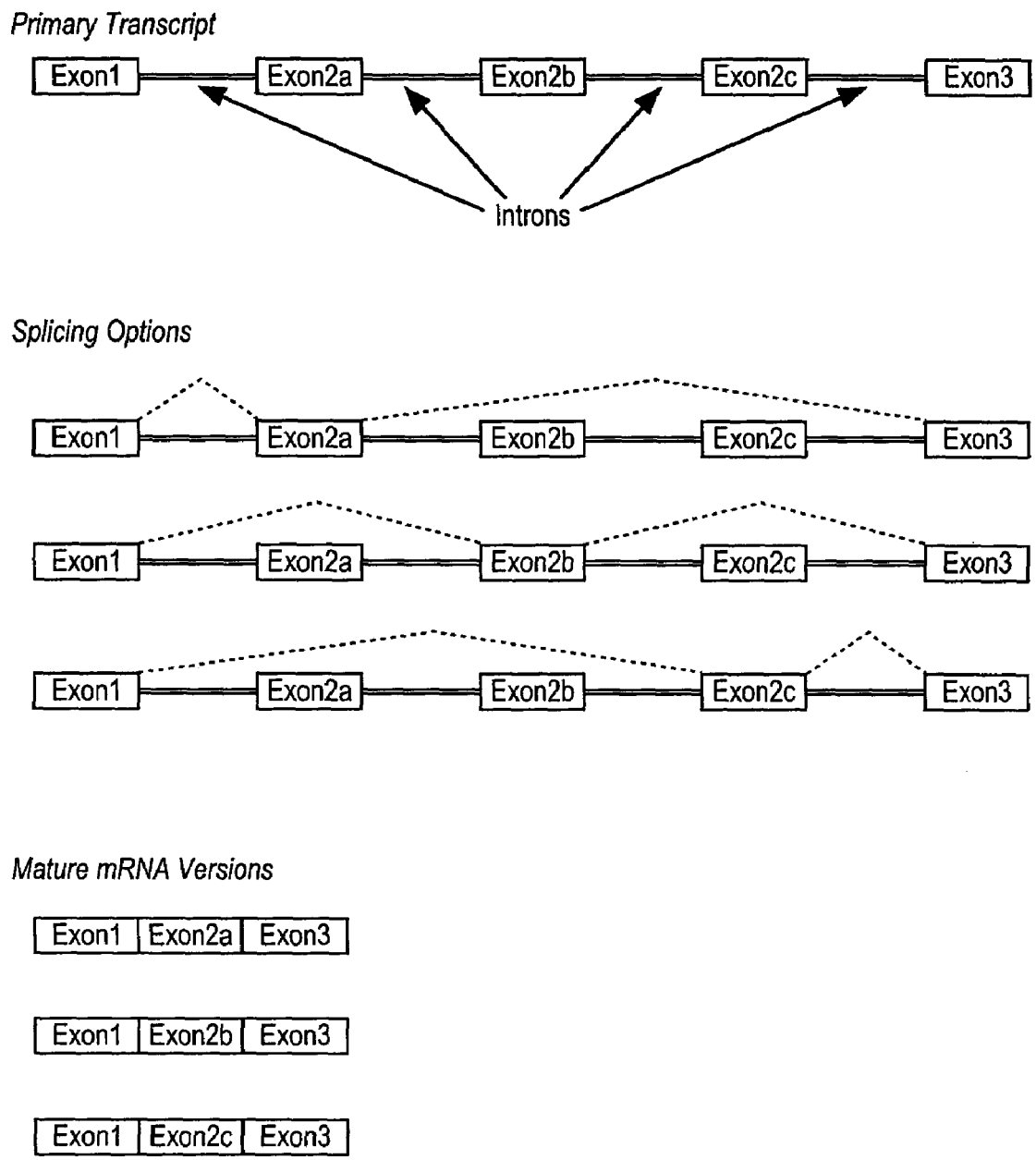

FIG. 10 depicts exemplary alternative splicing.

Figure 11:
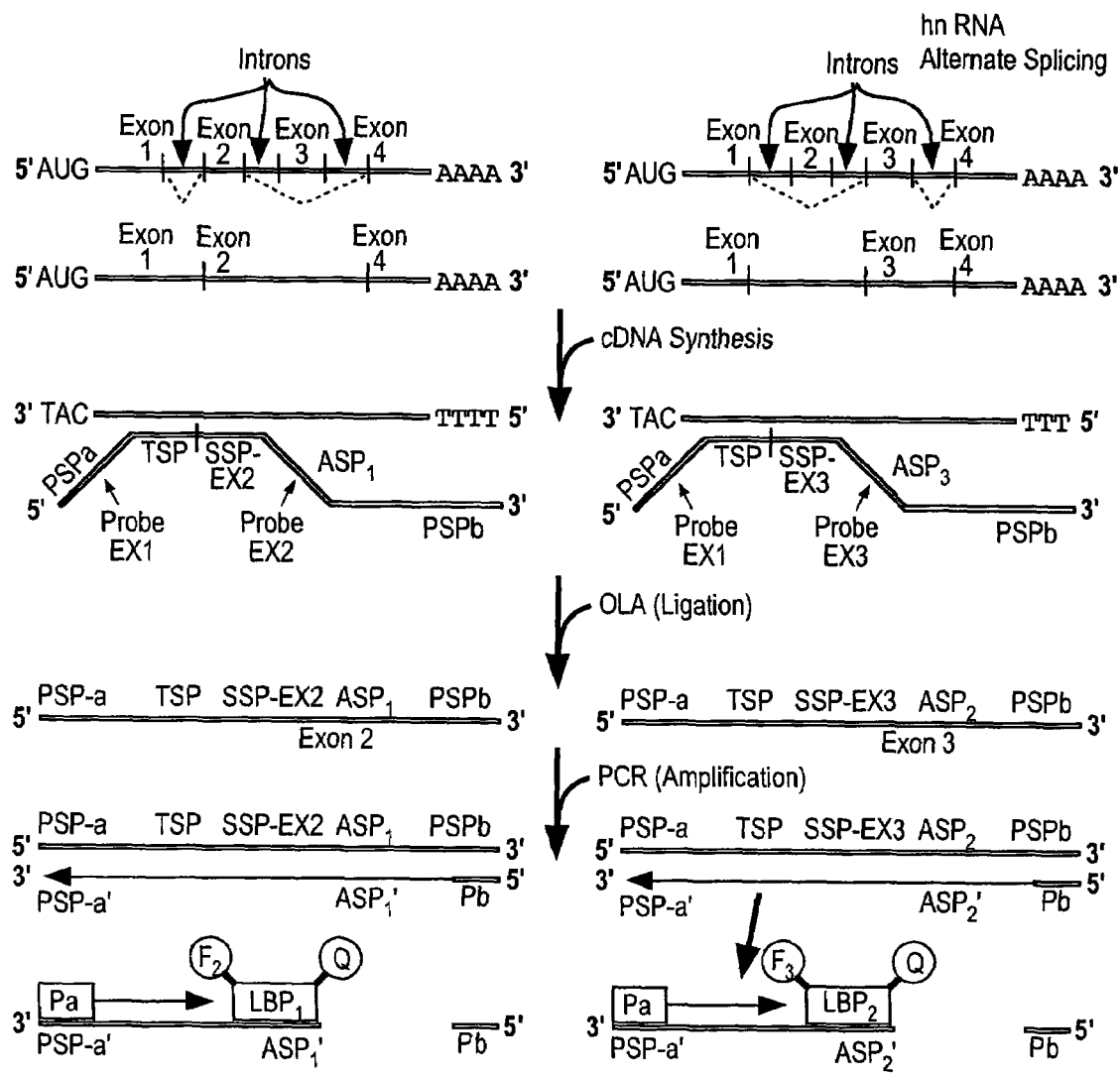

FIG. 11 depicts certain embodiments involving splice variants.

Figure 12A:
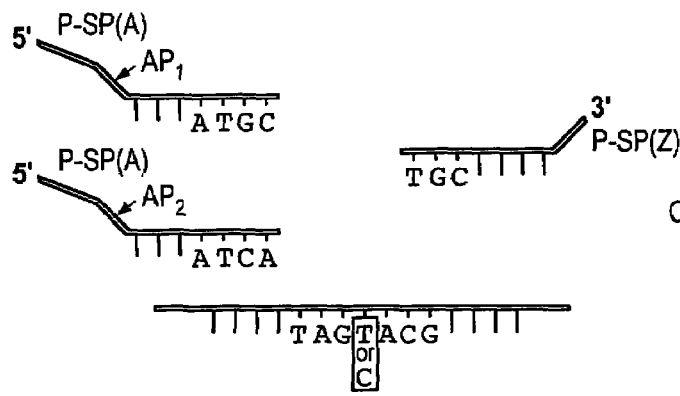
Figure 12B:
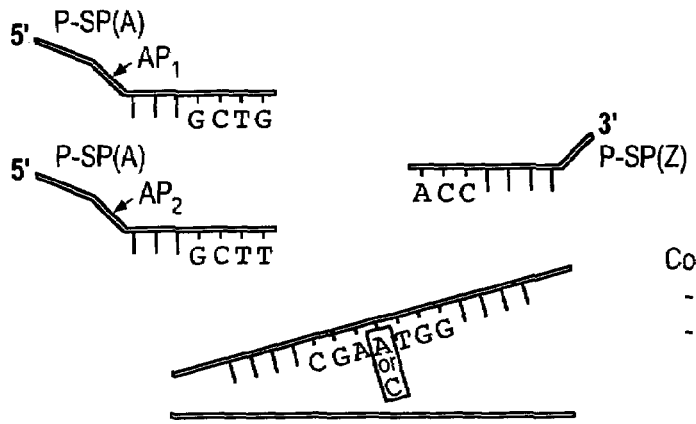
Figure 12C:
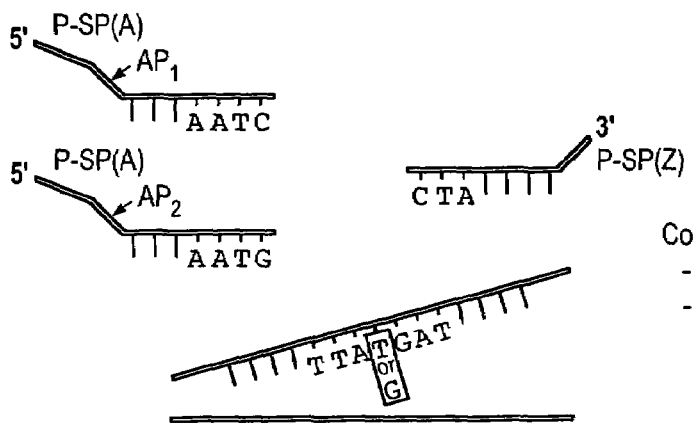

FIG. 12 (12A–12C) depicts certain embodiments involving three biallelic loci.

Figure 13A:
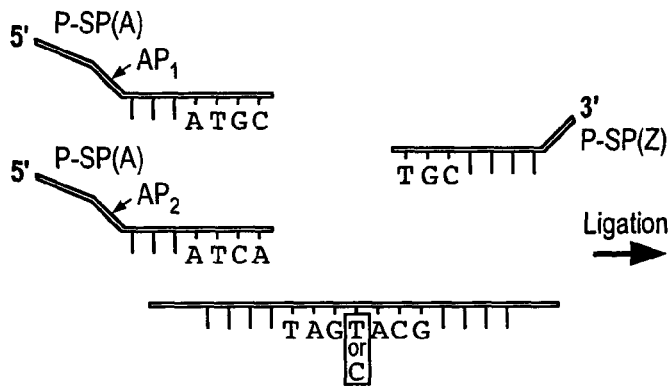
Figure 13B:
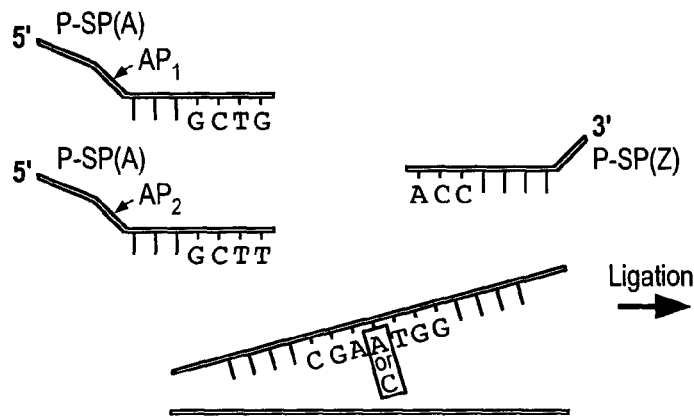
Figure 13C:
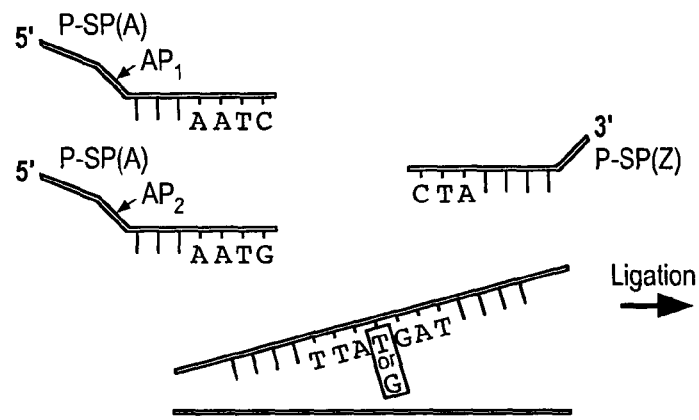

FIG. 13 (13A–13C) depicts certain embodiments involving three biallelic loci.

FIG. 14 (14A–14D) depicts certain embodiments in which one probe of a ligation probe set also serves as a primer.

Figure 15:
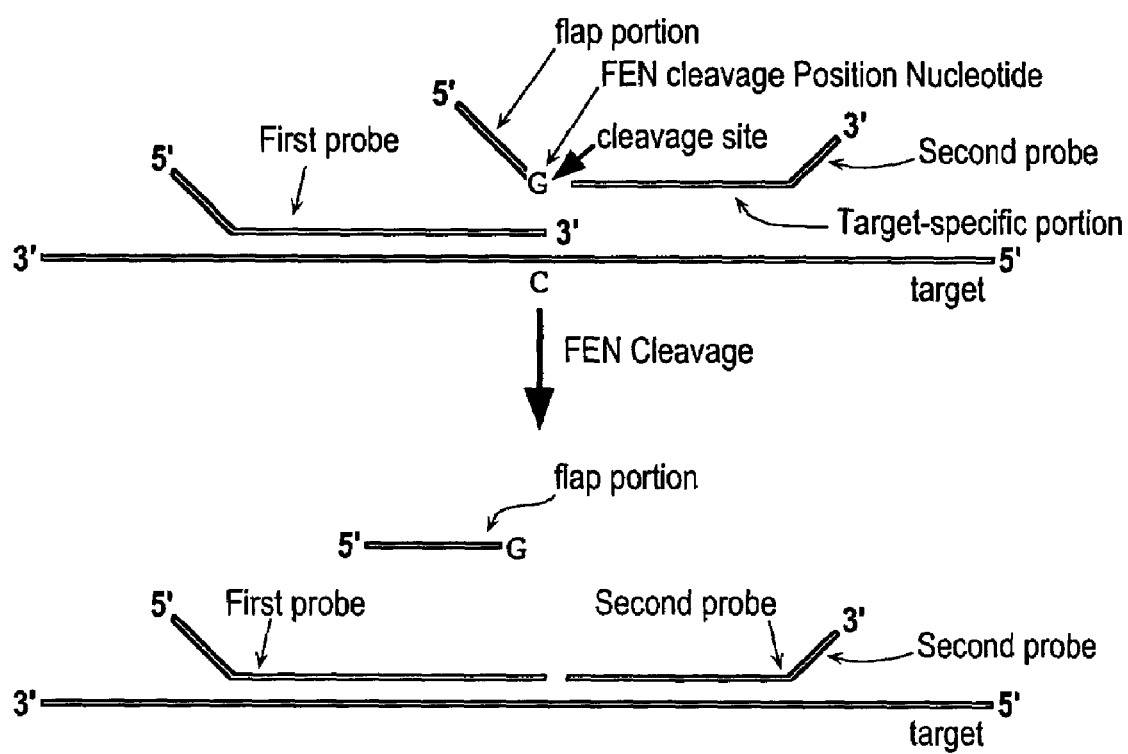

FIG. 15 depicts certain embodiments employing flap endonuclease.

FIG. 16 (16A–16C) depicts certain embodiments employing flap endonuclease.

FIG. 17 (17A–17C) depicts certain embodiments employing flap endonuclease.

FIG. 18 (18A–18C) depicts certain embodiments employing flap endonuclease.

Figure 19:
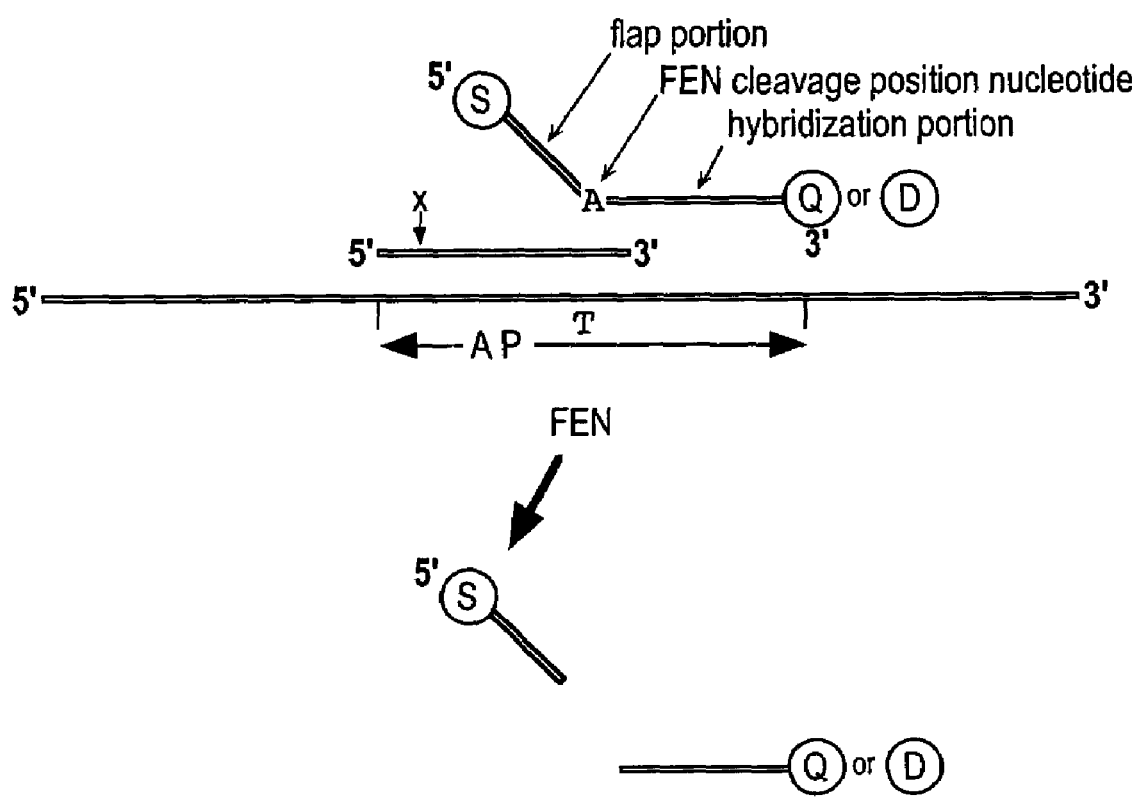

FIG. 19 depicts certain embodiments employing flap endonuclease.

VI. DETAILED DESCRIPTION OF CERTAIN EXEMPLARY EMBODIMENTS

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. U.S. patent application Ser. No. 09/584,905, filed May 30, 2000, Ser. No. 09/724,755, filed Nov. 28, 2000, Ser. No. 10/011,993, filed Dec. 5, 2001, and Patent Cooperation Treaty Application No. PCT/US01/17329, filed May 30, 2001, are hereby expressly incorporated by reference in their entirety for any purpose.

A. Certain Definitions

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385–394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$–$C_6$ alkyl or $C_5$–$C_{14}$ aryl. Exemplary riboses include, but are not limited to, 2'-(C1–C6)alkoxyribose, 2'-(C5–C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1–C6)alkylribose, 2'-deoxy-3'-(C1–C6)alkoxyribose and 2'-deoxy-3'-(C5–C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

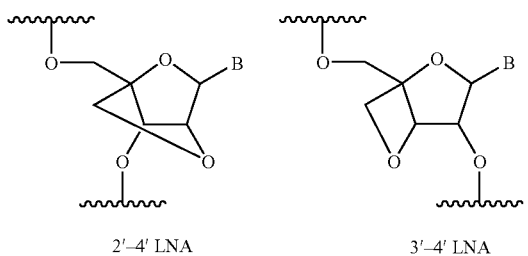

2'–4' LNA          3'–4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159–65; Fujimori (1990) J. Amer. Chem. Soc. 112: 7435; Urata, (1993) Nucleic Acids Symposium Ser. No. 29:69–70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, $2^{nd}$ Ed., Freeman, San Francisco, Calif.).

One or more of the pentose carbons of a nucleotide may be substituted with a phosphate ester having the formula:

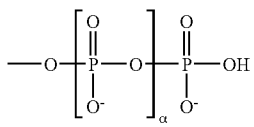

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide", "oligonucleotide", and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occuring nucleotides and nucleotide analogs. nucleic acids typically range in size from a few monomeric units, e.g. 5–40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

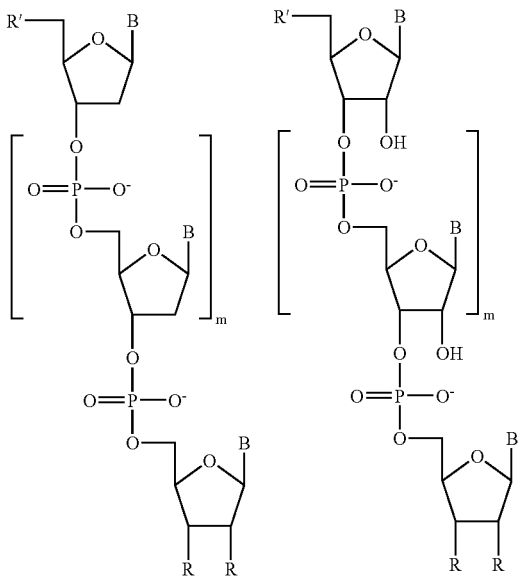

wherein each B is independently the base moiety of a nucleotide, e.g., a purine, a 7-deazapurine, a pyrimidine, or an analog nucleotide; each m defines the length of the respective nucleic acid and can range from zero to thousands, tens of thousands, or even more; each R is independently selected from the group comprising hydrogen, halogen, —R'', —OR'', and —NR''R'', where each R'' is independently (C1–C6)alkyl or (C5–C14)aryl, or two adjacent Rs are taken together to form a bond such that the ribose sugar is 2',3'-didehydroribose; and each R' is independently hydroxyl or

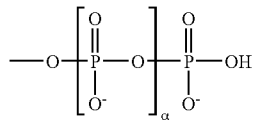

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254: 1497–1500; WO 92/20702; U.S. Pat. No. 5,719,262; U.S. Pat. No. 5,698, 685;); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497–1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$–$C_4$ alkylphosphonate, e.g. methylphosphonate; (ii) phosphoramidate; (iii) $C_1$–$C_6$ alkyl-phosphotriester; (iv) phosphorothioate; and (v) phosphorodithioate.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

An "enzymatically active mutant or variant thereof," when used in reference to an enzyme such as a polymerase or a ligase, means a protein with appropriate enzymatic activity. Thus, for example, but without limitation, an enzymatically active mutant or variant of a DNA polymerase is a protein that is able to catalyze the stepwise addition of appropriate deoxynucleoside triphosphates into a nascent DNA strand in a template-dependent manner. An enzymatically active mutant or variant differs from the "generally-accepted" or consensus sequence for that enzyme by at least one amino acid, including, but not limited to, substitutions of one or more amino acids, addition of one or more amino acids, deletion of one or more amino acids, and alterations to the amino acids themselves. With the change, however, at least some catalytic activity is retained. In certain embodiments, the changes involve conservative amino acid substitutions. Conservative amino acid substitution may involve replacing one amino acid with another that has, e.g., similar hydorphobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. The hydropathic index is discussed, e.g., in Kyte et al., J. Mol. Biol., 157:105–131 (1982). It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or normatural, that may be incorporated, either enzymatically or synthetically, into a polypeptide or protein.

Fragments, for example, but without limitation, proteolytic cleavage products, are also encompassed by this term, provided that at least some enzyme catalytic activity is retained.

The skilled artisan will readily be able to measure catalytic activity using an appropriate well-known assay. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups. Protocols for such assays may be found, among other places, in Sambrook et al., Molecular Cloning, A Laboratory Manual, Cold Spring Harbor Press (1989) (hereinafter "Sambrook et al."), Sambrook and Russell, Molecular Cloning, Third Edition, Cold Spring Harbor Press (2000) (hereinafter "Sambrook and Russell"), Ausbel et al., Current Protocols in Molecular Biology (1993) including supplements through April 2001, John Wiley & Sons (hereinafter "Ausbel et al.").

A "target" or "target nucleic acid sequence" according to the present invention comprises a specific nucleic acid sequence that can be distinguished by a probe. Targets may include both naturally occurring and synthetic molecules.

"Probes", according to the present invention, comprise oligonucleotides that comprise a specific portion that is designed to hybridize in a sequence-specific manner with a complementary region on a specific nucleic acid sequence, e.g., a target nucleic acid sequence. In certain embodiments, the specific portion of the probe may be specific for a particular sequence, or alternatively, may be degenerate, e.g., specific for a set of sequences.

A "ligation probe set" according to the present invention is a group of two or more probes designed to detect at least one target. As a non-limiting example, a ligation probe set may comprise two nucleic acid probes designed to hybridize to a target such that, when the two probes are hybridized to the target adjacent to one another, they are suitable for ligation together.

When used in the context of the present invention, "suitable for ligation" refers to at least one first target-specific probe and at least one second target-specific probe, each comprising an appropriately reactive group. Exemplary reactive groups include, but are not limited to, a free hydroxyl group on the 3' end of the first probe and a free phosphate group on the 5' end of the second probe. Exemplary pairs of reactive groups include, but are not limited to: phosphorothioate and tosylate or iodide; esters and hydrazide; $RC(O)S^-$, haloalkyl, or $RCH_2S$ and α-haloacyl; thiophosphoryl and bromoacetoamido groups. Exemplary reactive groups include, but are not limited to, S-pivaloyloxymethyl-4-thiothymidine. Additionally, in certain embodiments, first and second target-specific probes are hybridized to the target sequence such that the 3' end of the first target-specific probe and the 5' end of the second target-specific probe are immediately adjacent to allow ligation.

The term "signal moiety" as used herein refers to any tag, label, or identifiable moiety.

"Detectably different signal" means that detectable signals from different signal moieties are distinguishable from one another by at least one detection method.

The term "detectable signal value" refers to a value of the signal that is detected from a label. In certain embodiments, the detectable signal value is the amount or intensity of signal that is detected from a label. Thus, if there is no detectable signal value from a label, its detectable signal value is zero (0). In certain embodiments, the detectable signal value is a characteristic of the signal other than the amount or intensity of the signal, such as the spectra, wavelength, color, or lifetime of the signal.

"Detectably different signal value" means that one or more detectable signal values are distinguishable from one another by at least one detection method.

The term "labeled probe" refers to a probe that provides a detectably different signal value depending upon whether a given nucleic acid sequence is present or absent. In certain embodiments, a labeled probe provides a detectably different signal value when the intact labeled probe is hybridized to a given nucleic acid sequence than when the intact labeled probe is not hybridized to a given nucleic acid sequence. Thus, if a given nucleic acid sequence is present, the labeled probe provides a detectably different signal value than when the given nucleic acid sequence is absent. In certain embodiments, a labeled probe provides a detectably different signal value when the probe is intact than when the probe is not intact. In certain such embodiments, a labeled probe remains intact unless a given nucleic acid sequence is present. In certain such embodiments, if a given nucleic acid sequence is present, the labeled probe is cleaved, which results in a detectably different signal value than when the probe is intact.

In certain embodiments, the labeled probe is an "interaction probe." The term "interaction probe" refers to a probe that comprises at least two moieties that can interact with one another to provide a detectably different signal value depending upon whether a given nucleic acid sequence is present or absent. The signal value that is detected from the interaction probe is different depending on whether the two moieties are sufficiently close to one another or are spaced apart from one another. During the methods described herein, the proximity of the two moieties to one another is different depending upon whether the given nucleic acid is present or absent.

In certain embodiments, the two moieties of the interaction probe are moved further apart if the given nucleic acid sequence is present. In certain embodiments, the interaction probe comprises two moieties that are linked together by a link element, and the two moieties become unlinked during the method if the given nucleic acid sequence is present. The signal value that is detected from the interaction probe that includes the two moieties linked together is different from the signal value that is detected from the interaction probe when the two moieties are not linked.

The term "threshold difference between signal values" refers to a set difference between a first detectable signal value and a second detectable signal value that results when the target nucleic acid sequence that is being sought is present in a sample, but that does not result when the target nucleic acid sequence is absent. The first detectable signal value of a labeled probe is the detectable signal value from the probe when it is not exposed to a given nucleic acid sequence. The second detectable signal value is detected during and/or after an amplification reaction using a composition that comprises the labeled probe.

The term "quantitating," when used in reference to an amplification product, refers to determining the quantity or amount of a particular sequence that is representative of a target nucleic acid sequence in the sample. For example, but without limitation, one may measure the intensity of the signal from a labeled probe. The intensity or quantity of the signal is typically related to the amount of amplification product. The amount of amplification product generated correlates with the amount of target nucleic acid sequence present prior to ligation and amplification, and thus, in certain embodiments, may indicate the level of expression for a particular gene.

The term "amplification product" as used herein refers to the product of an amplification reaction including, but not limited to, primer extension, the polymerase chain reaction, RNA transcription, and the like. Thus, exemplary amplification products may comprise at least one of primer extension products, PCR amplicons, RNA transcription products, and the like.

"Primers" according to the present invention refer to oligonucleotides that are designed to hybridize with the primer-specific portion of probes, ligation products, or amplification products in a sequence-specific manner, and serve as primers for amplification reactions.

A "universal primer" is capable of hybridizing to the primer-specific portion of more than one species of probe, ligation product, or amplification product, as appropriate. A "universal primer set" comprises a first primer and a second primer that hybridize with a plurality of species of probes, ligation products, or amplification products, as appropriate.

A "ligation agent" according to the present invention may comprise any number of enzymatic or chemical (i.e., non-enzymatic) agents that can effect ligation of nucleic acids to one another.

In this application, a statement that one sequence is the same as or is complementary to another sequence encompasses situations where both of the sequences are completely the same or complementary to one another, and situations where only a portion of one of the sequences is the same as, or is complementary to, a portion or the entire other sequence. Here, the term "sequence" encompasses, but is not limited to, nucleic acid sequences, polynucleotides, oligonucleotides, probes, primers, primer-specific portions, target-specific portions, addressable portions, and oligonucleotide link elements.

In this application, a statement that one sequence is complementary to another sequence encompasses situations in which the two sequences have mismatches. Here, the term "sequence" encompasses, but is not limited to, nucleic acid sequences, polynucleotides, oligonucleotides, probes, primers, primer-specific portions, target-specific portions, addressable portions, and oligonucleotide link elements. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, fewer mismatches may be tolerated in a composition comprising DNA from an entire genome than a composition in which fewer DNA sequences are present. For example, in certain embodiments, with a given number of mismatches, a probe may more likely hybridize to undesired sequences in a composition with the entire genomic DNA than in a composition with fewer DNA sequences, when the same hybridization conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, primers, primer-specific portions, target-specific portions, addressable portions, and oligonucleotide link elements.

In certain embodiments, the term "to a measurably lesser extent" encompasses situations in which the event in question is reduced at least 10 fold. In certain embodiments, the term "to a measurably lesser extent" encompasses situations in which the event in question is reduced at least 100 fold.

In certain embodiments, a statement that a component may be, is, or has been "substantially removed" means that at least 90% of the component may be, is, or has been removed. In certain embodiments, a statement that a component may be, is, or has been "substantially removed" means that at least 95% of the component may be, is, or has been removed.

B. Certain Components

In certain embodiments, target nucleic acid sequences may include RNA and DNA. Exemplary RNA target sequences include, but are not limited to, mRNA, rRNA, tRNA, viral RNA, and variants of RNA, such as splicing variants. Exemplary DNA target sequences include, but are not limited to, genomic DNA, plasmid DNA, phage DNA, nucleolar DNA, mitochondrial DNA, and chloroplast DNA.

In certain embodiments, target nucleic acid sequences include, but are not limited to, cDNA, yeast artificial chromosomes (YAC's), bacterial artificial chromosomes (BAC's), other extrachromosomal DNA, and nucleic acid analogs. Exemplary nucleic acid analogs include, but are not limited to, LNAs, PNAs, PPG's, and other nucleic acid analogs.

A variety of methods are available for obtaining a target nucleic acid sequence for use with the compositions and methods of the present invention. When the nucleic acid target is obtained through isolation from a biological matrix, certain isolation techniques include, but are not limited to, (1) organic extraction followed by ethanol precipitation, e.g., using a phenol/chloroform organic reagent (e.g., Ausubel et al., eds., *Current Protocols in Molecular Biology Volume* 1, Chapter 2, Section I, John Wiley & Sons, New York (1993)), in certain embodiments, using an automated DNA extractor, e.g., the Model 341 DNA Extractor available from Applied Biosystems (Foster City, Calif.); (2) stationary phase adsorption methods (e.g., Boom et al., U.S. Pat. No. 5,234,809; Walsh et al., *Biotechniques* 10(4): 506–513 (1991)); and (3) salt-induced DNA precipitation methods (e.g., Miller et al., *Nucleic Acids Research*, 16(3): 9–10 (1988)), such precipitation methods being typically referred to as "salting-out" methods. In certain embodiments, the above isolation methods may be preceded by an enzyme digestion step to help eliminate unwanted protein from the sample, e.g., digestion with proteinase K, or other like proteases. See, e.g., U.S. patent application Ser. No. 09/724,613.

In certain embodiments, a target nucleic acid sequence may be derived from any living, or once living, organism, including but not limited to prokaryote, eukaryote, plant, animal, and virus. In certain embodiments, the target nucleic acid sequence may originate from a nucleus of a cell, e.g., genomic DNA, or may be extranuclear nucleic acid, e.g., plasmid, mitrochondrial nucleic acid, various RNAs, and the like. In certain embodiments, if the sequence from the organism is RNA, it may be reverse-transcribed into a cDNA target nucleic acid sequence. Furthermore, in certain embodiments, the target nucleic acid sequence may be present in a double stranded or single stranded form.

Exemplary target nucleic acid sequences include, but are not limited to, amplification products, ligation products, transcription products, reverse transcription products, primer extension products, methylated DNA, and cleavage products. Exemplary amplification products include, but are not limited to, PCR and isothermal products.

In certain embodiments, nucleic acids in a sample may be subjected to a cleavage procedure. In certain embodiments, such cleavage products may be targets.

Different target nucleic acid sequences may be different portions of a single contiguous nucleic acid or may be on different nucleic acids. Different portions of a single contiguous nucleic acid may or may not overlap.

In certain embodiments, a target nucleic acid sequence comprises an upstream or 5' region, a downstream or 3' region, and a "pivotal nucleotide" located in the upstream region or the downstream region (see, e.g., FIG. 6). In certain embodiments, the pivotal nucleotide may be the nucleotide being detected by the probe set and may represent, for example, without limitation, a single polymorphic nucleotide in a multiallelic target locus. In certain embodiments, more than one pivotal nucleotide is present. In certain embodiments, one or more pivotal nucleotides is located in the upstream region, and one or more pivotal nucleotide is located in the downstream region. In certain embodiments, more than one pivotal nucleotide is located in the upstream region or the downstream region.

The person of ordinary skill will appreciate that while a target nucleic acid sequence is typically described as a single-stranded molecule, the opposing strand of a double-stranded molecule comprises a complementary sequence that may also be used as a target sequence.

A ligation probe set, according to certain embodiments, comprises two or more probes that comprise a target-specific portion that is designed to hybridize in a sequence-specific manner with a complementary region on a specific target nucleic acid sequence (see, e.g., probes 2 and 3 in FIG. 2). A probe of a ligation probe set may further comprise a primer-specific portion, an addressable portion, all or part of a promoter or its complement, or a combination of these additional components. In certain embodiments, any of the probe's components may overlap any other probe component(s). For example, but without limitation, the target-specific portion may overlap the primer-specific portion, the promoter or its complement, or both. Also, without limitation, the addressable portion may overlap with the target-specific portion or the primer specific-portion, or both.

In certain embodiments, at least one probe of a ligation probe set comprises the addressable portion located between the target-specific portion and the primer-specific portion (see, e.g., probe 23 in FIG. 3). In certain embodiments, the probe's addressable portion may comprise a sequence that is the same as, or is complementary to, at least a portion of a labeled probe. In certain embodiments, the probe's primer-specific portion may comprise a sequence that is the same as, or is complementary to, at least a portion of a labeled probe. In certain embodiments, the probe's addressable portion is not complementary with target sequences, primer sequences, or probe sequences other than complementary portions of labeled probes.

The sequence-specific portions of probes are of sufficient length to permit specific annealing to complementary sequences in primers, addressable portions, and targets as appropriate. In certain embodiments, the length of the addressable portions and target-specific portion are any number of nucleotides from 6 to 35. Detailed descriptions of probe design that provide for sequence-specific annealing can be found, among other places, in Diffenbach and Dveksler, PCR Primer, A Laboratory Manual, Cold Spring Harbor Press, 1995, and Kwok et al., Nucl. Acid Res. 18:999–1005 (1990).

A ligation probe set according to certain embodiments comprises at least one first probe and at least one second probe that adjacently hybridize to the same target nucleic acid sequence. According to certain embodiments, a ligation probe set is designed so that the target-specific portion of the first probe will hybridize with the downstream target region (see, e.g., probe 2 in FIG. 2) and the target-specific portion of the second probe will hybridize with the upstream target region (see, e.g., probe 3 in FIG. 2). The sequence-specific portions of the probes are of sufficient length to permit specific annealing with complementary sequences in targets and primers, as appropriate. In certain embodiments, one of the at least one first probe and the at least one second probe in a probe set further comprises an addressable portion.

Under appropriate conditions, adjacently hybridized probes may be ligated together to form a ligation product, provided that they comprise appropriate reactive groups, for example, without limitation, a free 3'-hydroxyl and 5'-phosphate group.

According to certain embodiments, some ligation probe sets may comprise more than one first probe or more than one second probe to allow sequence discrimination between target sequences that differ by one or more nucleotides (see, e.g., FIG. 7).

According to certain embodiments of the invention, a ligation probe set is designed so that the target-specific portion of the first probe will hybridize with the downstream target region (see, e.g., the first probe in FIG. 6) and the target-specific portion of the second probe will hybridize with the upstream target region (see, e.g., the second probe in FIG. 6). In certain embodiments, a nucleotide base complementary to the pivotal nucleotide, the "pivotal complement" or "pivotal complement nucleotide," is present on the proximal end of the second probe of the target-specific probe set (see, e.g., 5' end (PC) of the second probe in FIG. 6). In certain embodiments, the first probe may comprise the pivotal complement and addressable portion rather than the second probe (see, e.g., FIG. 7). The skilled artisan will appreciate that, in various embodiments, the pivotal nucleotide(s) may be located anywhere in the target sequence and that likewise, the pivotal complement(s) may be located anywhere within the target-specific portion of the probe(s). For example, according to various embodiments, the pivotal complement may be located at the 3' end of a probe, at the 5' end of a probe, or anywhere between the 3' end and the 5' end of a probe.

In certain embodiments, when the first and second probes of the ligation probe set are hybridized to the appropriate upstream and downstream target regions, and when the pivotal complement is at the 5' end of one probe or the 3' end of the other probe, and the pivotal complement is base-paired with the pivotal nucleotide on the target sequence, the hybridized first and second probes may be ligated together to form a ligation product (see, e.g., FIG. 7(2)–(3)). In the example shown in FIG. 7(2)–(3), a mismatched base at the pivotal nucleotide, however, interferes with ligation, even if both probes are otherwise fully hybridized to their respective target regions.

In certain embodiments, other mechanisms may be employed to avoid ligation of probes that do not include the correct complementary nucleotide at the pivotal complement. For example, in certain embodiments, conditions may be employed such that a probe of a ligation probe set will hybridize to the target sequence to a measurably lesser extent if there is a mismatch at the pivotal nucleotide. Thus, in such embodiments, such non-hybridized probes will not be ligated to the other probe in the probe set.

In certain embodiments, the first probes and second probes in a ligation probe set are designed with similar melting temperatures ($T_m$). Where a probe includes a pivotal complement, in certain embodiments, the $T_m$ for the probe(s) comprising the pivotal complement(s) of the target pivotal nucleotide sought will be approximately 4–15° C. lower than the other probe(s) that do not contain the pivotal complement in the probe set. In certain such embodiments, the probe comprising the pivotal complement(s) will also be designed with a $T_m$ near the ligation temperature. Thus, a probe with a mismatched nucleotide will more readily dissociate from the target at the ligation temperature. The ligation temperature, therefore, in certain embodiments provides another way to discriminate between, for example, multiple potential alleles in the target.

Further, in certain embodiments, ligation probe sets do not comprise a pivotal complement at the terminus of the first or the second probe (e.g., at the 3' end or the 5' end of the first or second probe). Rather, the pivotal complement is located somewhere between the 5' end and the 3' end of the first or second probe. In certain such embodiments, probes with target-specific portions that are fully complementary with their respective target regions will hybridize under high stringency conditions. Probes with one or more mismatched bases in the target-specific portion, by contrast, will hybridize to their respective target region to a measurably lesser extent. Both the first probe and the second probe must be hybridized to the target for a ligation product to be generated.

In certain embodiments, highly related sequences that differ by as little as a single nucleotide can be distinguished. For example, according to certain embodiments, one can distinguish the two potential alleles in a biallelic locus as follows. One can combine a ligation probe set comprising two first probes, differing in their addressable portions and their pivotal complement (see, e.g., probes A and B in FIG. 7(1)), one second probe (see, e.g., probe Z in FIG. 7(1)), and the sample containing the target. All three probes will hybridize with the target sequence under appropriate conditions (see, e.g., FIG. 7(2)). Only the first probe with the hybridized pivotal complement, however, will be ligated with the hybridized second probe (see, e.g., FIG. 7(3)). Thus, if only one allele is present in the sample, only one ligation product for that target will be generated (see, e.g., ligation product A-Z in FIG. 7(D)). Both ligation products would be formed in a sample from a heterozygous individual. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide.

Many different signal moieties may be used in various embodiments of the present invention. For example, signal moieties include, but are not limited to, fluorophores, radioisotopes, chromogens, enzymes, antigens, heavy metals, dyes, phosphorescence groups, chemiluminescent groups, and electrochemical detection moieties. Exemplary fluorophores that may be used as signal moieties include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™ (all available from Applied Biosystems, Foster City, Calif.) Exemplary radioisotopes include, but are not limited to, $^{32}$P, $^{33}$P, and $^{35}$S. Signal moieties also include elements of multi-element indirect reporter systems, e.g., biotin/avidin, antibody/antigen, ligand/receptor, enzyme/substrate, and the like, in which the element interacts with other elements of the system in order to effect a detectable signal. Certain exemplary multi-element systems include a biotin reporter group attached to a probe and an avidin conjugated with a fluorescent label. Detailed protocols for methods of attaching signal moieties to oligonucleotides can be found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000).

As discussed above, the term "interaction probe" refers to a probe that comprises at least two moieties that can interact with one another to provide a detectably different signal value depending upon whether a given nucleic acid sequence is present or absent. In certain embodiments, one of the moieties is a signal moiety and the other moiety is a quencher moiety. The signal value that is detected from the signal moiety is different depending on whether the quencher moiety is sufficiently close to the signal moiety or is spaced apart from the signal moiety. In certain embodiments, the quencher moiety decreases the detectable signal value from the signal moiety when the quencher moiety is sufficiently close to the signal moiety. In certain embodiments, the quencher moiety decreases the detectable signal value to zero or close to zero when the quencher moiety is sufficiently close to the signal moiety.

In certain embodiments, one of the moieties of the interaction probe is a signal moiety and the other moiety is a donor moiety. The signal value that is detected from the signal moiety is different depending on whether the donor moiety is sufficiently close to the signal moiety or is spaced apart from the signal moiety. In certain embodiments, the donor moiety increases the detectable signal value from the signal moiety when the donor moiety is sufficiently close to the signal moiety. In certain embodiments, the detectable signal value is zero or close to zero when the donor moiety is not sufficiently close to the signal moiety.

In certain embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of certain such combinations of a donor and an acceptor have also been called FRET (Fluorescent Resonance Energy Transfer).

In certain embodiments, the moieties of the interaction probe are linked to one another by a link element such as, but not limited to, an oligonucleotide. In certain such embodiments, the presence of a sequence that hybridizes to a interaction probe impacts the proximity of the moieties to one another during the methods described herein. In various embodiments, the moieties may be attached to the link element in various ways known in the art. For example, certain nonlimiting protocols for attaching moieties to oligonucleotides are found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000). In certain embodiments, an interaction probe comprises more than one signal moiety. In certain embodiments, an interaction probe comprises more than one quencher moiety. In certain embodiments, an interaction probe comprises more than one donor moiety.

According to certain embodiments, the interaction probe may be a "5'-nuclease probe," which comprises a signal moiety linked to a quencher moiety or a donor moiety through a short oligonucleotide link element. When the 5'-nuclease probe is intact, the quencher moiety or the donor moiety influences the detectable signal from the signal moiety. According to certain embodiments, the 5'-nuclease probe binds to a specific nucleic acid sequence, and is cleaved by the 5' nuclease activity of at least one of a polymerase and another enzymatic construct when the probe is replaced by a newly polymerized strand during an amplification reaction such as PCR or some other strand displacement protocol.

When the oligonucleotide link element of the 5'-nuclease probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

Figure 1A:
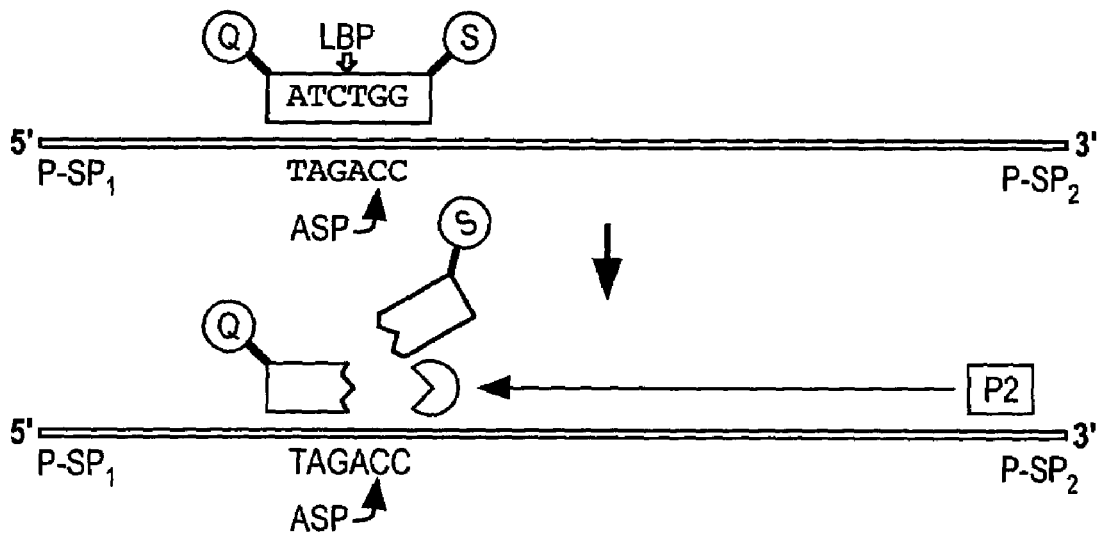

An example of a 5' nuclease probe according to certain embodiments is depicted in FIG. 1A, where the labeled probe (LBP) includes a quencher moiety (Q) and a signal moiety (S). The nucleic acid sequence with which the interaction probe interacts in FIG. 1A includes a 5' primer-specific portion P-SP1, an addressable portion (ASP), and a 3' primer-specific portion (P-SP2). The signal that is detected from the labeled probe increases with cleavage.

In certain embodiments, the 5'-nuclease probe is a 5'-nuclease fluorescent probe, in which the signal moiety is a fluorescent moiety and the quencher moiety is a fluorescence quencher moiety. When the probe is cleaved during a strand displacement protocol, the fluorescent moiety emits a detectable fluorescent signal. In certain embodiments, a 5'-nuclease fluorescent probe may emit a given level of signal when it is hybridized to a complementary sequence prior to cleavage, and the level of the signal is increased with cleavage. Certain exemplary embodiments of 5'-nuclease fluorescent probes are described, e.g., in U.S. Pat. No. 5,538,848, and exemplified by the TaqMan® probe molecule, which is part of the TaqMan® assay system (available from Applied Biosystems, Foster City, Calif.).

According to certain embodiments, the interaction probe may be a "hybridization dependent probe," which comprises a signal moiety linked to a quencher moiety or a donor moiety through an oligonucleotide link element. When the hybridization dependent probe is not bound to a given nucleic acid sequence, and is thus single stranded, the oligonucleotide link element can bend flexibly, and the quencher moiety or the donor moiety is sufficiently close to the signal moiety to influence the detectable signal from the signal moiety. In certain embodiments, the oligonucleotide link element of a hybridization dependent probe is designed such that when it is not hybridized to a given nucleic acid sequence, it folds back and hybridizes to itself (see, e.g., FIG. 1C), e.g., a molecular beacon probe. See, e.g., U.S. Pat. Nos. 5,118,801; 5,312,728; and 5,925,517. In certain embodiments, the oligonucleotide link element of a hybridization dependent probe does not hybridize to itself when it is not hybridized to the given nucleic acid sequence (see, e.g., FIG. 1B).

When a hybridization dependent probe is bound to a given nucleic acid as double stranded nucleic acid, the quencher moiety or the donor moiety is spaced apart from the signal moiety such that the detectable signal is changed. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

Figure 1B:
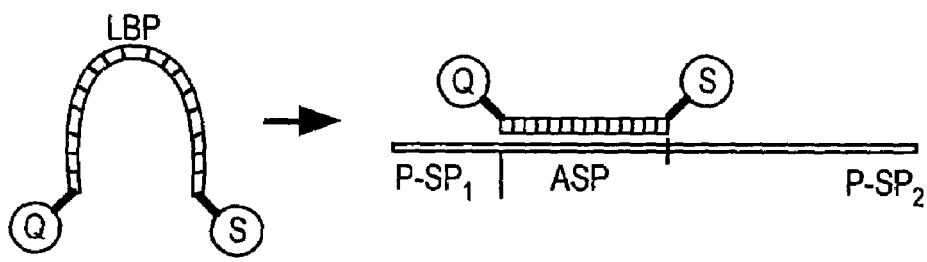
Figure 1C:
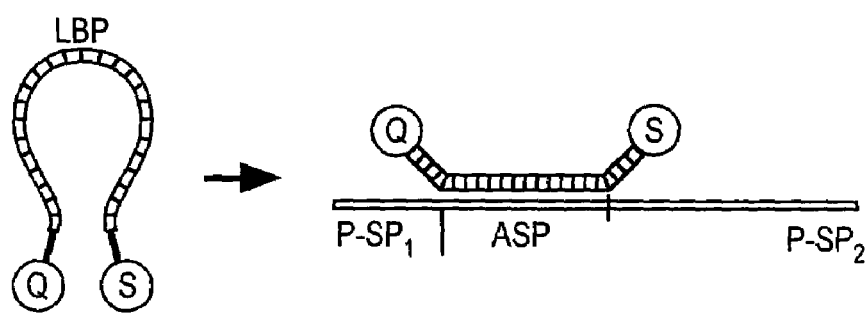

Examples of certain hybridization dependent probes according to certain embodiments are depicted in FIGS. 1B and 1C, where the labeled probe (LBP) includes a quencher moiety (Q) and a signal moiety (S). The nucleic acid sequence with which the interaction probe interacts in FIGS. 1B and 1C includes a 5' primer-specific portion P-SP1, an addressable portion (ASP), and a 3' primer-specific portion (P-SP2).

In certain embodiments of hybridization dependent probes, the signal moiety is a fluorescent moiety and the quencher moiety is a fluorescence quencher moiety. When the probe is hybridized to a specific nucleic acid sequence, the fluorescent moiety emits a detectable fluorescent signal. When the probe is not hybridized to a nucleic acid sequence and is intact, quenching occurs and little or no fluorescence is detected.

Certain exemplary embodiments of hybridization dependent probes are described, e.g., in U.S. Pat. No. 5,723,591.

In certain embodiments, one employs nucleic acids in the hybridization dependent probes such that a substantial portion of the hybridization dependent probes are not cleaved by an enzyme during an amplification reaction. A "substantial portion of the hybridization dependent probes are not cleaved" refers to a portion of the total number of hybridization dependent probes that are designed to hybridize to a given nucleic sequence that is being amplified, and it does not refer to a portion of an individual probe. In certain embodiments, "a substantial portion of hybridization dependent probes that are not cleaved" means that at least 90% of the hybridization dependent probes are not cleaved. In certain embodiments, at least 95% of the hybridization dependent probes are not cleaved. In certain embodiments, one employs PNA for some or all of the nucleic acids of a hybridization dependent probe.

In certain embodiments, one employs hybridization dependent probes in which a substantial portion of the hybridization dependent probes do not hybridize to an addressable portion or a complement of the addressable portion during an extension reaction. A "substantial portion of the hybridization dependent probes do not hybridize" here refers to a portion of the total number of hybridization dependent probes that are designed to hybridize to a given nucleic sequence that is being amplified, and it does not refer to a portion of an individual probe. In certain embodiments, "a substantial portion of hybridization dependent probes that do not hybridize" means that at least 90% of the hybridization dependent probes do not hybridize. In certain embodiments, at least 95% of the hybridization dependent probes do not hybridize.

According to certain embodiments, the interaction probe may be a "cleavable RNA probe," which comprises a signal moiety linked to a quencher moiety or a donor moiety through a short RNA link element. When the cleavable RNA probe is intact, the quencher moiety or the donor moiety influences the detectable signal from the signal moiety. According to certain embodiments, the cleavable RNA probe binds to a specific DNA sequence, and is cleaved by RNase H, or an agent with similar activity.

When the RNA link element of the cleavable RNA probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, if a particular nucleic acid sequence that is to be detected is present in a sample, a nucleic acid amplification procedure results in more DNA comprising the specific DNA sequence to which a cleavable RNA probe binds than if the particular nucleic acid sequence is not present in the sample. In such embodiments, one may determine the presence of the particular nucleic acid in the sample in view of the signal generated from the cleavable RNA probe during and/or after the amplification procedure. In certain embodiments, one may quantitate the amount of a particular nucleic acid in a sample in view of the signal generated from a cleavable RNA probe during and/or after the amplification procedure.

In certain embodiments, the cleavable RNA probe is a cleavable RNA fluorescent probe, in which the signal moiety is a fluorescent moiety and the quencher moiety is a fluorescence quencher moiety. When the probe is cleaved, the fluorescent moiety emits a detectable fluorescent signal. In certain embodiments, a cleavable RNA probe may emit a given level of signal when it is hybridized to a complementary sequence prior to cleavage, and the level of the signal is increased with cleavage.

According to certain embodiments, the interaction probe may be a "structure-specific nuclease probe," which comprises a signal moiety linked to a quencher moiety or a donor moiety through a short oligonucleotide link element. When the structure-specific nuclease probe is intact, the quencher moiety or the donor moiety influences the detectable signal from the signal moiety. According to certain embodiments, the structure-specific nuclease probe binds to a specific nucleic acid sequence, and is cleaved by a structure-specific nuclease if it is appropriately hybridized to the specific nucleic acid sequence.

When the oligonucleotide link element of the structure-specific nuclease probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, the structure-specific nuclease probe is a structure-specific nuclease fluorescent probe, in which the signal moiety is a fluorescent moiety and the quencher moiety is a fluorescence quencher moiety. When the probe is cleaved, the fluorescent moiety emits a detectable fluorescent signal. In certain embodiments, a structure-specific nuclease probe may emit a given level of signal when it is hybridized to a complementary sequence prior to cleavage, and the level of the signal is increased with cleavage.

In certain embodiments, one employs a structure-specific nuclease probe comprising a flap that does not substantially hybridize to the addressable portion and employs a flap endonuclease (FEN) as the structure-specific nuclease. An exemplary embodiment is shown in FIG. 19. The structure-specific nuclease probe in FIG. 19 includes a flap portion that does not hybridize to the addressable portion, a hybridizing portion that hybridizes to the addressable portion, and a FEN cleavage position nucleotide between the flap portion and the hybridizing portion. The FEN cleavage position nucleotide is designed to be complementary to the nucleotide of the addressable portion that is immediately 3' to the nucleotide that hybridizes to the 5' end nucleotide of the probe's hybridizing portion. The flap portion includes a signal moiety attached to it and the hybridizing portion includes a quencher moiety or a donor moiety attached to it.

As shown in the embodiments depicted in FIG. 19, another oligonucleotide X is designed to hybridize to the addressable portion 3' to the portion of the addressable portion that hybridizes to the hybridizing portion of the structure-specific nuclease probe. If the appropriate addressable portion is present, FEN will cleave the structure-specific nuclease probe such that the signal moiety becomes separated from the quenching moiety or donor moiety.

According to certain embodiments, the interaction probe may comprise two oligonucleotides that hybridize to a given nucleic acid sequence adjacent to one another. In certain embodiments, one of the oligonucleotides comprises a signal moiety and one of the oligonucleotides comprises a quencher moiety or a donor moiety. When both oligonucleotides are hybridized to the given nucleic acid sequence, the quencher moiety or the donor moiety is sufficiently close to the signal moiety to influence the detectable signal from the signal moiety.

In certain such embodiments that employ a donor moiety, the signal value increases when the two oligonucleotides are hybridized to the given nucleic acid sequence. In certain such embodiments that employ a quencher moiety, the signal value decreases when the two oligonucleotides are hybridized to the given nucleic acid sequence. In certain embodiments, the signal moiety is a fluorescent moiety.

Other examples of suitable labeled probes according to certain embodiments are i-probes, scorpion probes, eclipse probes, and others. Exemplary, but nonlimiting, probes are discussed, for example, in Whitcombe et al., Nat. Biotechnol., 17(8):804–807 (1999) (includes scorpion probes); Thelwell et al., Nucleic Acids Res., 28(19):3752–3761 (2000) (includes scorpion probes); Afonina et al., Biotechniques, 32(4): (2002) (includes eclipse probes); Li et al., "A new class of homogeneous nucleic acid probes based on specific displacement hybridization", Nucleic Acids Res., 30(2):E5 (2002); Kandimall et al., Bioorg. Med. Chem., 8(8):1911–1916 (2000); Isacsson et al., Mol. Cell. Probes, 14(5):321–328 (2000); French et al, Mol. Cell. Probes, 15(6):363–374 (2001); and Nurmi et al., "A new label technology for the detection of specific polymerase chain reaction products in a closed tube", Nucleic Acids Res., 28(8), E28 (2000). Exemplary quencher moieties according to certain embodiments may be those available from Epoch Biosciences, Bothell, Wash.

In certain embodiments, one may use a labeled probe and a threshold difference between first and second detectable signal values to detect the presence or absence of a target nucleic acid in a sample. In such embodiments, if the difference between the first and second detectable signal values is the same as or greater than the threshold difference, i.e., there is a threshold difference, one concludes that the target nucleic acid is present. If the difference between the first and second detectable signal values is less than the threshold difference, i.e., there is no threshold difference, one concludes that the target nucleic acid is absent.

Certain nonlimiting examples of how one may set a threshold difference according to certain embodiments follow.

First, in certain embodiments, a labeled probe that is not hybridized to a complementary sequence may have a first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain such embodiments, when such an amplification reaction composition does not include any ligation products comprising the complementary addressable portion, the detectable signal value may remain at 0.4 during and/or after an amplification reaction. (In other words, the second detectable signal value is 0.4.) In certain such embodiments, when such an amplification reaction composition, however, includes a ligation product comprising a complementary addressable portion, the detectable signal value may increase to 2 during and/or after an amplification reaction. (In other words, the second detectable signal value is 2.)

Thus, in certain such embodiments, one may set a threshold difference between first and second detectable signal values at a value somewhere between a value just above 0.4 to about 2. For example, one may set the threshold difference at somewhere between 0.5 to 2.

Second, in certain embodiments, a labeled probe that is not hybridized to a complementary sequence may have an first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain such embodiments, when such an amplification reaction composition does not include any ligation products comprising the complementary addressable portion, the detectable signal value may increase to 0.7 during and/or after an amplification reaction. (In other words, the second detectable signal value is 0.7.) In certain such embodiments, when such an amplification reaction composition, however, includes a ligation product comprising a complementary addressable portion, the detectable signal value may increase to 2 during and/or after an amplification reaction. (In other words, the second detectable signal value is 2.)

Thus, in certain such embodiments, one may set a threshold difference between first and second detectable signal values at a value somewhere between a value just above 0.7 to about 2. For example, one may set the threshold difference at somewhere between 0.8 to 2.

Third, in certain embodiments, a labeled probe that is not hybridized to a complementary sequence may have a first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain such embodiments, when such an amplification reaction composition does not include any ligation products comprising the complementary addressable portion, the detectable signal value may increase linearly during and/or after an amplification reaction. (In other words, the second detectable signal value is linearly increased from the first detectable signal value.) In certain such embodiments, when such an amplification reaction composition, however, includes a ligation product comprising a complementary addressable portion, the detectable signal value may increase exponentially during and/or after an amplification reaction. (In other words, the second detectable signal value is exponentially increased from the first detectable signal value.)

Thus, in certain such embodiments, one may measure detectable signal values at two or more points during amplification, and at the end of the amplification reaction, to determine if the increase in detectable signal value is linear or exponential. In certain embodiments, one may measure detectable signal values at three or more points during amplification to determine if the increase in detectable signal value is linear or exponential. In certain embodiments, if the increase is exponential, there is a threshold difference between the first and second detectable signal values.

In certain embodiments, one may employ a ligation probe set that can be used in a FEN-OLA technique. In a FEN-OLA technique, a first probe of a ligation probe set comprises a target-specific portion that is designed to hybridize to the target nucleic acid sequence. A second probe of the ligation probe set comprises a flap portion, a target-specific portion, and a FEN cleavage position nucleotide between the flap portion and the target-specific portion. The target-specific portion of the second probe is designed to hybridize to the target nucleic acid sequence such the end of the target-specific portion nearest the flap portion is adjacent to the hybridized target-specific portion of the first probe.

The flap portion is designed such that a substantial portion of the flap portions do not hybridize to the target nucleic acid sequence. A "substantial portion of the flap portions do not hybridize" refers to a portion of the total number of flap portions, and it does not refer to a portion of an individual flap portion. In certain embodiments, "a substantial portion of flap portions that do not hybridize" means that at least 90% of the flap portions do not hybridize. In certain embodiments, at least 95% of the flap portions do not hybridize.

FEN will cleave the second probe between the cleavage position nucleotide and the target-specific portion, if the proper target nucleic acid sequence is present. Specifically, such cleavage occurs if the target-specific portions of the first and second probes hybridize to the target nucleic acid sequence, and the FEN cleavage position nucleotide is complementary to the nucleotide of the target nucleic acid sequence that is directly adjacent to the portion of the target nucleic sequence that hybridizes to the target specific portion of the second probe. FIG. 15 shows certain nonlimiting examples that help to illustrate certain ligation probe sets that may be used in FEN-OLA techniques according to certain embodiments.

If the flap is cleaved, the second probe may then be ligated to the adjacent hybridized first probe of a ligation probe set. If the flap is not cleaved, the second probe will not be ligated to the adjacent hybridized first probe.

Figure 16A:
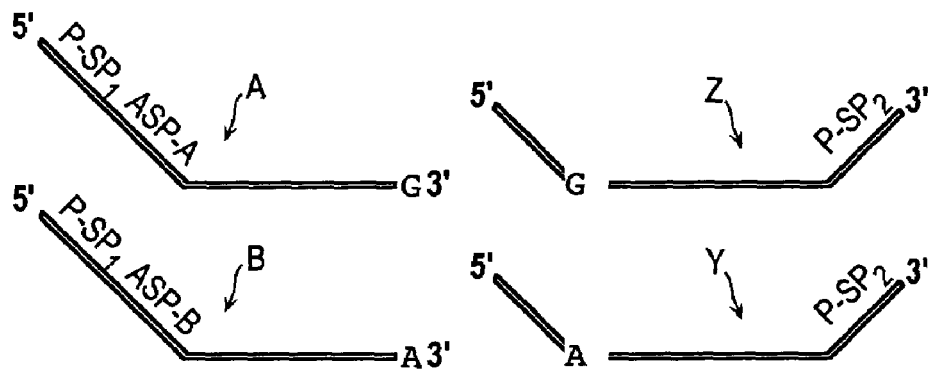

Certain nonlimiting examples of probes used in a FEN-OLA technique are depicted in FIG. 16. In FIG. 16, one employs a probe set comprising: two first probes, differing in their addressable portions and their pivotal complements (see, e.g., probes A and B in FIG. 16(A)); and two second probes that comprise different FEN cleavage position nucleotides that correspond to the pivotal complements of the two first probes (see, e.g., probes Y and Z in FIG. 16(A)).

Figure 16B:
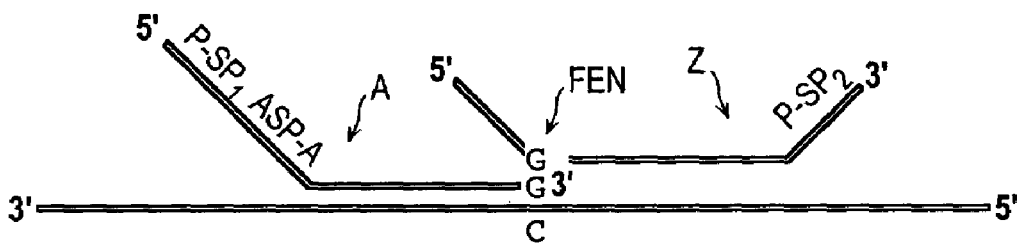
Figure 16C:
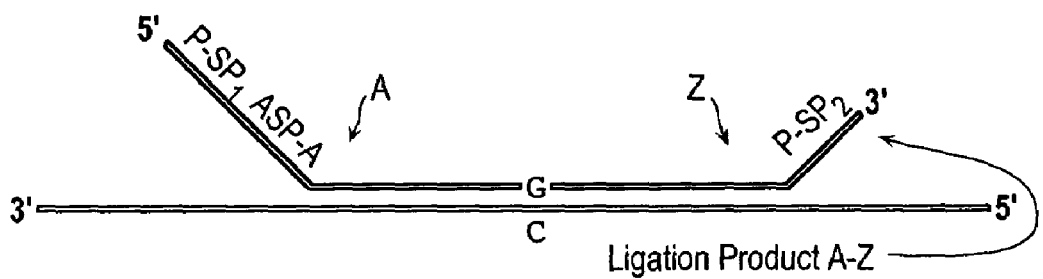

In the embodiment shown in FIG. 16, FEN will cleave the flap of a second probe only if the second probe comprises a FEN cleavage position nucleotide that is complementary to the pivotal nucleotide of target nucleic acid sequence (see, e.g., FIG. 16(B)). In such a situation in such embodiments, the first and second probes of the probe set are ligated together if the pivotal complement of the first probe is complementary to the pivotal nucleotide of the target nucleic acid sequence (see, e.g., FIG. 16(C)). If there is a mismatch at the pivotal nucleotide, no ligation occurs.

Thus, if only one allele is present in the sample, only one ligation product for that target will be generated (see, e.g., ligation product A-Z in FIG. 16(C)). Both ligation products would be formed in a sample from a heterozygous individual. In certain embodiments, cleavage of probes with a FEN cleavage position nucleotide that is not complementary to the pivotal nucleotide may occur, but such cleavage occurs to a measurably lesser extent than cleavage of probes with a FEN cleavage position nucleotide that is complementary to the pivotal nucleotide. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide.

Figure 17A:
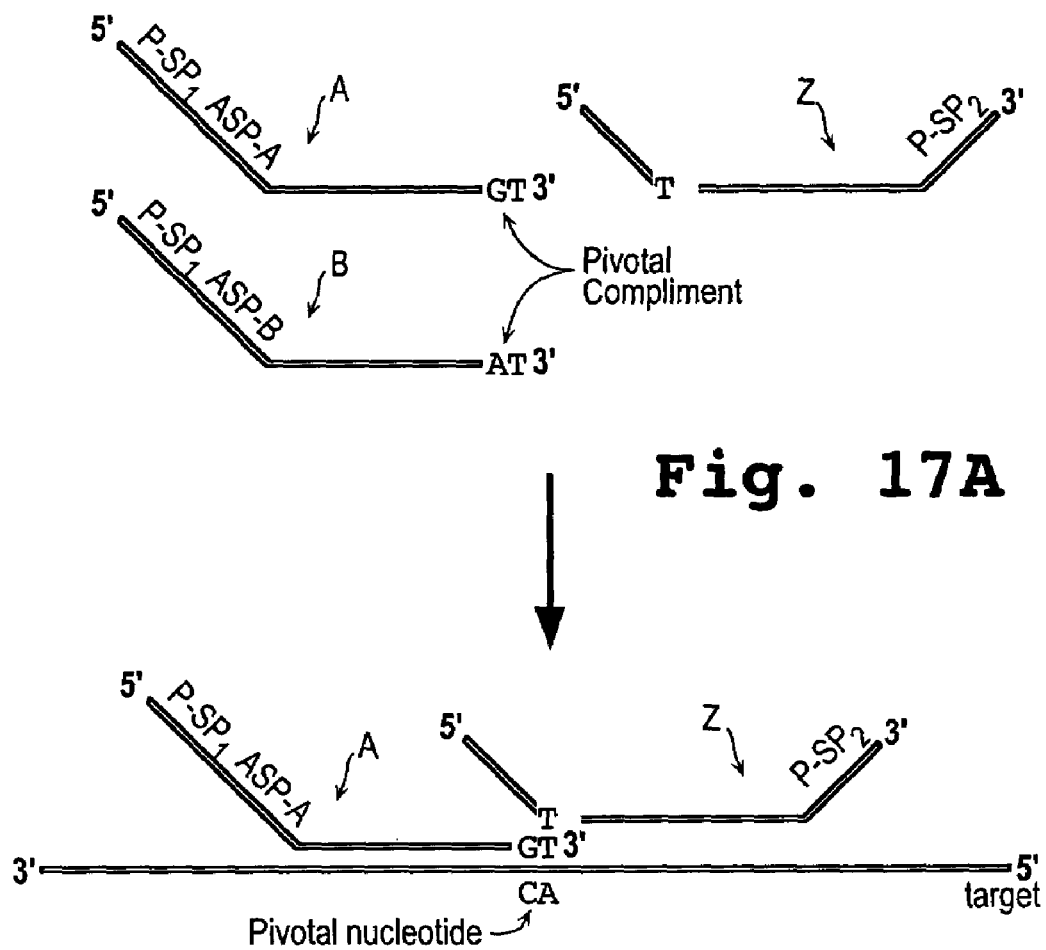
Figure 17B:
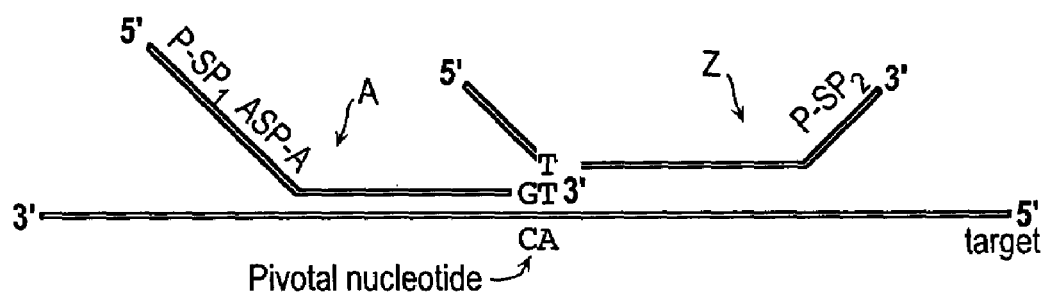

Certain nonlimiting examples of probes used in a FEN-OLA technique are also depicted in FIG. 17. In FIG. 17, one employs a probe set comprising two first probes, which comprise different addressable portions and different pivotal complements and the pivotal complement of each first probe is at the penultimate nucleotide position at the 3' end of the first probes (see, e.g., probes A and B in FIG. 17(A)). The probe set further comprises a second probe that comprises a FEN cleavage position nucleotide that is the same as the nucleotide at the 3' end of the two first probes (see, e.g., probe Z in FIG. 17(A)).

a. In the embodiment depicted in FIG. 17, FEN will cleave the flap of a second probe only if the second probe comprises a FEN cleavage position nucleotide that is complementary to the nucleotide immediately 5' of the pivotal nucleotide of target nucleic acid sequence (see, e.g., FIG. 17(B)). In such a situation in such embodiments, the first and second probes of the probe set are ligated together if: (1) the pivotal complement of the first probe is complementary to the pivotal nucleotide of the target nucleic acid sequence; and (2) the nucleotide at the 3' end of the first probe is complementary to the nucleotide immediately 5' of the pivotal nucleotide of target nucleic acid sequence (see, e.g., FIG. 17(C)). If there is a mismatch at the pivotal nucleotide, no ligation occurs.

Figure 17C:
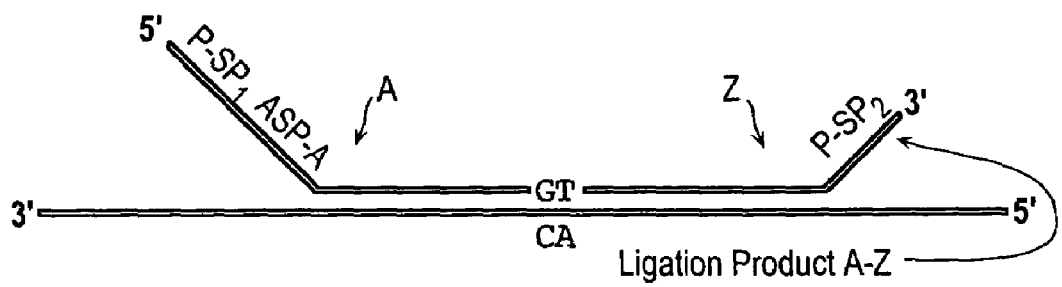

Thus, if only one allele is present in the sample, only one ligation product for that target will be generated (see, e.g., ligation product A-Z in FIG. 17(C)). Both ligation products would be formed in a sample from a heterozygous individual. In certain embodiments, cleavage of probes with a FEN cleavage position nucleotide that is not complementary to the nucleotide immediately 5' of the pivotal nucleotide may occur, but such cleavage occurs to a measurably lesser extent than cleavage of probes with a FEN cleavage position nucleotide that is complementary to the nucleotide immediately 5' of the pivotal nucleotide. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide. In certain embodiments, ligation of first probes with a nucleotide at the 3' end that is not complementary to the nucleotide immediately 5' of the pivotal nucleotide may occur, but such ligation occurs to a measurably lesser extent than ligation of first probes with a nucleotide at the 3' end that is complementary to the nucleotide immediately 5' of the pivotal nucleotide.

Figure 18A:
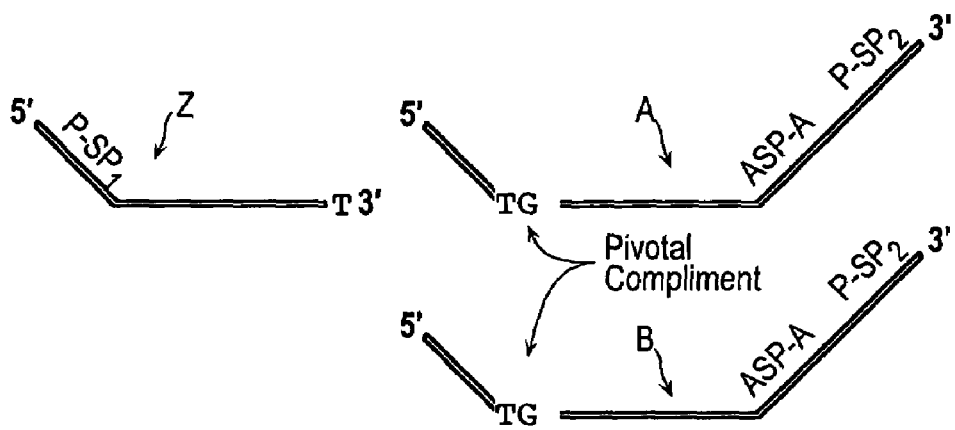

Certain nonlimiting examples of probes used in a FEN-OLA technique are also depicted in FIG. 18. In FIG. 18, one employs a probe set comprising two second probes, which comprise the same FEN cleavage position nucleotide and comprise different addressable portions and different pivotal complements (the pivotal complement of each second probe is immediately 3' to the FEN cleavage position nucleotide) (see, e.g., probes A and B in FIG. 18(A)). The probe set further comprises a first probe that comprises a nucleotide at the 3' end that is the same as the FEN cleavage position nucleotide (see, e.g., probe Z in FIG. 18(A)).

Figure 18B:
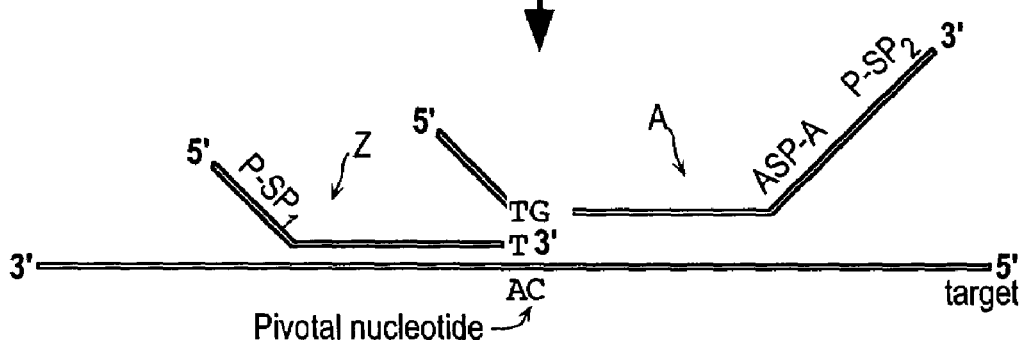
Figure 18C:
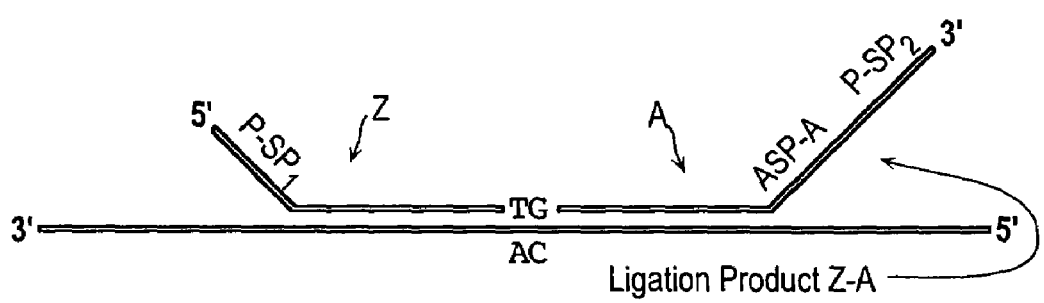

In the embodiment depicted in FIG. 18, FEN will cleave the flap of a second probe only if the second probe comprises a FEN cleavage position nucleotide that is complementary to the nucleotide immediately 3' of the pivotal nucleotide of target nucleic acid sequence (see, e.g., FIG. 18(B)). In such a situation in such embodiments, the first and second probes of the probe set are ligated together if: (1) the pivotal complement of the second probe is complementary to the pivotal nucleotide of the target nucleic acid sequence; and (2) the nucleotide at the 3' end of the first probe is complementary to the nucleotide immediately 3' of the pivotal nucleotide of target nucleic acid sequence (see, e.g., FIG. 18(C)). If there is a mismatch at the pivotal nucleotide, no ligation occurs.

Thus, if only one allele is present in the sample, only one ligation product for that target will be generated (see, e.g., ligation product Z-A in FIG. 18(C)). Both ligation products would be formed in a sample from a heterozygous individual. In certain embodiments, cleavage of probes with a FEN cleavage position nucleotide that is not complementary to the nucleotide immediately 3' of the pivotal nucleotide may occur, but such cleavage occurs to a measurably lesser extent than cleavage of probes with a FEN cleavage position nucleotide that is complementary to the nucleotide immediately 3' of the pivotal nucleotide. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide. In certain embodiments, ligation of first probes with a nucleotide at the 3' end that is not complementary to the nucleotide immediately 3' of the pivotal nucleotide may occur, but such ligation occurs to a measurably lesser extent than ligation of first probes with a nucleotide at the 3' end that is complementary to the nucleotide immediately 3' of the pivotal nucleotide.

In certain embodiments, one may employ different labeled probes that are specific to different addressable portions. In certain such embodiments, one may employ different labeled probes that comprise different sequences and detectably different signal moieties. Detectably different signal moieties include, but are not limited to, moieties that emit light of different wavelengths, moieties that absorb light of different wavelengths, moieties that have different fluorescent decay lifetimes, moieties that have different spectral signatures, and moieties that have different radioactive decay properties.

In certain embodiments, one may employ a labeled probe that remains intact unless a particular nucleic acid sequence is present. A label is attached to the probe. If the particular nucleic acid is present, the probe will be cleaved. Certain examples, of such probes include, but are not limited to, probes that are cleaved by 5' nuclease activity during an extension reaction, probes that are cleaved by structure-specific nuclease activity and probes that are cleaved by RNase H or another agent with similar activity.

In certain such embodiments, the cleaved portion of the probe with the label can be separated from intact probes in view of different migration rates of the cleaved portion of the probe and the intact probe using a method such as a "mobility-dependent analysis technique." A "mobility-dependent analysis technique" refers to any analysis based on different rates of migration between different analytes. Exemplary mobility-dependent analyse techniques include, but are not limited to, electrophoresis, mass spectroscopy, chromatography, sedimentation, gradient centrifugation, field-flow fractionation, and multi-stage extraction techniques. Thus, in such embodiments, one may determine the presence or absence of (or quantitate) a particular nucleic acid sequence in a sample by detecting the presence of (or quantitating) labeled cleaved portions of the labeled probe.

In certain embodiments, one may employ a mobility modifier to separate different cleaved portions of labeled probes from one another. For example, in certain such embodiments, different labeled probes with the same label could be used for different loci if the labeled probes for each different loci had a different mobility modifier. In certain embodiments, mobility modifiers may be oligonucleotides of different lengths effecting different mobilities. In certain embodiments, mobility modifiers may also be non-nucleotide polymers, such as a polyethylene oxide (PEO), polyglycolic acid, polyurethane polymers, polypeptides, or oligosaccharides, as non-limiting examples. In certain embodiments, mobility modifiers may work by adding size to a polynucleotide, or by increasing the "drag" of the molecule during migration through a medium without substantially adding to the size. Certain mobility modifiers such as PEO's have been described, e.g., in U.S. Pat. Nos. 5,470,705; 5,580,732; 5,624,800; and 5,989,871.

In certain embodiments, one may create a library of all, or a subset of all, possible combinations of nucleotides for one probe of a ligation probe set. For example, in certain embodiments, one may create a library of probes from which one may select two allele specific probes to detect any single nucleotide polymorphism in any nucleic acid sequence.

In certain embodiments, one creates a library that includes an allele specific probe for every possible nucleotide combination of a target-specific portion of a given number of nucleotides. Since there are four possible nucleotides for each of the given number of nucleotides, there are $4^X$ possible combinations for a given number X nucleotides. Thus, in certain such embodiments, $4^X$ allele specific probes are provided in the library so that one may select a probe for every possible combination of X number of nucleotides in the target-specific portion of the probe.

In certain embodiments, each of the allele specific probes of the library will further comprise a primer-specific portion and an addressable portion between the primer-specific portion and the target-specific portion. In certain embodiments, all of the probes will have the same primer-specific portion.

In certain embodiments, to detect or quantitate two possible alleles of a biallelic locus, one can make a library of $[4^{(X-1)} \times 6]$ probes from which one can choose two allele specific probes to distinguish between each of the possible two alleles for every possible combination of X nucleotides in the target-specific portion of the probe.

For example, in certain such embodiments, the target-specific portion of the allele specific probes of the library are six nucleotides in length. In certain such embodiments, the library will include probes with addressable portion AP1 and will include other probes with a different addressable portion AP2. To aid in the following discussion of certain embodiments, Table A is provided.

TABLE A

| AP1-N$_5$A ($4^5$ = 1024 probes) | AP2-N$_5$C ($4^5$ = 1024 probes) |
| AP1-N$_5$C ($4^5$ = 1024 probes) | AP2-N$_5$G ($4^5$ = 1024 probes) |
| AP1-N$_5$G ($4^5$ = 1024 probes) | AP2-N$_5$T ($4^5$ = 1024 probes) |

In embodiments as depicted in Table A, the library includes allele specific probes that comprise AP1 and each of the possible combinations of six nucleotide long target-specific portions that have "A" as the pivotal complement. Since all such probes have "A" as the pivotal complement, the combination of 5 nucleotide positions (N$_5$) of each target-specific portion will be different in each different probe, and thus, there will be $4^5$=1024 different probes in the library that comprise AP1 and "A" as the pivotal complement.

In embodiments as depicted in Table A, the library includes allele specific probes that comprise AP1 and each of the possible combinations of six nucleotide long target-specific portions that have "C" as the pivotal complement. Since all such probes have "C" as the pivotal complement, the combination of 5 nucleotide positions (N$_5$) of each target-specific portion will be different in each different probe, and thus, there will be $4^5$=1024 different probes in the library that comprise AP1 and "C" as the pivotal complement.

In embodiments as depicted in Table A, the library includes allele specific probes that comprise AP1 and each of the possible combinations of six nucleotide long target-specific portions that have "G" as the pivotal complement. Since all such probes have "G" as the pivotal complement, the combination of 5 nucleotide positions (N$_5$) of each target-specific portion will be different in each different probe, and thus, there will be $4^5$=1024 different probes in the library that comprise AP1 and "G" as the pivotal complement.

In embodiments as depicted in Table A, the library includes allele specific probes that comprise AP2 and each of the possible combinations of six nucleotide long target-specific portions that have "C" as the pivotal complement. Since all such probes have "C" as the pivotal complement, the combination of 5 nucleotide positions (N$_5$) of each target-specific portion will be different in each different probe, and thus, there will be $4^5$=1024 different probes in the library that comprise AP2 and "C" as the pivotal complement.

In embodiments as depicted in Table A, the library includes allele specific probes that comprise AP2 and each of the possible combinations of six nucleotide long target-specific portions that have "G" as the pivotal complement.

Since all such probes have "G" as the pivotal complement, the combination of 5 nucleotide positions ($N_5$) of each target-specific portion will be different in each different probe, and thus, there will be $4^5=1024$ different probes in the library that comprise AP2 and "G" as the pivotal complement.

In embodiments as depicted in Table A, the library includes allele specific probes that comprise AP2 and each of the possible combinations of six nucleotide long target-specific portions that have "T" as the pivotal complement. Since all such probes have "T" as the pivotal complement, the combination of 5 nucleotide positions ($N_5$) of each target-specific portion will be different in each different probe, and thus, there will be $4^5=1024$ different probes in the library that comprise AP2 and "T" as the pivotal complement.

Thus, the library includes $[4^{(X-1)} \times 6] = [4^{(6-1)} \times 6] = [4^{(5)} \times 6] = 6144$ probes. Table B below shows certain embodiments of how one can select two probes from the library depicted in Table A for each of the possible two pivotal nucleotides at any of the possible biallelic loci.

TABLE B

| | |
|---|---|
| AP1-$N_5$A/AP2-$N_5$C | (1024 different pairs of probes - $N_5$ is the same within a given pair of probes, but each of the different 1024 pairs of probes has a different $N_5$) |
| AP1-$N_5$A/AP2-$N_5$G | (1024 different pairs of probes - $N_5$ is the same within a given pair of probes, but each of the different 1024 pairs of probes has a different $N_5$) |
| AP1-$N_5$A/AP2-$N_5$T | (1024 different pairs of probes - $N_5$ is the same within a given pair of probes, but each of the different 1024 pairs of probes has a different $N_5$) |
| AP1-$N_5$C/AP2-$N_5$G | (1024 different pairs of probes - $N_5$ is the same within a given pair of probes, but each of the different 1024 pairs of probes has a different $N_5$) |
| AP1-$N_5$C/AP2-$N_5$T | (1024 different pairs of probes - $N_5$ is the same within a given pair of probes, but each of the different 1024 pairs of probes has a different $N_5$) |
| AP1-$N_5$G/AP2-$N_5$T | (1024 different pairs of probes - $N_5$ is the same within a given pair of probes, but each of the different 1024 pairs of probes has a different $N_5$) |

Thus, one can select a pair of probes from the 6144 different pairs of probes for each possible biallelic loci.

In certain embodiments, one may change the correspondence between a given addressable portion and a given nucleotide at the pivotal complement that is shown in Table A. See, e.g., the library depicted in Table C below according to certain embodiments.

TABLE C

| | |
|---|---|
| AP1-$N_5$C ($4^5$ = 1024 probes) | AP2-$N_5$A ($4^5$ = 1024 probes) |
| AP1-$N_5$A ($4^5$ = 1024 probes) | AP2-$N_5$T ($4^5$ = 1024 probes) |
| AP1-$N_5$T ($4^5$ = 1024 probes) | AP2-$N_5$G ($4^5$ = 1024 probes) |

Table D below shows a library of allele specific probes for biallelic loci according to certain embodiments that comprise a target-specific portion that is eight nucleotides in length.

TABLE D

| | |
|---|---|
| AP1-$N_7$A ($7^4$ = 16,384 probes) | AP2-$N_7$C ($7^4$ = 16,384 probes) |
| AP1-$N_7$C ($7^4$ = 16,384 probes) | AP2-$N_7$G ($7^4$ = 16,384 probes) |
| AP1-$N_7$G ($7^4$ = 16,384 probes) | AP2-$N_7$T ($7^4$ = 16,384 probes) |

Thus, the library includes $[4^{(X-1)} \times 6] = [4^{(8-1)} \times 6] = [4^{(7)} \times 6] = 98,304$ probes. Table E below shows how one can select two probes from the library depicted in Table D for each of the possible two pivotal nucleotides at any of the possible biallelic loci.

TABLE E

| | |
|---|---|
| AP1-$N_7$A/AP2-$N_7$C | (16,384 different pairs of probes - $N_7$ is the same within a given pair of probes, but each of the different 16,384 pairs of probes has a different $N_7$) |
| AP1-$N_7$A/AP2-$N_7$G | (16,384 different pairs of probes - $N_7$ is the same within a given pair of probes, but each of the different 16,384 pairs of probes has a different $N_7$) |
| AP1-$N_7$A/AP2-$N_7$T | (16,384 different pairs of probes - $N_7$ is the same within a given pair of probes, but each of the different 16,384 pairs of probes has a different $N_7$) |
| AP1-$N_7$C/AP2-$N_7$G | (16,384 different pairs of probes - $N_7$ is the same within a given pair of probes, but each of the different 16,384 pairs of probes has a different $N_7$) |
| AP1-$N_7$C/AP2-$N_5$T | (16,384 different pairs of probes - $N_7$ is the same within a given pair of probes, but each of the different 16,384 pairs of probes has a different $N_7$) |
| AP1-$N_7$G/AP2-$N_5$T | (16,384 different pairs of probes - $N_7$ is the same within a given pair of probes, but each of the different 16,384 pairs of probes has a different $N_7$) |

Thus, one can select a pair of probes from the 16,384 different pairs of probes for each possible biallelic loci.

In certain embodiments, to detect or quantitate two possible alleles of a biallelic locus, the library may include two sets of $4^X$ probes. One set of such probes may have a first addressable portion and the other set may be identical except have a second different addressable portion. Thus, in such embodiments, all possible combinations of two allele specific probes with two different addressable portions are available.

For example, with single nucleotide polymorphisms (SNPs), assume that one identifies a particular biallelic SNP locus. In certain embodiments, one can match the two possible nucleotides of the SNP and the adjacent (X minus 1) nucleotides of the target locus to the library of probes to find two appropriate allele specific probes with two different addressable portions.

In certain embodiments, the target-specific portion of the allele specific probes of the library are six nucleotides in length. Thus, there are $4^6=4096$ possible combinations for the target-specific portions of the allele specific probes of the library. If the library includes probes with two different addressable portions for each 4096 possible target-specific portions, the library includes 8192 allele specific probes.

In certain embodiments, the target-specific portion of the allele specific probes of the library are eight nucleotides in length. Thus, there are $4^8=65,536$ possible combinations for the target-specific portions of the allele specific probes of the library. If the library includes probes with two different addressable portions for each 65,536 possible target-specific portions, the library includes 131,072 allele specific probes.

In certain embodiments, one can also make the other probe of the ligation probe set (a locus specific probe), which is the probe that will have a target-specific portion that permits it to anneal to the target adjacent to the allele specific probes. The term locus specific probe is used simply to distinguish it from the allele specific probes in the library.

In various embodiments, the number of specific nucleotides in the target-specific portion of the allele specific probes of a library may be at any point between four nucleotides and twenty nucleotides.

One skilled in the art will be able to design the probes such that ligation occurs when the locus specific probe and the appropriate allele specific probe (with a nucleotide complementary to the SNP nucleotide) hybridize adjacent to one another on the target nucleic acid sequence. In certain embodiments, one may employ LNA in the probes.

In certain embodiments, one may increase the length of the probes by including sequences that have a specific portion that is designed to hybridize to a particular target nucleic acid sequence and an adjacent degenerate portion. For example, in certain embodiments, a group of probes may all be used for a specific six nucleotide portion of a particular target nucleic acid sequence. In certain such embodiments, each of the probes in the group may comprise the same six nucleotide sequence portion that is complementary to the particular target nucleic acid sequence. The probes in the group further comprise additional adjacent degenerate portions that randomly have the four different nucleotides at each of the positions of the degenerate portion so that both the specific six nucleotide portion and the degenerate portion of at least one of the probes in the group will hybridize to any nucleic acid that includes the specific six nucleotide portion.

For example, for a given six nucleotide target nucleic acid sequence, each probe of a group of probes may include the same six nucleotide sequence portion that is complementary to the particular target nucleic acid sequence. Each of the probes of the group may further comprise a four nucleotide degenerate portion. The probes in the series may have all of the possible combinations for a four nucleotide sequence. Thus, although only six nucleotides provide specificity for the target nucleic acid sequence, one of the probes in the group will have a random four nucleotide sequence that will also hybridize to the target. Accordingly, the length of the portion of at least one probe in the group that hybridizes to the target increases to ten nucleotides rather than six nucleotides.

In certain embodiments, one may increase the length of the probe by adding a portion with universal nucleotides that will hybridize to most or all nucleotides nonspecifically. Exemplary, but nonlimiting, universal nucleotides are discussed, e.g., in Berger et al. *Angew. Chem. Int. Ed. Engl.* (2000) 39: 2940–42; and Smith et al. *Nucleosides & Nucleotides* (1998) 17: 541–554. An exemplary, but nonlimiting, universal nucleotide is 8-aza-7-deazaadenine, which is discussed, e.g., in Sella and Debelak, Nucl. Acids Res., 28:3224–3232 (2000).

In certain embodiments, one may employ universal nucleotides or degenerate portions in probes to accommodate sequence variation. In certain embodiments, one may employ universal nucleotides in probes of a library to reduce complexity of the library.

A primer set according to certain embodiments comprises at least one primer capable of hybridizing with the primer-specific portion of at least one probe of a ligation probe set. In certain embodiments, a primer set comprises at least one first primer and at least one second primer, wherein the at least one first primer specifically hybridizes with one probe of a ligation probe set (or a complement of such a probe) and the at least one second primer of the primer set specifically hybridizes with a second probe of the same ligation probe set (or a complement of such a probe). In certain embodiments, at least one primer of a primer set further comprises all or part of a promoter sequence or its complement. In certain embodiments, the first and second primers of a primer set have different hybridization temperatures, to permit temperature-based asymmetric PCR reactions.

The skilled artisan will appreciate that while the probes and primers of the invention may be described in the singular form, a plurality of probes or primers may be encompassed by the singular term, as will be apparent from the context. Thus, for example, in certain embodiments, a ligation probe set typically comprises a plurality of first probes and a plurality of second probes.

The criteria for designing sequence-specific primers and probes are well known to persons of ordinary skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (Nucl. Acid Res. 18:999–1005, 1990). The sequence-specific portions of the primers are of sufficient length to permit specific annealing to complementary sequences in ligation products and amplification products, as appropriate.

In embodiments that employ a promoter sequence, the promoter sequence or its complement will be of sufficient length to permit an appropriate polymerase to interact with it. Detailed descriptions of sequences that are sufficiently long for polymerase interaction can be found in, among other places, Sambrook and Russell.

According to certain embodiments, a primer set of the present invention comprises at least one second primer. In certain embodiments, the second primer in that primer set is designed to hybridize with a 3' primer-specific portion of a ligation or amplification product in a sequence-specific manner (see, e.g., FIG. 2C). In certain embodiments, the primer set further comprises at least one first primer. In certain embodiments, the first primer of a primer set is designed to hybridize with the complement of the 5' primer-specific portion of that same ligation or amplification product in a sequence-specific manner. In certain embodiments, at least one primer of the primer set comprises a promoter sequence or its complement or a portion of a promoter sequence or its complement. For a discussion of primers comprising promoter sequences, see, e.g., Sambrook and Russell.

A universal primer or primer set may be employed according to certain embodiments. In certain embodiments, a universal primer or a universal primer set hybridizes with two or more of the probes, ligation products, or amplification products in a reaction, as appropriate. When universal primer sets are used in certain amplification reactions, such as, but not limited to, PCR, qualitative or quantitative results may be obtained for a broad range of template concentrations.

In certain embodiments involving a ligation reaction and an amplification reaction, one may employ at least one probe and/or at least one primer that includes a minor groove binder attached to it. Certain exemplary minor groove binders and certain exemplary methods of attaching minor groove binders to oligonucleotides are discussed, e.g., in U.S. Pat. Nos. 5,801,155 and 6,084,102. Certain exemplary minor groove binders are those available from Epoch Biosciences, Bothell, Wash. According to certain embodiments, a minor groove binder may be attached to at least one of the following: at least one probe of a ligation probe set; at least one primer of a primer set; and at least one labeled probe.

According to certain embodiments, a minor groove binder is attached to a ligation probe that includes a 3' primer-specific portion. In certain such embodiments, the presence of the minor groove binder facilitates use of a short primer that hybridizes to the 3' primer-specific portion in an amplification reaction. For example, in certain embodiments, the short primer, or segment of the primer that hybridizes to the primer-specific portion or its complement, may have a length of anywhere between 8 and 15 nucleotides.

In certain embodiments, a minor groove binder is attached to at least one of a forward primer and a reverse primer to be used in an amplification reaction. In certain such embodiments, a primer with a minor groove binder attached to it may be a short primer. For example, in certain embodiments, the short primer, or segment of the primer that hybridizes to the primer-specific portion or its complement, may have a length of anywhere between 8 and 15 nucleotides. In certain embodiments, both the forward and reverse primers may have minor groove binders attached to them.

In certain embodiments, one may use minor groove binders as follows in methods that employ a ligation probe set comprising: a first probe comprising a 5' primer specific portion; and a second probe comprising a 3' primer-specific portion. A minor groove binder is attached to the 3' end of the second probe, and a minor groove binder is attached to a primer that hybridizes to the complement of the 5' primer-specific portion of the first probe. In certain such embodiments, the presence of the minor groove binders facilitates use of short forward and reverse primers in an amplification reaction. For example, in certain embodiments, the short primer, or segment of the primer that hybridizes to the primer-specific portion or its complement, may have a length of anywhere between 8 and 15 nucleotides.

One may use any of the arrangements involving minor groove binders discussed above with various methods employing ligation probes with addressable portions as discussed herein. In certain embodiments, one may use such arrangements with different types of ligation and amplification methods. For example, one may use at least one probe and/or at least one primer with an attached minor groove binder in any of a variety of methods employing ligation and amplification reactions. Exemplary methods include, but are not limited to, those discussed in U.S. Pat. No. 6,027,889, PCT Published Patent Application No. WO 01/92579, and U.S. patent application Ser. Nos. 09/584,905 and 10/011, 993.

In certain embodiments, one may employ non-natural nucleotides other than the naturally occurring nucleotides A, G, C, T, and U. For example, in certain embodiments, one may employ primer-specific portions and primers and/or addressable portions and labeled probes that comprise pairs of non-natural nucleotides that specifically hybridize to one another and not to naturally occurring nucleotides. Exemplary, but nonlimiting, non-natural nucleotides are discussed, e.g., in Wu et al. *J. Am. Chem. Soc.* (2000) 122: 7621–32; Berger et al. *Nuc. Acids Res.* (2000) 28: 2911–14, Ogawa et al. *J. Am. Chem. Soc.* (2000) 122: 3274–87

Certain embodiments include a ligation agent. For example, ligase is an enzymatic ligation agent that, under appropriate conditions, forms phosphodiester bonds between the 3'-OH and the 5'-phosphate of adjacent nucleotides in DNA or RNA molecules, or hybrids. Exemplary ligases include, but are not limited to, Tth K294R ligase and Tsp AK16D ligase. See, e.g., Luo et al., Nucleic Acids Res., 24(14):3071–3078 (1996); Tong et al., Nucleic Acids Res., 27(3):788–794 (1999); and Published PCT Application No. WO 00/26381. Temperature sensitive ligases, include, but are not limited to, T4 DNA ligase, T7 DNA ligase, and *E. coli* ligase. In certain embodiments, thermostable ligases include, but are not limited to, Taq ligase, Tth ligase, Tsc ligase, and Pfu ligase. Certain thermostable ligases may be obtained from thermophilic or hyperthermophilic organisms, including but not limited to, prokaryotic, eucaryotic, or archael organisms. Certain RNA ligases may be employed in certain embodiments. In certain embodiments, the ligase is a RNA dependent DNA ligase, which may be employed with RNA template and DNA ligation probes. An exemplary, but nonlimiting example, of a ligase with such RNA dependent DNA ligase activity is T4 DNA ligase. In certain embodiments, the ligation agent is an "activating" or reducing agent.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of certain embodiments of the invention. Detailed protocols for chemical ligation methods and descriptions of appropriate reactive groups can be found, among other places, in Xu et al., Nucleic Acid Res., 27:875–81 (1999); Gryaznov and Letsinger, Nucleic Acid Res. 21:1403–08 (1993); Gryaznov et al., Nucleic Acid Res. 22:2366–69 (1994); Kanaya and Yanagawa, Biochemistry 25:7423–30 (1986); Luebke and Dervan, Nucleic Acids Res. 20:3005–09 (1992); Sievers and von Kiedrowski, Nature 369:221–24 (1994); Liu and Taylor, Nucleic Acids Res. 26:3300–04 (1999); Wang and Kool, Nucleic Acids Res. 22:2326–33 (1994); Purmal et al., Nucleic Acids Res. 20:3713–19 (1992); Ashley and Kushlan, Biochemistry 30:2927–33 (1991); Chu and Orgel, Nucleic Acids Res. 16:3671–91 (1988); Sokolova et al., FEBS Letters 232: 153–55 (1988); Naylor and Gilham, Biochemistry 5:2722–28 (1966); and U.S. Pat. No. 5,476,930.

In certain embodiments, at least one polymerase is included. In certain embodiments, at least one thermostable polymerase is included. Exemplary thermostable polymerases, include, but are not limited to, Taq polymerase, Pfx polymerase, Pfu polymerase, Vent® polymerase, Deep Vent™ polymerase, Pwo polymerase, Tth polymerase, UlTma polymerase and enzymatically active mutants and variants thereof. Descriptions of these polymerases may be found, among other places, at the world wide web URL: the-scientist.com/yr1998/jan/profile1_980105.html; at the world wide web URL: the-scientist.com/yr2001/jan/profile_010903.html; at the world wide web URL: the-scientist.com/yr2001/sep/profile2_010903.html; at the article The Scientist 12(1):17 (Jan. 5, 1998); and at the article The Scientist 15(17):1 (Sep. 3, 2001).

The skilled artisan will appreciate that the complement of the disclosed probe, target, and primer sequences, or combinations thereof, may be employed in certain embodiments of the invention. For example, without limitation, a genomic DNA sample may comprise both the target sequence and its complement. Thus, in certain embodiments, when a genomic sample is denatured, both the target sequence and its complement are present in the sample as single-stranded sequences. In certain embodiments, ligation probes may be designed to specifically hybridize to an appropriate sequence, either the target sequence or its complement.

C. Certain Exemplary Component Methods

Ligation according to the present invention comprises any enzymatic or chemical process wherein an internucleotide linkage is formed between the opposing ends of nucleic acid sequences that are adjacently hybridized to a template. Additionally, the opposing ends of the annealed nucleic acid sequences should be suitable for ligation (suitability for ligation is a function of the ligation method employed). The internucleotide linkage may include, but is not limited to, phosphodiester bond formation. Such bond formation may include, without limitation, those created enzymatically by a DNA or RNA ligase, such as bacteriophage T4 DNA ligase, T4 RNA ligase, T7 DNA ligase, *Thermus thermophilus* (Tth) ligase, *Thermus aquaticus* (Taq) ligase, or *Pyrococcus furiosus* (Pfu) ligase. Other internucleotide linkages include, without limitation, covalent bond formation between appropriate reactive groups such as between an α-haloacyl group and a phosphothioate group to form a thiophosphorylacetylamino group; and between a phosphorothioate and a tosylate or iodide group to form a 5'-phosphorothioester or pyrophosphate linkages.

In certain embodiments, chemical ligation may, under appropriate conditions, occur spontaneously such as by autoligation. Alternatively, in certain embodiments, "activating" or reducing agents may be used. Examples of activating agents and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light. Nonenzymatic ligation according to certain embodiments may utilize specific reactive groups on the respective 3' and 5' ends of the aligned probes.

In certain embodiments, ligation generally comprises at least one cycle of ligation, for example, the sequential procedures of: hybridizing the target-specific portions of a first probe and a second probe, that are suitable for ligation, to their respective complementary regions on a target nucleic acid sequence; ligating the 3' end of the first probe with the 5' end of the second probe to form a ligation product; and denaturing the nucleic acid duplex to separate the ligation product from the target nucleic acid sequence. The cycle may or may not be repeated. For example, without limitation, by thermocycling the ligation reaction to linearly increase the amount of ligation product.

According to certain embodiments, one may use ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. patent application Ser. No. 09/898,323.

In certain embodiments, one may employ poly dIC in a ligation reaction. In certain embodiments, one uses any number between 15 to 80 ng/microliter of poly dIC in a ligation reaction. In certain embodiments, one uses 30 ng/microliter of poly dIC in a ligation reaction.

One may use poly dIC in a ligation reaction with various methods employing ligation probes with addressable portions as discussed herein. In certain embodiments, one may use poly dIC with different types of ligation methods. For example, one may use poly dIC in any of a variety of methods employing ligation reactions. Exemplary methods include, but are not limited to, those discussed in U.S. Pat. No. 6,027,889, PCT Published Patent Application No. WO 01/92579, and U.S. patent application Ser. Nos. 09/584,905 and 10/011,993.

In certain embodiments, one forms a test composition for a subsequent amplification reaction by subjecting a ligation reaction composition to at least one cycle of ligation. In certain embodiments, after ligation, the test composition may be used directly in the subsequent amplification reaction. In certain embodiments, prior to the amplification reaction, the test composition may be subjected to a purification technique that results in a test composition that includes less than all of the components that may have been present after the at least one cycle of ligation. For example, in certain embodiments, one may purify the ligation product.

Purifying the ligation product according to certain embodiments comprises any process that removes at least some unligated probes, target nucleic acid sequences, enzymes, and/or accessory agents from the ligation reaction composition following at least one cycle of ligation. Such processes include, but are not limited to, molecular weight/size exclusion processes, e.g., gel filtration chromatography or dialysis, sequence-specific hybridization-based pullout methods, affinity capture techniques, precipitation, adsorption, or other nucleic acid purification techniques. The skilled artisan will appreciate that purifying the ligation product prior to amplification in certain embodiments reduces the quantity of primers needed to amplify the ligation product, thus reducing the cost of detecting a target sequence. Also, in certain embodiments, purifying the ligation product prior to amplification may decrease possible side reactions during amplification and may reduce competition from unligated probes during hybridization.

Hybridization-based pullout (HBP) according to certain embodiments of the present invention comprises a process wherein a nucleotide sequence complementary to at least a portion of one probe (or its complement), for example, the primer-specific portion, is bound or immobilized to a solid or particulate pullout support (see, e.g., U.S. Pat. No. 6,124,092). In certain embodiments, a composition comprising ligation product, target sequences, and unligated probes is exposed to the pullout support. The ligation product, under appropriate conditions, hybridizes with the support-bound sequences. The unbound components of the composition are removed, purifying the ligation products from those ligation reaction composition components that do not contain sequences complementary to the sequence on the pullout support. One subsequently removes the purified ligation products from the support and combines them with at least one primer set to form a first amplification reaction composition. The skilled artisan will appreciate that, in certain embodiments, additional cycles of HBP using different complementary sequences on the pullout support may remove all or substantially all of the unligated probes, further purifying the ligation product.

Amplification according to the present invention encompasses a broad range of techniques for amplifying nucleic acid sequences, either linearly or exponentially. Exemplary amplification techniques include, but are not limited to, PCR or any other method employing a primer extension step, and transcription or any other method of generating at least one RNA transcription product. Other nonlimiting examples of amplification are ligase detection reaction (LDR), and ligase chain reaction (LCR). Amplification methods may comprise thermal-cycling or may be performed isothermally. The term "amplification product" includes products from any number of cycles of amplification reactions, primer extension reactions, and RNA transcription reactions, unless otherwise apparent from the context.

In certain embodiments, amplification methods comprise at least one cycle of amplification, for example, but not limited to, the sequential procedures of: hybridizing primers to primer-specific portions of the ligation product or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated. In certain embodiments, amplification methods comprise at least one cycle of amplification, for example, but not limited to, the sequential procedures of: interaction of a polymerase with a promoter; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643–50 (1991), M. Innis et al., PCR Protocols: A Guide to Methods and Applications, Academic Press, New York, N.Y. (1990), R. Favis et al., Nature Biotechnology 18:561–64 (2000), and H. F. Rabenau et al., Infection 28:97–102 (2000); Sambrook and Russell, Ausbel et al.

Primer extension according to the present invention is an amplification process comprising elongating a primer that is annealed to a template in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand. Detailed descriptions of primer extension according to certain embodiments can be found, among other places in Sambrook et al., Sambrook and Russell, and Ausbel et al.

Transcription according to certain embodiments is an amplification process comprising an RNA polymerase interacting with a promoter on a single- or double-stranded template and generating a RNA polymer in a 5' to 3' direction. In certain embodiments, the transcription reaction composition further comprises transcription factors. RNA polymerases, including but not limited to T3, T7, and SP6 polymerases, according to certain embodiments, can interact with double-stranded promoters. Detailed descriptions of transcription according to certain embodiments can be found, among other places in Sambrook et al., Sambrook and Russell, and Ausbel et al.

Certain embodiments of amplification may employ multiplex PCR, in which multiple target sequences are simultaneously amplified (see, e.g., H. Geada et al., Forensic Sci. Int. 108:31–37 (2000) and D. G. Wang et al., Science 280:1077–82 (1998)).

In certain embodiments, one employs asymmetric PCR. According to certain embodiments, asymmetric PCR comprises an amplification reaction composition comprising (i) at least one primer set in which there is an excess of one primer (relative to the other primer in the primer set); (ii) at least one primer set that comprises only a first primer or only a second primer; (iii) at least one primer set that, during given amplification conditions, comprises a primer that results in amplification of one strand and comprises another primer that is disabled; or (iv) at least one primer set that meets the description of both (i) and (iii) above. Consequently, when the ligation product is amplified, an excess of one strand of the amplification product (relative to its complement) is generated.

In certain embodiments, one may use at least one primer set wherein the melting temperature ($Tm_{50}$) of one of the primers is higher than the $Tm_{50}$ of the other primer. Such embodiments have been called asynchronous PCR (A-PCR). See, e.g., U.S. patent application Ser. No. 09/875,211, filed Jun. 5, 2001. In certain embodiments, the $Tm_{50}$ of the first primer is at least 4–15° C. different from the $Tm_{50}$ of the second primer. In certain embodiments, the $Tm_{50}$ of the first primer is at least 8–15° C. different from the $Tm_{50}$ of the second primer. In certain embodiments, the $Tm_{50}$ of the first primer is at least 10–15° C. different from the $Tm_{50}$ of the second primer. In certain embodiments, the $Tm_{50}$ of the first primer is at least 10–12° C. different from the $Tm_{50}$ of the second primer. In certain embodiments, in at least one primer set, the $Tm_{50}$ of the at least one first primer differs from the melting temperature of the at least one second primer by at least about 4° C., by at least about 8° C., by at least about 10° C., or by at least about 12° C.

In certain embodiments of A-PCR, in addition to the difference in $Tm_{50}$ of the primers in a primer set, there is also an excess of one primer relative to the other primer in the primer set. In certain embodiments, there is a five to twenty-fold excess of one primer relative to the other primer in the primer set. In certain embodiments of A-PCR, the primer concentration is at least 50 mM.

In A-PCR according to certain embodiments, one may use conventional PCR in the first cycles such that both primers anneal and both strands are amplified. By raising the temperature in subsequent cycles, however, one may disable the primer with the lower Tm such that only one strand is amplified. Thus, the subsequent cycles of A-PCR in which the primer with the lower Tm is disabled result in asymmetric amplification. Consequently, when the ligation product is amplified, an excess of one strand of the amplification product (relative to its complement) is generated.

According to certain embodiments of A-PCR, the level of amplification can be controlled by changing the number of cycles during the first phase of conventional PCR cycling. In such embodiments, by changing the number of initial conventional cycles, one may vary the amount of the double strands that are subjected to the subsequent cycles of PCR at the higher temperature in which the primer with the lower Tm is disabled.

In certain embodiments, an A-PCR protocol may comprise use of a pair of primers, each of which has a concentration of at least 50 mM. In certain embodiments, conventional PCR, in which both primers result in amplification, is performed for the first 20–30 cycles. In certain embodiments, after 20–30 cycles of conventional PCR, the annealing temperature increases to 66–70° C., and PCR is performed for 5 to 40 cycles at the higher annealing temperature. In such embodiments, the lower Tm primer is disabled during such 5 to 40 cycles at higher annealing temperature. In such embodiments, asymmetric amplification occurs during the second phase of PCR cycles at a higher annealing temperature.

In certain embodiments, one employs asymmetric reamplification. According to certain embodiments, asymmetric reamplification comprises generating single-stranded amplification product in a second amplification process. In certain embodiments, the double-stranded amplification product of a first amplification process serves as the amplification target in the asymmetric reamplification process. In certain embodiments, one may achieve asymmetric reamplification using asynchronous PCR in which initial cycles of PCR conventionally amplify two strands and subsequent cycles are performed at a higher annealing temperature that disables one of the primers of a primer set as discussed above. In certain embodiments, the second amplification reaction composition comprises at least one primer set which comprises the at least one first primer, or the at least one second primer of a primer set, but typically not both. The skilled artisan understands that, in certain embodiments, asymmetric reamplification will also eventually occur if the primers in the primer set are not present in an equimolar ratio. In certain asymmetric reamplification methods, typically only single-stranded amplicons are generated since the second amplification reaction composition comprises only first or second primers from each primer set or a non-equimolar ratio of first and second primers from a primer set.

In certain embodiments, additional polymerase may also be a component of the second amplification reaction composition. In certain embodiments, there may be sufficient residual polymerase from the first amplification composition to synthesize the second amplification product.

Methods of optimizing amplification reactions are well known to those skilled in the art. For example, it is well known that PCR may be optimized by altering times and temperatures for annealing, polymerization, and denaturing, as well as changing the buffers, salts, and other reagents in the reaction composition. Optimization may also be affected by the design of the amplification primers used. For example, the length of the primers, as well as the G-C:A-T ratio may alter the efficiency of primer annealing, thus altering the amplification reaction. See James G. Wetmur, "Nucleic Acid Hybrids, Formation and Structure," in Molecular Biology and Biotechnology, pp. 605–8, (Robert A. Meyers ed., 1995).

In certain amplification reactions, one may use dUTP and uracil-N-glucosidase (UNG). Discussion of use of dUTP and UNG may be found, for example, in Kwok et al., "Avoiding false positives with PCR," Nature, 339:237–238 (1989); and Longo et al. "Use of uracil DNA glycosylase to control carry-over contamination in polymerase chain reactions," Gene, 93:125–128 (1990).

To detect whether a particular sequence is present, in certain embodiments, a labeled probe is included in the amplification reaction. According to certain embodiments, the labeled probe indicates the presence or absence (or amount) of a specific nucleic acid sequence in the reaction. These include, but are not limited to, 5'-nuclease probes, cleavage RNA probes, structure-specific nuclease probes, and hybridization dependent probes. In certain embodiments, the labeled probe comprises a fluorescing dye connected to a quenching molecule through a link element, e.g., through a specific oligonucleotide. Examples of such systems are described, e.g., in U.S. Pat. Nos. 5,538,848 and 5,723,591.

Other examples of suitable labeled probes according to certain embodiments are i-probes, scorpion probes, eclipse probes, and others. Exemplary, but nonlimiting, probes are discussed, for example, in Whitcombe et al., Nat. Biotechnol., 17(8):804–807 (1999) (includes scorpion probes); Thelwell et al., Nucleic Acids Res., 28(19):3752–3761 (2000) (includes scorpion probes); Afonina et al., Biotechniques, 32(4): (2002) (includes eclipse probes); Li et al., "A new class of homogeneous nucleic acid probes based on specific displacement hybridization", Nucleic Acids Res., 30(2):E5 (2002); Kandimall et al., Bioorg. Med. Chem., 8(8):1911–1916 (2000); Isacsson et al., Mol. Cell. Probes, 14(5):321–328 (2000); French et al, Mol. Cell. Probes, 15(6):363–374 (2001); and Nurmi et al., "A new label technology for the detection of specific polymerase chain reaction products in a closed tube", Nucleic Acids Res., 28(8), E28 (2000).

In certain embodiments, the amount of labeled probe that gives a fluorescent signal in response to an emitted light typically relates to the amount of nucleic acid produced in the amplification reaction. Thus, in certain embodiments, the amount of fluorescent signal is related to the amount of product created in the amplification reaction. In such embodiments, one can therefore measure the amount of amplification product by measuring the intensity of the fluorescent signal from the fluorescent indicator. According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.) and the ABI GeneAmp® 5700 Sequence Detection System (Applied Biosystems, Foster City, Calif.).

In certain embodiments, each of these functions may be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In certain embodiments, combined thermal cycling and fluorescence detecting devices can be used for precise quantification of target nucleic acid sequences in samples. In certain embodiments, fluorescent signals can be detected and displayed during and/or after one or more thermal cycles, thus permitting monitoring of amplification products as the reactions occur in "real time." In certain embodiments, one can use the amount of amplification product and number of amplification cycles to calculate how much of the target nucleic acid sequence was in the sample prior to amplification.

According to certain embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide.

According to certain embodiments, the amplification products can be scored as positive or negative as soon as a given number of cycles is complete. In certain embodiments, the results may be transmitted electronically directly to a database and tabulated. Thus, in certain embodiments, large numbers of samples may be processed and analyzed with less time and labor required.

According to certain embodiments, different labeled probes may distinguish between different target nucleic acid sequences. A non-limiting example of such a probe is a 5'-nuclease fluorescent probe, such as a TaqMan® probe molecule, wherein a fluorescent molecule is attached to a fluorescence-quenching molecule through an oligonucleotide link element. In certain embodiments, the oligonucleotide link element of the 5'-nuclease fluorescent probe binds to a specific sequence of an addressable portion or its complement. In certain embodiments, different 5'-nuclease fluorescent probes, each fluorescing at different wavelengths, can distinguish between different amplification products within the same amplification reaction.

For example, in certain embodiments, one could use two different 5'-nuclease fluorescent probes that fluoresce at two different wavelengths ($WL_A$ and $WL_B$) and that are specific to two different addressable portions of two different ligation products (A' and B', respectively). Ligation product A' is formed if target nucleic acid sequence A is in the sample, and ligation product B' is formed if target nucleic acid sequence B is in the sample. In certain embodiments, ligation product A' and/or B' may form even if the appropriate target nucleic acid sequence is not in the sample, but such ligation occurs to a measurably lesser extent than when the appropriate target nucleic acid sequence is in the sample. After amplification, one can determine which specific target nucleic acid sequences are present in the sample based on the wavelength of signal detected. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

D. Certain Exemplary Embodiments of Detecting Targets

The present invention is directed to methods, reagents, and kits for detecting the presence or absence of (or quantitating) target nucleic acid sequences in a sample, using ligation and amplification reactions. When a particular target nucleic acid sequence is present in a sample, a ligation product is formed that includes an addressable portion. Labeled probes are employed that provide a different detectable signal value depending upon whether a complementary sequence is present or absent during an amplification reaction. In certain embodiments, the labeled probes are designed to comprise a sequence that is the same as the sequence of the addressable portion or that is complementary to the sequence of the addressable portion.

In certain embodiments, one or more nucleic acid species are subjected to ligation and amplification reactions, either directly or via an intermediate, such as a cDNA target generated from an mRNA by reverse transcription. In certain embodiments, the initial nucleic acid comprises mRNA and a reverse transcription reaction may be performed to generate at least one cDNA, followed by at least one ligation reaction and at least one amplification reaction. In certain embodiments, DNA ligation probes hybridize to target RNA, and an RNA dependent DNA ligase is employed in a ligation reaction, followed by an amplification reaction. The ligation products and amplification products may be detected (or quantitated) using labeled probes.

Figure 2A:
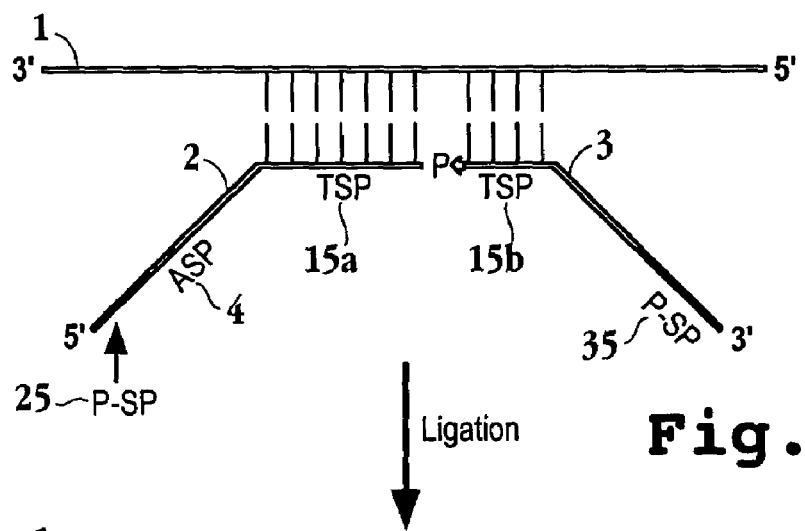

In certain embodiments, for each target nucleic acid sequence to be detected, a ligation probe set, comprising at least one first probe and at least one second probe, is combined with the sample to form a ligation reaction composition. In certain embodiments, the ligation composition may further comprise a ligation agent. In certain embodiments, the first and second probes in each ligation probe set are suitable for ligation together and are designed to hybridize to adjacent sequences that are present in the target nucleic acid sequence. When the target nucleic acid sequence is present in the sample, the first and second probes will, under appropriate conditions, hybridize to adjacent regions on the target nucleic acid sequence (see, e.g., probes 2 and 3 hybridized to target nucleic acid sequence 1 in FIG. 2A). In FIG. 2A, the target nucleic acid sequence (1) is depicted as hybridized with a first probe (2), for illustration purposes shown here as comprising a 5' primer-specific portion (25), an addressable portion (4), and a target-specific portion (15a), and a second probe (3) comprising a 3' primer-specific portion (35), a target-specific portion (15b) and a free 5' phosphate group ("P") for ligation.

Figure 2B:
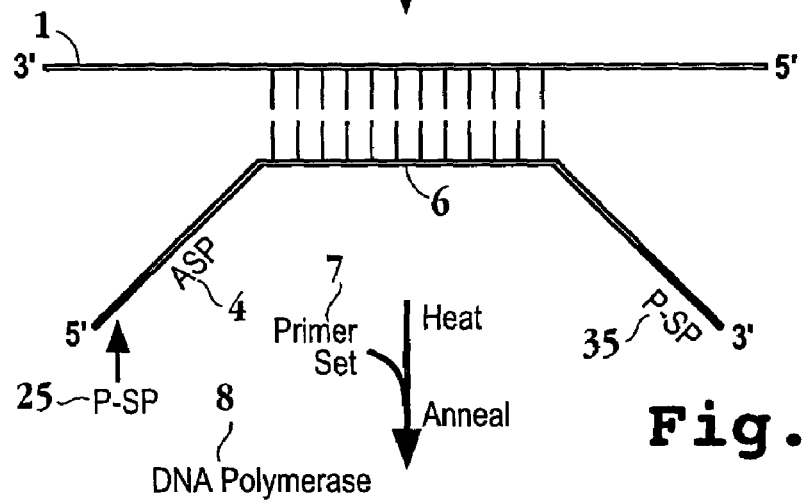

In certain embodiments, the adjacently hybridized probes may, under appropriate conditions, be ligated together to form a ligation product (see, e.g., ligation product 6 in FIG. 2B). FIG. 2B depicts the ligation product (6), generated from the ligation of the first probe (2) and the second probe (3). The ligation product (6) is shown comprising the 5' primer-specific portion (25), the addressable portion (4), and the 3' primer-specific portion (35). In certain embodiments, when the duplex comprising the target nucleic acid sequence (1) and the ligation product (6) is denatured, for example, by heating, the ligation product (6) is released.

Figure 2C:
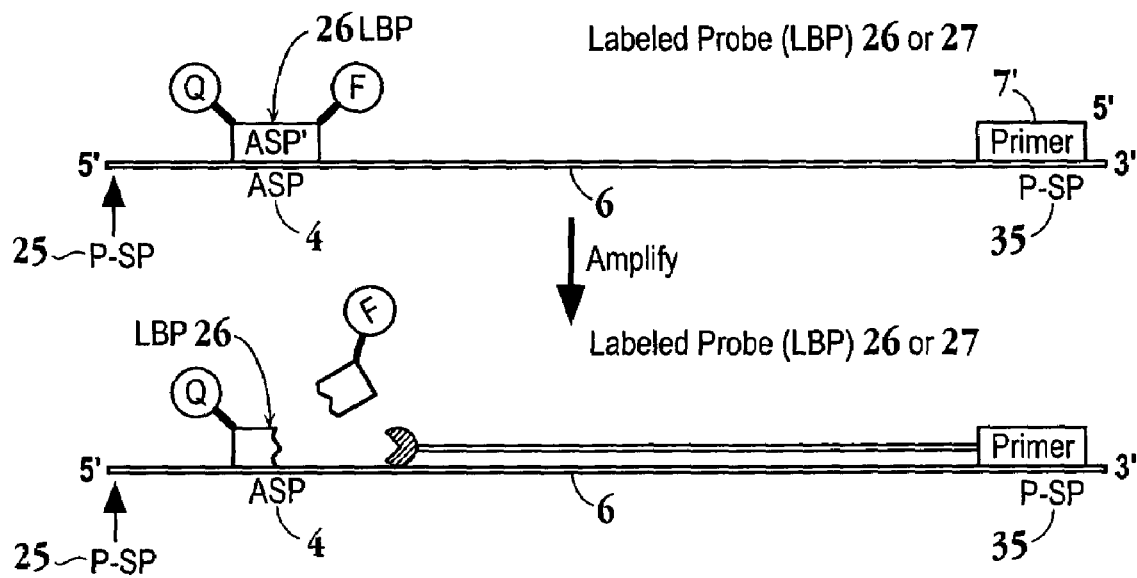
Figure 2D:
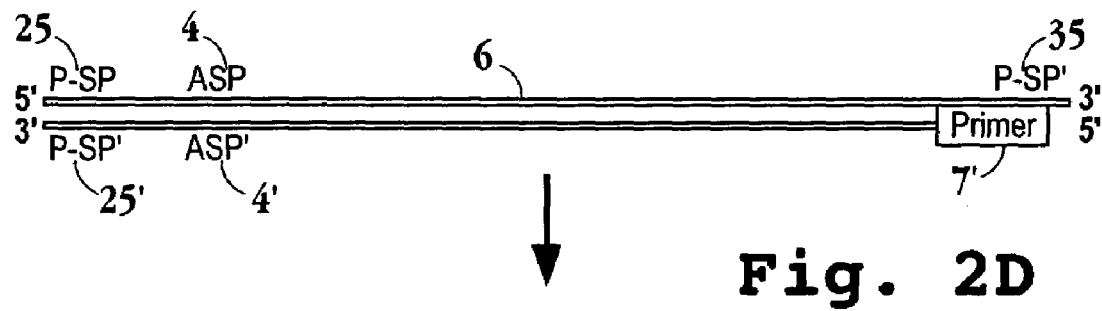

In certain embodiments, one forms an amplification reaction composition comprising the ligation product 6, at least one primer set 7, a polymerase 8, and a labeled probe 26 (see, e.g., FIG. 2C). The labeled probe 26 in the depicted embodiment is a 5'-nuclease fluorescent probe that comprises a quenching moiety (Q) linked to a fluorescent moiety (F) through an oligonucleotide link element that comprises a sequence complementary to the sequence of the addressable portion of the ligation product. In the first amplification cycle, the second primer 7', comprising a sequence complementary to the sequence of the 3' primer-specific portion 35 of the ligation product 6, hybridizes with the ligation product 6 and is extended, in the presence of DNA polymerase and deoxynucleoside triphosphates (dNTPs), in a template-dependent fashion. The 5'-nuclease activity of the polymerase results in cleavage of the 5'-nuclease fluorescent probe such that the fluorescent moiety (F) no longer is quenched by the quenching moiety (Q) and a fluorescent signal is detected. Detection of the fluorescent signal from the 5'-nuclease fluorescent probe indicates the presence of the target nucleic acid sequence in the sample.

In certain embodiments, if no target nucleic acid sequence had been present in the sample, no ligation product comprising the addressable portion and the 5' and 3' primer-specific portions would have been formed during the ligation reaction. Accordingly, no labeled probe would bind to a ligation product or an amplification product and there would be no cleavage of a labeled probe during the amplification reaction. (Some of the labeled probes may hybridize to unligated ligation probes.) Thus, the absence of a detectable signal during or after the amplification reaction would indicate the absence of target nucleic acid sequence in the sample. In certain embodiments, ligation products may form even if the appropriate target nucleic acid sequence is not in the sample, but such ligation occurs to a measurably lesser extent than when the appropriate target nucleic acid sequence is in the sample. In certain such embodiments, one can set an appropriate threshold difference between detectable signal values to differentiate between samples that include the appropriate target nucleic acid sequence and samples that do not include the appropriate target nucleic acid sequence.

Certain embodiments may be substantially the same as those depicted in FIGS. 2A to 2C, except that the oligonucleotide link element of the 5'-nuclease fluorescent probe comprises the sequence of the addressable portion of the ligation product (rather than a sequence that is complementary to the sequence of the addressable portion). See, e.g., labeled probe 27 in FIGS. 2D and 2E.

In the first amplification cycle, the second primer 7', comprising a sequence complementary to the sequence of the 3' primer-specific portion 35 of the ligation product 6, hybridizes with the ligation product 6 and is extended, in the presence of DNA polymerase and deoxynucleoside triphosphates (dNTPs), in a template-dependent fashion. The first amplification cycle generates a double-stranded product that comprises a complement of the 5' primer-specific portion (25) of the ligation product and a complement of the addressable portion (4) of the ligation product (see FIG. 2D).

Figure 2E:
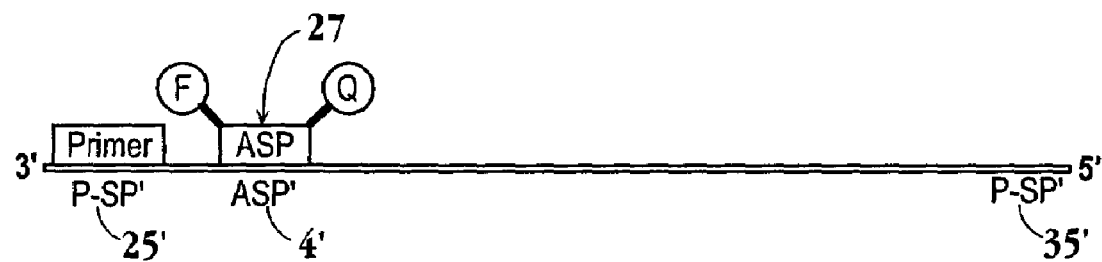
Figure 2E:
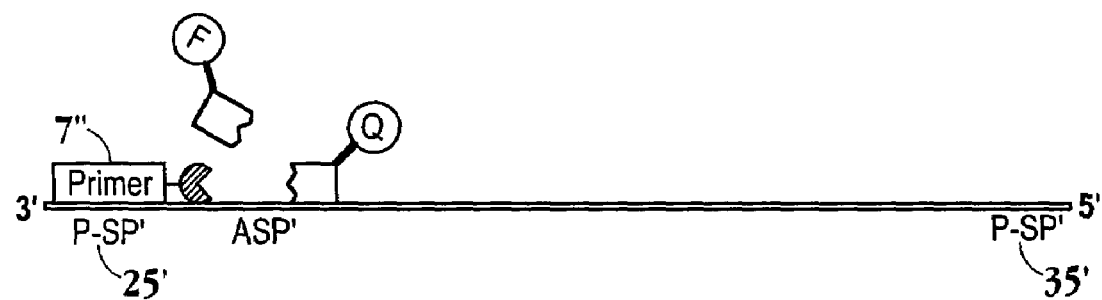

The double-stranded primer-extension product is denatured and subjected to one or more cycles of the polymerase chain reaction (PCR) including the labeled probe 27, which comprises an oligonucleotide link element that comprises the sequence of the addressable portion of the ligation product (see FIG. 2E). A primer that comprises the sequence of the 5' primer-specific portion of the ligation product hybridizes with the amplification product that includes a sequence 25' that is complementary to the sequence of the 5' primer-specific portion and is extended, in the presence of DNA polymerase and deoxynucleoside triphosphates (dNTPs), in a template-dependent fashion. See, e.g., FIG. 2E. The 5'-nuclease activity of the polymerase results in cleavage of the 5'-nuclease fluorescent probe such that the fluorescent moiety (F) no longer is quenched by the quenching moiety (Q) and a fluorescent signal is detected. Detection of the fluorescent signal from the 5'-nuclease fluorescent probe indicates the presence of the target nucleic acid sequence in the sample.

In certain embodiments, if no target nucleic acid sequence had been present in the sample, no ligation product comprising the addressable portion and the 5' and 3' primer-specific portions would have been formed during the ligation reaction. Thus, no amplification product comprising the complement of the addressable portion of such a ligation product would be formed. Accordingly, no labeled probe would bind to a ligation product or an amplification product and there would be no cleavage of a labeled probe during the amplification reaction. Thus, the absence of a detectable signal during or after the amplification reaction would indicate the absence of target nucleic acid sequence in the sample. In certain embodiments, ligation products may form even if the appropriate target nucleic acid sequence is not in the sample, but such ligation occurs to a measurably lesser extent than when the appropriate target nucleic acid sequence is in the sample. In certain such embodiments, one can set an appropriate threshold difference between detectable signal values to differentiate between samples that include the appropriate target nucleic acid sequence and samples that do not include the appropriate target nucleic acid sequence.

When the amplification product exists as a double-stranded molecule in either of the embodiments in FIG. 2, in certain embodiments, subsequent amplification cycles may exponentially amplify this molecule. In certain embodiments, one may quantitate the amount of target nucleic acid present in the sample by determining the level of intensity of the fluorescent signal.

Figure 3A:
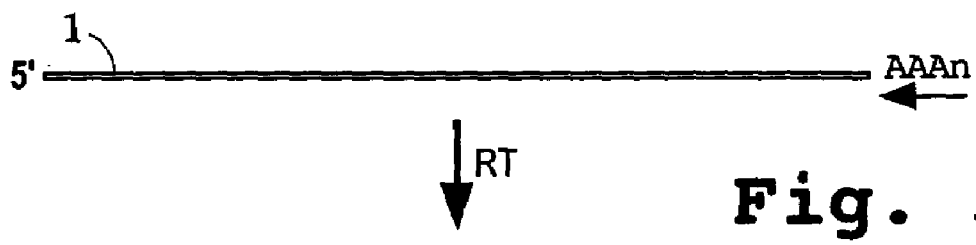
FIG. 3 (3A–3F) depicts exemplary embodiments of the invention comprising ligation and PCR-based amplification, wherein the exemplary target nucleic acid sequence is an mRNA in the sample.
Figure 3B:
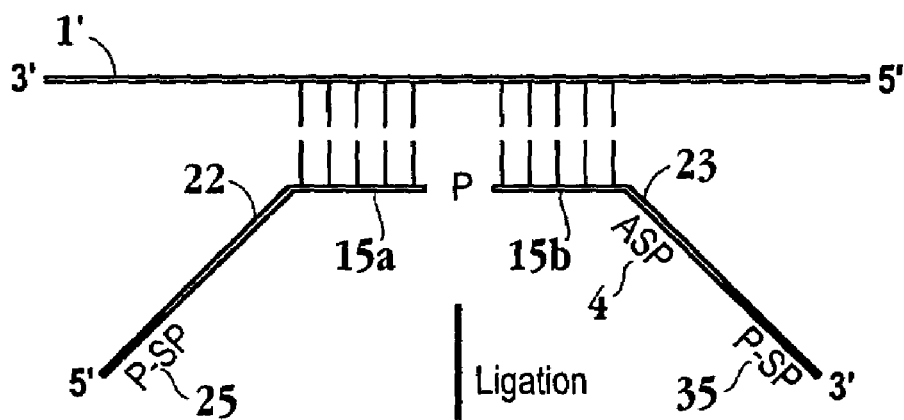
Figure 3C:
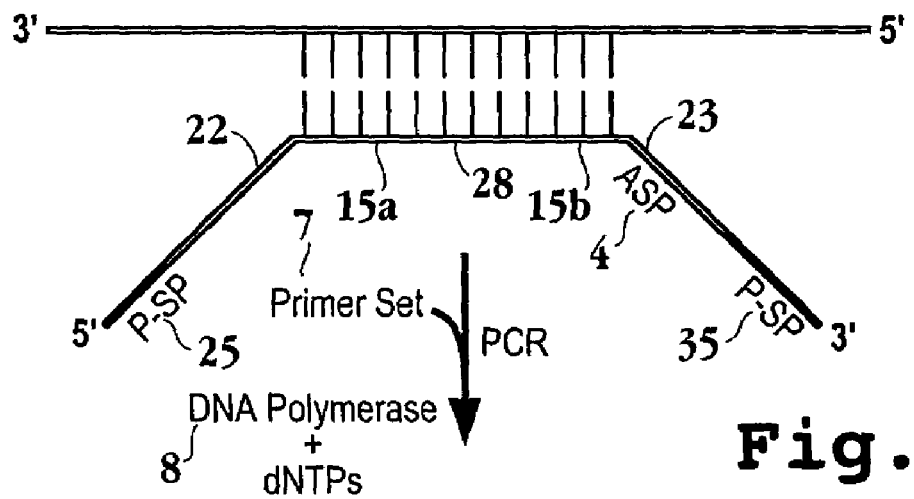
Figure 3D:
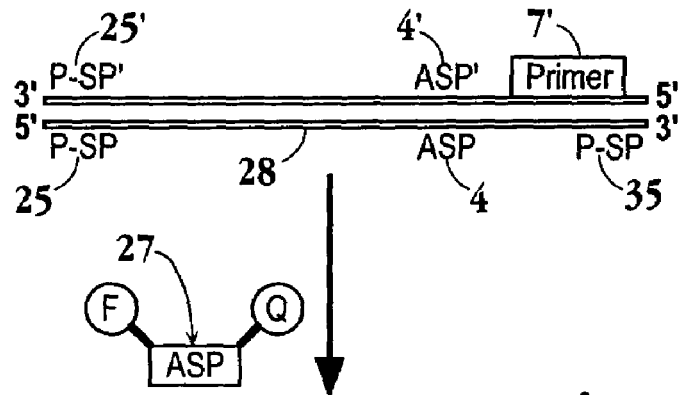

As shown in FIG. 3A, in certain embodiments, an mRNA is used to generate a cDNA copy 1'. The cDNA serves as a target nucleic acid sequence to which the first and second probes of the ligation probe set hybridize (see FIG. 3B). The first probe 22 comprises a 5' primer-specific portion (25) and a target-specific portion 15a, and the second probe 23 comprises a target-specific portion 15b, an addressable portion 4, and a 3' primer-specific portion (35). Under appropriate conditions, the adjacently hybridized probes can form a ligation product 28 comprising a 5' primer-specific portion (25), the target-specific portions 15a and 15b, the addressable portion 4, and the 3' primer-specific portion (35) (see FIG. 3C).

When the duplex formed by the target nucleic acid sequence 1' and the ligation product 28 is denatured, in certain embodiments by heating, the ligation product is released. In the presence of the appropriate primer set and under appropriate conditions, the 3' primer hybridizes with the 3' primer-specific portion 35 of the ligation product 28. The 3' primer is extended in the presence of DNA polymerase 8, generating a double-stranded product that comprises a complement (25') of the 5' primer-specific portion (25) of the ligation product and a complement (4') of the addressable portion (4) of the ligation product (see FIG. 3D).

Figure 3E:
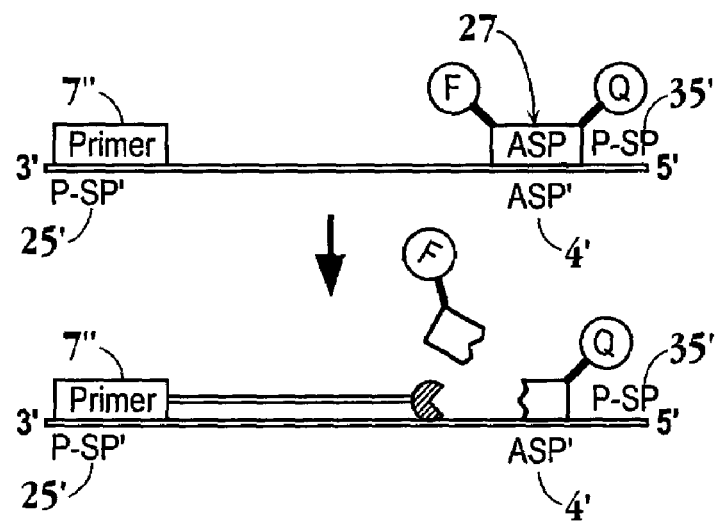
Figure 3F:
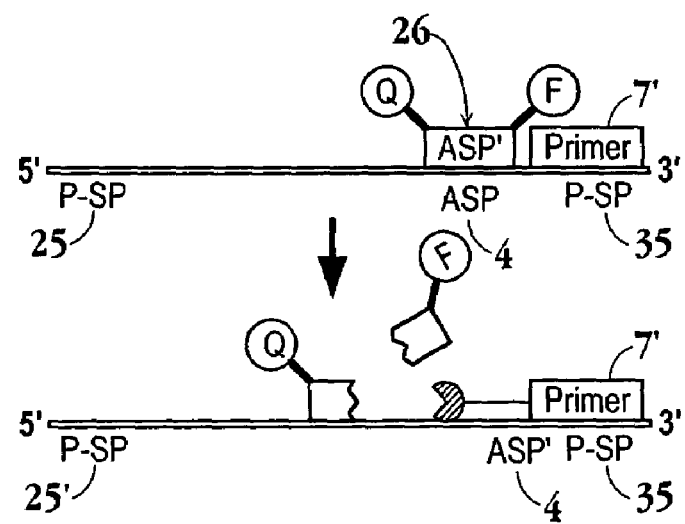

The double-stranded primer-extension product is denatured and subjected to one or more cycles of the polymerase chain reaction (PCR) including a labeled probe 27 (see, e.g., FIG. 3E). The labeled probe 27 in the depicted embodiment is a 5'-nuclease fluorescent probe that comprises a quenching moiety (Q) linked to a fluorescent moiety (F) by an oligonucleotide that comprises the sequence of the addressable portion of the ligation product. A primer that comprises the sequence of the 5' primer-specific portion of the ligation product hybridizes with the amplification product that includes a sequence 25' that is complementary to the sequence of the 5' primer-specific portion and is extended, in the presence of DNA polymerase and deoxynucleoside triphosphates (dNTPs), in a template-dependent fashion. The 5'-nuclease activity of the polymerase results in cleavage of the 5'-nuclease fluorescent probe such that the fluorescent moiety (F) no longer is quenched by the quenching moiety (Q) and a fluorescent signal is detected (see, e.g., FIG. 3E). Detection of the fluorescent signal from the 5'-nuclease fluorescent probe indicates the presence of the target nucleic acid sequence in the sample.

In certain embodiments, if no target nucleic acid sequence had been present in the sample, no ligation product comprising the addressable portion and the 5' and 3' primer-specific portions would have been formed during the ligation reaction. Thus, no amplification product comprising the complement of such a ligation product would be formed. Accordingly, no labeled probe would bind to a ligation product or an amplification product and there would be no cleavage of a labeled probe during the amplification reaction. Thus, the absence of a detectable signal during or after the amplification reaction would indicate the absence of target nucleic acid sequence in the sample. In certain embodiments, ligation products may form even if the appropriate target nucleic acid sequence is not in the sample, but such ligation occurs to a measurably lesser extent than when the appropriate target nucleic acid sequence is in the sample. In certain such embodiments, one can set an appropriate threshold difference between detectable signal values to differentiate between samples that include the appropriate target nucleic acid sequence and samples that do not include the appropriate target nucleic acid sequence.

Certain embodiments may be substantially the same as those depicted in FIGS. 3A to 3E, except that the oligonucleotide link element of the 5'-nuclease fluorescent probe comprises a sequence that is complementary to the sequence of the addressable portion of the ligation product (rather than the sequence of the addressable portion). See, e.g., labeled probe 26 in FIG. 3F.

In the first amplification cycle, the second primer 7', comprising a sequence complementary to the sequence of the 3' primer-specific portion 35 of the ligation product 28, hybridizes with the ligation product 28 and is extended, in the presence of DNA polymerase and deoxynucleoside triphosphates (dNTPs), in a template-dependent fashion. The 5'-nuclease activity of the polymerase results in cleavage of the 5'-nuclease fluorescent probe such that the fluorescent moiety (F) no longer is quenched by the quenching moiety (Q) and a fluorescent signal is detected.

In certain embodiments, if unligated second ligation probes have been substantially removed from the composition after the ligation reaction, detection of the fluorescent signal from the first amplification cycle indicates the presence of the target nucleic acid sequence in the sample. In certain embodiments, after the ligation reaction, one may substantially remove unligated second probes by exposing the composition to nucleic acids on a solid phase that are complementary to a sequence that is included on the first ligation probe, but that is not included on the second ligation probe. One may then separate the hybridized ligation products and unligated first ligation probes on the solid phase from the unligated second ligation probes.

If the unligated second ligation probes have not been substantially removed from the composition after the ligation reaction, detection of the fluorescent signal from the first amplification cycle does not necessarily indicate the presence of target nucleic acid in the sample. In such embodiments, labeled probes will hybridize to both unligated second ligation probes and ligation products. Also, the 5'-nuclease activity of the polymerase results in cleavage of the 5'-nuclease fluorescent probes that are hybridized to both the unligated second ligation probes and ligation products. Thus, the same signal would be detected whether or not any ligation product is present.

Subsequent cycles of amplification, however, may be employed in such embodiments to detect the presence or absence of (or to quantitate) target nucleic acid sequence. If no ligation product is present, the quantity of sequences that comprise an addressable sequence will not increase with subsequent cycles of amplification. Only the initial quantity of unligated second ligation probes will interact with the labeled probes to emit a signal.

In contrast, subsequent amplification cycles involving a composition that includes ligation products will result in an increased quantity of sequences that comprise the addressable portion. Thus, the quantity of amplification product with which the labeled probes interact increases. Thus, in certain embodiments, one can set the threshold difference between detectable signal values to differentiate between samples that include ligation product and samples that do not include ligation product. In certain embodiments, ligation products may form even if the appropriate target nucleic acid sequence is not in the sample, but such ligation occurs to a measurably lesser extent than when the appropriate target nucleic acid sequence is in the sample. In certain such embodiments, one can set an appropriate threshold difference between detectable signal values to differentiate between samples that include the appropriate target nucleic acid sequence and samples that do not include the appropriate target nucleic acid sequence.

The embodiments depicted in FIG. 3 may be modified by simply using target DNA in a sample rather than using cDNA resulting from reverse transcription of RNA. Also, the embodiments depicted in FIG. 3 may be modified by using the RNA as the target nucleic acid sequence to which the ligation probes hybridize.

In this application, whenever one employs an amplification reaction to determine whether there is a threshold difference in signal value from a labeled probe, the amplification reaction is carried out in a manner that will result in such a threshold difference if the target sequence that is being sought is included in the sample. The following nonlimiting exemplary embodiments illustrate this concept.

In a first exemplary embodiment, one employs a ligation probe set that comprises: a first probe that comprises a 5' primer specific portion and a target-specific portion; and a second probe that comprises a target specific portion, an addressable portion, and a 3' primer-specific portion. If the target nucleic acid is present in the sample, the first and second probes are ligated together to form a ligation product during a ligation reaction. The ligation product comprises the 5' primer-specific portion, the two target-specific portions, the addressable portion, and the 3' primer-specific portion.

In this embodiment, one forms an amplification reaction composition comprising the ligation product, a 5' nuclease fluorescent probe that comprises the sequence of the addressable portion, and a set of appropriate primers for the 5' and 3' primer-specific portions. The 5' nuclease fluorescent probe has a first detectable signal value when it is not hybridized to a complementary sequence. If one employs PCR as the amplification reaction, the first cycle of amplification will not result in a threshold difference between the first detectable signal value and a second detectable signal value during and/or after the first cycle of amplification. No threshold difference is detected, since the 5' nuclease fluorescent probe has the same sequence as the addressable portion of the ligation product and thus will not hybridize to the addressable portion. Thus, there will be no cleavage of the 5' nuclease fluorescent probe during the first cycle of amplification.

The first cycle of amplification, however, results in an amplification product that comprises the complement of the addressable portion and the complement of the 5' primer-specific portion at its 3' end. Thus, the 5' nuclease fluorescent probe will hybridize to the amplification product and will be cleaved during the second cycle of amplification. Thus, in this exemplary embodiment, the second cycle of amplification results in a threshold difference between the first detectable signal value and the second detectable signal value during and/or after the second cycle of amplification. Thus, in such embodiments, the amplification reaction used to determine whether there is a threshold difference in signal value comprises at least two cycles of PCR amplification.

In a second exemplary embodiment, one employs a ligation probe set that comprises: a first probe that comprises a 5' primer specific portion, an addressable portion, and a target-specific portion; and a second probe that comprises a target specific portion and a 3' primer-specific portion. If the target nucleic acid is present in the sample, the first and second probes are ligated together to form a ligation product during a ligation reaction. The ligation product comprises the 5' primer-specific portion, the addressable portion, the two target-specific portions, and the 3' primer-specific portion.

In this embodiment, one forms an amplification reaction composition comprising the ligation product, a 5' nuclease fluorescent probe that comprises a sequence complementary to sequence of the addressable portion, and a set of appropriate primers for the 5' and 3' primer-specific portions. The 5' nuclease fluorescent probe has a first detectable signal value when it is not hybridized to a complementary sequence. If one employs PCR as the amplification reaction, the first cycle of amplification will result in a threshold difference between the first detectable signal value and the second detectable signal value during and/or after the first cycle of amplification. A threshold difference is detected since the 5' nuclease fluorescent probe has a sequence complementary to sequence of the addressable portion of the ligation product and thus hybridizes to the addressable portion, and the first cycle of amplification results in cleavage of the 5' nuclease fluorescent probe. Thus, in such embodiments, the amplification reaction used to determine whether there is a threshold difference in signal value comprises at least one cycle of PCR amplification.

In a third exemplary embodiment, one employs a ligation probe set that comprises: a first probe that comprises a 5' primer specific portion and a target-specific portion; and a second probe that comprises a target specific portion, an addressable portion, and a 3' primer-specific portion. If the target nucleic acid is present in the sample, the first and second probes are ligated together to form a ligation product during a ligation reaction. The ligation product comprises the 5' primer-specific portion, the two target-specific portions, the addressable portion, and the 3' primer-specific portion.

In this embodiment, one forms an amplification reaction composition comprising the ligation product, a hybridization dependent probe that comprises the sequence of the addressable portion, and a set of appropriate primers for the 5' and 3' primer-specific portions. The hybridization dependent probe has a first detectable signal value when it is not hybridized to a complementary sequence. In this embodiment, PCR is used as the amplification reaction.

If unligated probes are not substantially removed from the amplification reaction composition prior to the first cycle of amplification, no threshold difference is detected during and/or after the first cycle. No threshold difference is detected, since, whether or not the sought ligation product is present, the first cycle of amplification will result in the same number of amplification products to which the hybridization dependent probes will hybridize. Both the unligated probes and the ligation products in such embodiments will comprise the same 3' primer-specific portion that will initiate extension in the first cycle of amplification and will comprise the same addressable portion. Thus, after the first cycle of amplification, when the hybridization dependent probes hybridize to the complement of the addressable portion on the amplification products, the same signal value will result whether or not the ligation product is present.

A threshold difference in detectable signal value, however, will result in subsequent cycles of amplification when amplification products with sequences complementary to the sequence of the addressable portion increase exponentially when the ligation product is amplified. In such subsequent cycles, if no ligation product is present, such amplification products will only increase linearly from the presence of the unligated probes. Such linear amplification occurs, since, unlike the ligation product, the unligated probes do not comprise 5' primer-specific portions.

In a fourth exemplary embodiment, one employs a ligation probe set that comprises: a first probe that comprises a 5' primer specific portion and a target-specific portion; and a second probe that comprises a target specific portion, an addressable portion, and a 3' primer-specific portion. If the target nucleic acid is present in the sample, the first and second probes are ligated together to form a ligation product during a ligation reaction. The ligation product comprises the 5' primer-specific portion, the two target-specific portions, the addressable portion, and the 3' primer-specific portion.

In this embodiment, one forms an amplification reaction composition comprising the ligation product, a hybridization dependent probe that comprises a sequence that is complementary to the sequence of the addressable portion, and a set of appropriate primers for the 5' and 3' primer-specific portions. Also, in this embodiment, a substantial portion of the hybridization dependent probes are not cleaved during a cycle of an amplification reaction. A "substantial portion of the hybridization dependent probes are not cleaved" refers to a portion of the total number of hybridization dependent probes that are designed to hybridize to a given nucleic sequence that is being amplified, and it does not refer to a portion of an individual probe. In certain embodiments, "a substantial portion of hybridization dependent probes that are not cleaved" means that at least 90% of the hybridization dependent probes are not cleaved. In certain embodiments, at least 95% of the hybridization dependent probes are not cleaved. The hybridization dependent probe has a first detectable signal value when it is not hybridized to a complementary sequence. In this embodiment, PCR is used as the amplification reaction.

If unligated probes are not substantially removed from the amplification reaction composition prior to the first cycle of amplification, no threshold difference is detected during and/or after the first cycle. No threshold difference is detected, since the hybridization dependent probes will hybridize to both unligated second probes and ligation products. The first cycle of amplification results in amplification products that have sequences that are complementary to the sequence of the addressable portion of the ligation product. Thus, the hybridization dependent probes do not hybridize to any amplification products produced in the first cycle of amplification.

A threshold difference in detectable signal value, however, will result after the second cycle of amplification, since the second cycle results in an increase of DNA that comprises the sequence of the addressable portion only if ligation product is present. Thus, in such embodiments, the amplification reaction used to determine whether there is a threshold difference in signal value comprises at least two cycles of PCR amplification.

In certain embodiments, one may employ a ligation probe set that includes an excess of the first probe to serve as a primer in subsequent amplification reactions. FIG. 14 shows certain exemplary embodiments. In FIG. 14, the first probe comprises a target-specific portion T-SP1. The second probe comprises a 3' primer-specific portion P-SP 42, an addressable portion ASP, and a target-specific portion T-SP2.

In such embodiments, after ligation (see FIGS. 14A and 14B), the primer set included in the amplification reaction composition may only comprise one primer 42' that comprises a sequence that is complementary to the sequence of the 3' primer-specific portion P-SP 42 of the second probe. After ligation, a cycle of amplification with that primer results in an amplification product that comprises a sequence complementary to the ligation product (see FIG. 14C).

In the second cycle of amplification, the primer P-SP 42' again results in an amplification product that comprises a sequence complementary to the ligation product (see FIG. 14D). Moreover, excess first probe serves as a primer that interacts with the sequence that is complementary to the ligation product to form an amplification product that comprises the sequence of the ligation product (see FIG. 14D).

FIG. 14 is provided to show exemplary embodiments involving the interaction of the first probe as a primer in an amplification reaction. FIG. 14 shows embodiments in which the second ligation probe comprises an addressable portion and the first ligation probe does not comprise an addressable portion. In certain embodiments employing excess first ligation probe as a primer, one may employ an addressable portion on either of the first or second ligation probes or on both the first and second ligation probes.

Also, FIG. 14 does not show the specific interaction of labeled probes with the addressable portions. In embodiments employing excess first ligation probe as a primer, one may employ labeled probes that comprise the sequence of an addressable portion and/or labeled probes that comprise a sequence complementary to an addressable portion.

Also, in certain embodiments, the first probe may contain additional nucleotides at the 5' end that do not hybridize to the target nucleic acid sequence.

Certain embodiments that employ excess first probe as a primer for subsequent amplification reactions can be used in the various embodiments of ligation and amplification that are discussed throughout this application. Examples include, but are not limited to, the embodiments depicted in FIG. 18. According to certain such embodiments, one may modify the first probes Z that are shown in FIG. 18 by not including a primer-specific portion P-SP1. In a subsequent amplification reaction, one may employ excess first probes to serve as primers rather than employing primers that correspond to a P-SP1 sequence on the first probe shown in FIG. 18.

One may use excess first probe of a ligation probe set as a primer with various methods employing ligation probes with addressable portions as discussed herein. In certain embodiments, one may use such arrangements with different types of ligation and amplification methods. For example, one may use excess first probe of a ligation probe set as a primer in any of a variety of methods employing ligation and amplification reactions. Exemplary methods include, but are not limited to, those discussed in U.S. Pat. No. 6,027,889, PCT Published Patent Application No. WO 01/92579, and U.S. patent application Ser. Nos. 09/584,905 and 10/011,993.

In certain embodiments, one may carry out the ligation reaction in a reaction volume that comprises all of the reagents for both the ligation and amplification reactions ("closed-tube" reactions). In certain such embodiments, one may then carry out the amplification reaction without removing ligation product from that reaction volume. Thus, in certain such embodiments, the reaction volume may comprise: the sample, a ligation probe set, a ligation agent, a polymerase, a labeled probe, a primer set, and dNTPs.

In certain such embodiments, one may employ a ligation reagent that does not function at the higher temperatures employed in a subsequent amplification reaction. In certain embodiments, one may substantially destroy the ligation reagent activity after the ligation reaction by subjecting the reaction volume to a high temperature for a given period of time prior to the amplification reaction. For example, in certain embodiments, one may employ a high temperature for a short cycle period during a ligation reaction such that the ligation reagent activity is not substantially destroyed, and after the ligation reaction, hold the reaction volume at the high temperature for a longer period of time that destroys a substantial amount of the ligation reagent activity. In certain embodiments, destroying a substantial amount of ligation reagent activity means destroying at least 90% of the ligation reaction activity. In certain embodiments, at least 95% of the ligation reaction activity is destroyed. In certain embodiments, 100% of the ligation reaction activity is destroyed.

In certain embodiments, one may employ other methods of substantially destroying the ligation reagent activity prior to the subsequent amplification reaction. For example, one may employ an agent that inhibits the activity of a ligation reagent at a higher temperature that is used for an amplification reaction, but that does not inhibit the ligation reagent at a lower temperature that is used for the ligation reaction.

In certain embodiments in which one includes amplification reagents in the reaction volume during a ligation reaction, one may employ amplification primers that do not interfere with hybridization and ligation of ligation probes during the ligation reaction.

In certain embodiments in which one includes amplification reagents in the reaction volume during a ligation reaction, one may employ polymerase that is substantially inactive in the ligation conditions that are employed. In certain embodiments, substantially inactive means that at least 90% of the polymerase is inactive. In certain embodiments, at least 95% of the polymerase is inactive. In certain embodiments, 100% of the polymerase is inactive.

In certain such embodiments, the polymerase may be substantially inactive at the temperatures that are employed for the ligation reaction. For example, in certain embodiments, a polymerase may not be substantially active at a lower temperature that is employed for a ligation reaction and the ligation reagent is active at such lower temperatures. In certain embodiments, one may employ an agent that inhibits the activity of a polymerase at a lower temperature that is used for a ligation reaction, but that does not inhibit the polymerase at a higher temperature that is used in an amplification reaction. Exemplary agents that may be used in such embodiments to inhibit polymerases at a lower temperature include, but are not limited to, aptamers. See, e.g., Lin et al., J. Mol. Biol., 271:100–111 (1997).

In certain embodiments, one may employ a polymerase that is not substantially activated at the conditions employed for a ligation reaction, but is subsequently activated after the ligation reaction. For example, in certain such embodiments, one may employ a polymerase that is not substantially activated when held at a high temperature for a short period, but is activated if held at the high temperature for a longer period. Using such a polymerase according to certain embodiments, one may employ a high temperature for a short cycle period during a ligation reaction such that the polymerase is not substantially activated, and after the ligation reaction, hold the reaction volume at the high temperature for a longer period of time such that the polymerase is activated. An exemplary, but nonlimiting, example of such a polymerase is AmpliTaq Gold® (Applied Biosystems, Foster City, Calif.).

In certain embodiments in which one includes amplification reagents in the reaction volume during a ligation reaction, one may employ labeled probes that do not interfere with hybridization and ligation of ligation probes during the ligation reaction.

In certain embodiments, one may add some or all of the reagents for the amplification reaction directly to the ligation reaction volume after a ligation reaction ("open tube" reactions). In certain embodiments, one may add at least a portion of the ligation reaction volume after a ligation reaction to reagents for the amplification reaction.

Figure 4A:
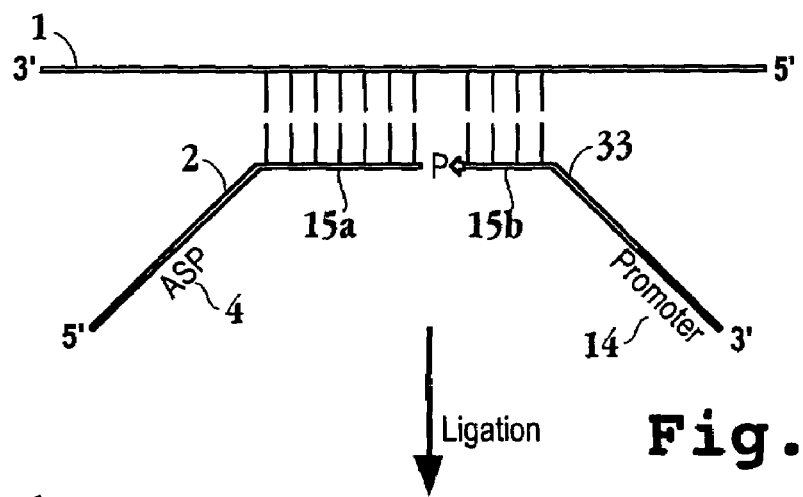
FIG. 4 (4A–4D) depicts exemplary embodiments comprising a ligation reaction and amplification using RNA polymerase to generate RNA transcription products.
Figure 4B:
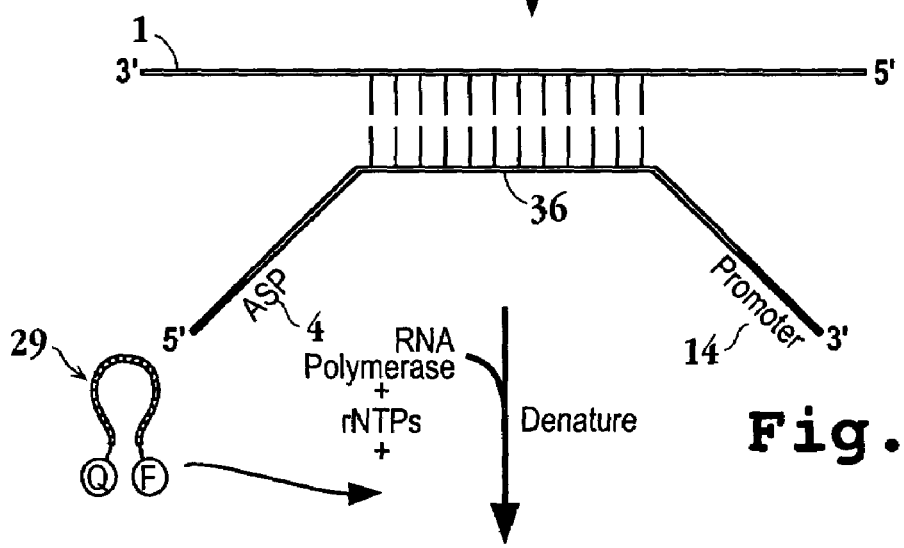

In certain embodiments as shown in FIG. 4A, the first probe 2, which comprises an addressable portion 4, and the second probe 33, which comprises a promoters 14, hybridize with the target nucleic acid sequence 1. The adjacently hybridized probes are ligated together to form a duplex that contains the target nucleic acid sequence 1 and the ligation product 36 comprising an addressable portion 4 and a promoters 14, as shown in FIG. 4B. When the duplex is denatured, the ligation product is released.

Figure 4C:
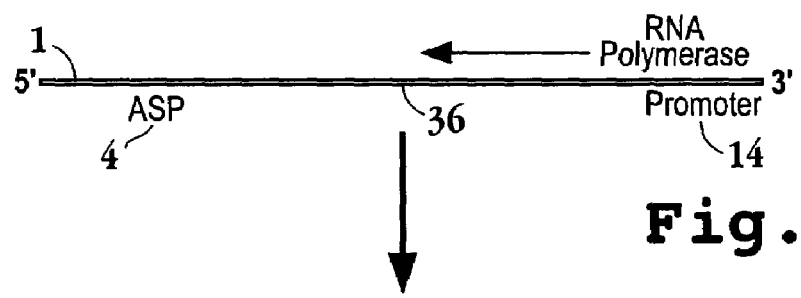
Figure 4D:
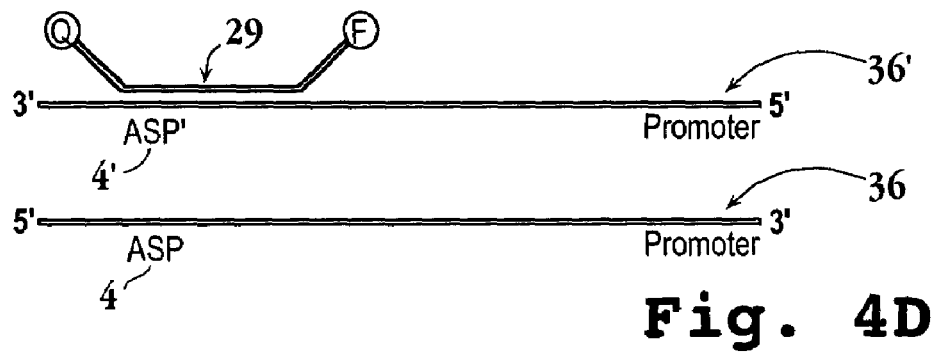

The ligation product is combined with an appropriate RNA polymerase 16 and rNTPs (see FIG. 4B). The RNA polymerase interacts with the promoter such that the rNTPs are added in a template-dependent fashion to make a transcription product 36' (see FIGS. 4C and 4D). A labeled probe 29 is added before, during, or after making the transcription product. The labeled probe 29 in the depicted embodiment is a hybridization dependent fluorescent probe that comprises a quenching moiety (Q) linked to a fluorescent moiety (F) through an oligonucleotide link element that comprises a sequence that is the same as the sequence of the addressable portion of the ligation product. When the hybridization dependent fluorescent probe is not hybridized to a sequence that is complementary to the addressable portion, the quenching moiety (Q) quenches the fluorescent moiety (F). The hybridization dependent fluorescent probe hybridizes to the sequence (4') of the transcription product that is complementary to the addressable portion such that the fluorescent moiety (F) no longer is quenched by the quenching moiety (Q) and a fluorescent signal is detected (see FIG. 4D). Detection of the fluorescent signal indicates the presence of the target nucleic acid sequence in the sample.

In certain embodiments, if no target nucleic acid sequence had been present in the sample, no ligation product comprising the addressable portion and the promoter would have been formed during the ligation reaction. Accordingly, no labeled probe would bind to a ligation product and there would be no fluorescent signal from a labeled probe. Thus, the absence of a detectable signal during or after the amplification reaction would indicate the absence of target nucleic acid sequence in the sample. In certain embodiments, ligation products may form even if the appropriate target nucleic acid sequence is not in the sample, but such ligation occurs to a measurably lesser extent than when the appropriate target nucleic acid sequence is in the sample. In certain such embodiments, one can set an appropriate threshold difference between detectable signal values to differentiate between samples that include the appropriate target nucleic acid sequence and samples that do not include the appropriate target nucleic acid sequence.

The skilled artisan will understand that some RNA polymerases typically form RNA transcription product(s) using a double-stranded transcription template, but not single-stranded transcription templates. Thus, when employing such RNA polymerases, a double-stranded version of the ligation product is typically generated before transcription occurs, as shown for example, in FIG. 5. The skilled artisan will also understand that it may be desirable to add RNA polymerase after some or all of the denaturation procedures.

Certain embodiments are shown in FIG. 5, which employ a first probe 32, which comprises a 5' primer-specific portion 25, an addressable portion 4, and a target-specific portion 15a, and a second probe 43, which comprises a target-specific portion 15b and a complement of a promoter 14'. The two probes hybridize with the target nucleic acid sequence 1. The adjacently hybridized probes are ligated together to form a duplex that contains the target nucleic acid sequence 1 and the ligation product 46, which comprises the primer-specific portion 25, the addressable portion 4, and the promoter complement 14', as shown in FIG. 5B. When the duplex is denatured, the ligation product 46 is released.

As shown in FIG. 5C, under appropriate conditions and in the presence of appropriate primers 7 and DNA polymerase 8, a double-stranded first amplification product 18 is generated, comprising the promoter 14 and its complement 14', and the addressable support-specific portion 4 and its complement 4'. The first amplification product is transcribed under appropriate conditions and in the presence of RNA polymerase 16 to generate transcription products 17. The transcription products may be detected and quantitated by, for example, using labeled probes, e.g., but not limited to, hybridization dependent probes.

Figure 8A:
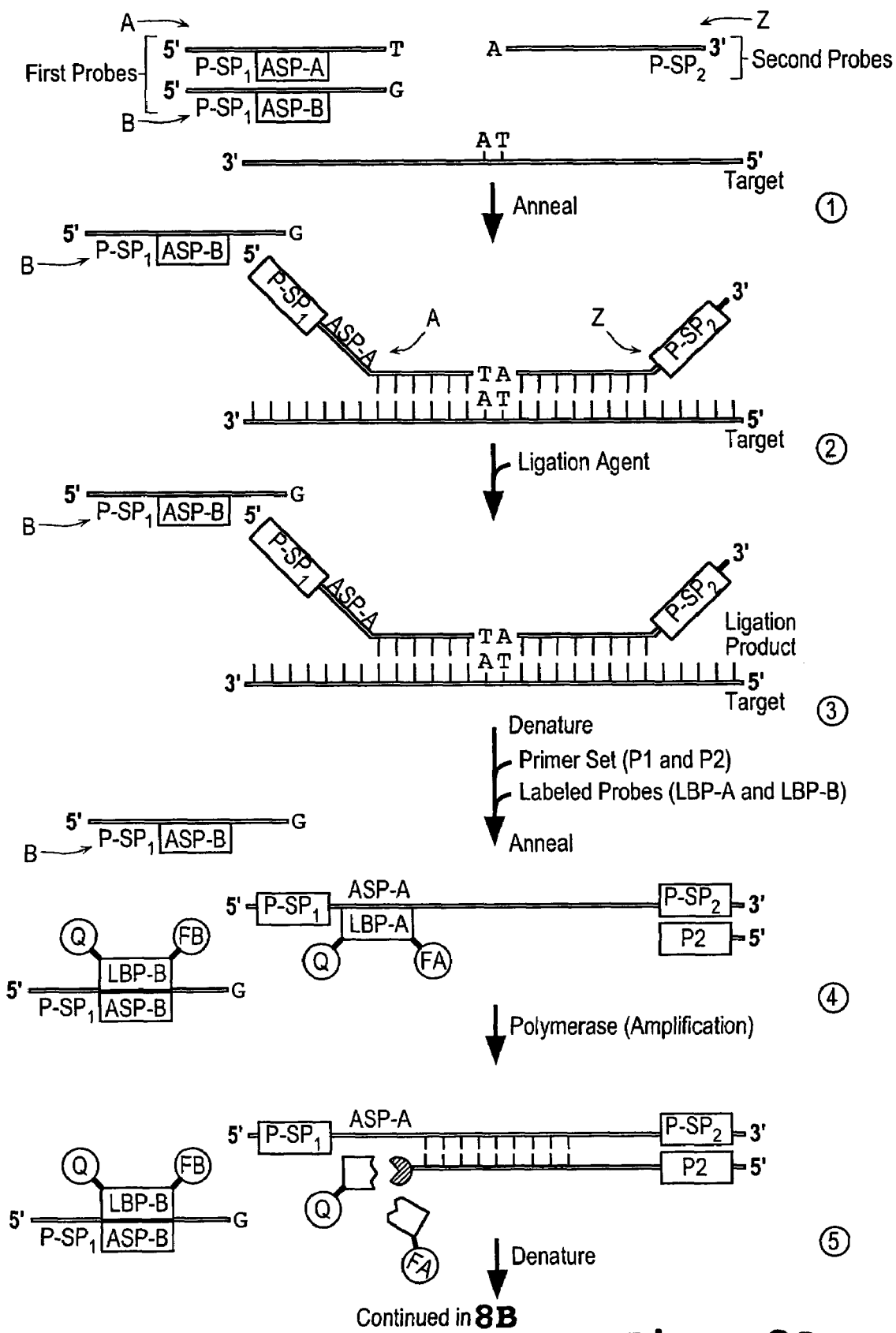
Figure 8B:
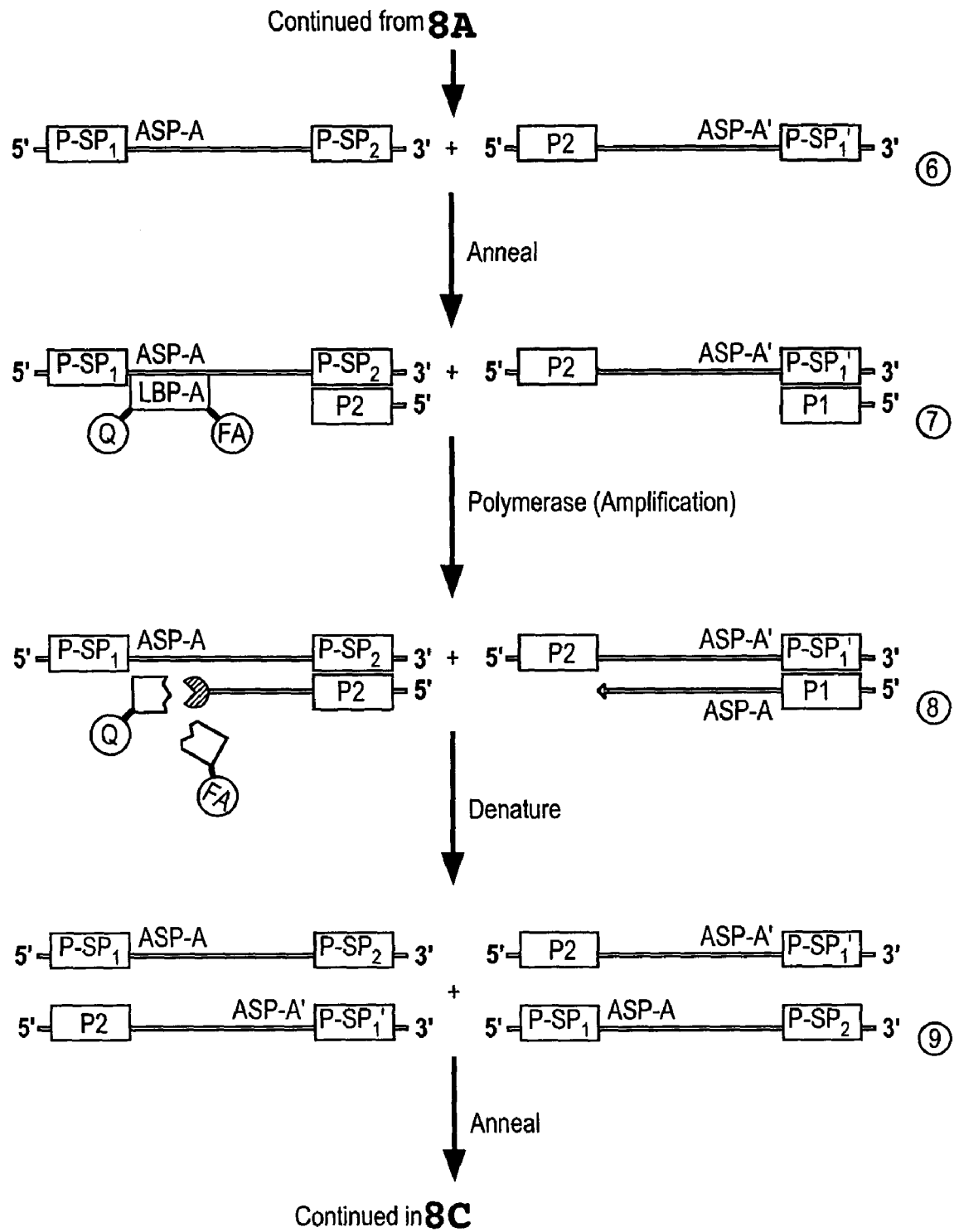
Figure 8C:
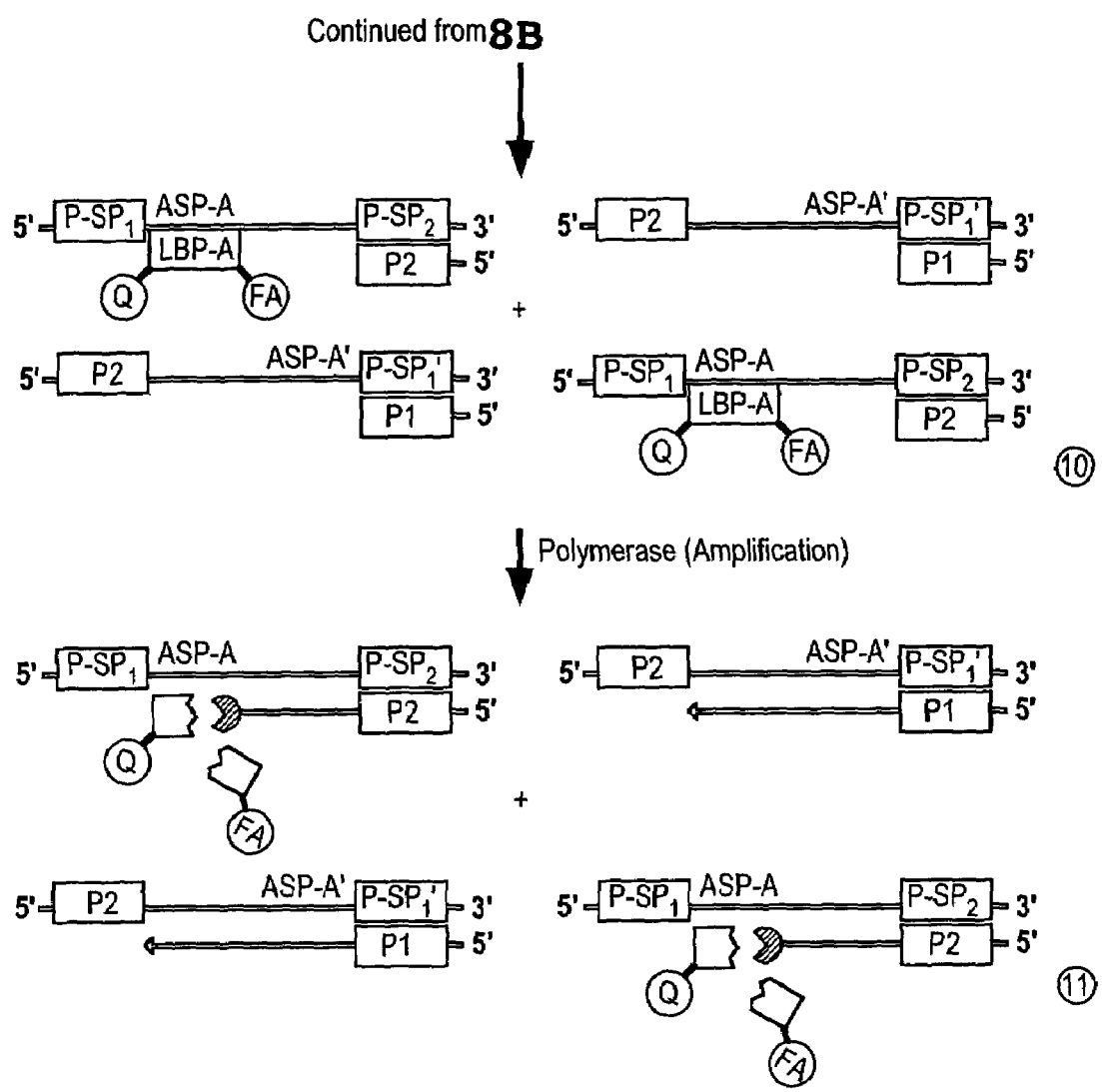

According to certain embodiments, the first and second probes in each ligation probe set are designed to be complementary to the sequences immediately flanking the pivotal nucleotide of the target sequence (see, e.g., probes A, B, and Z in FIG. 8(1)). In the embodiment shown in FIGS. 8A–8C, two first probes A and B of a ligation probe set will comprise a different nucleotide at the pivotal complement and a different addressable portion for each different nucleotide at the pivotal complement. One forms a ligation reaction composition comprising the probe set and the sample.

When the target sequence is present in the sample, the first and second probes will hybridize, under appropriate conditions, to adjacent regions on the target (see, e.g., FIG. 8(2)). When the pivotal complement is base-paired to the target, in the presence of an appropriate ligation agent, two adjacently hybridized probes may be ligated together to form a ligation product (see, e.g., FIG. 8(3)). In certain embodiments, if the pivotal complement of a first probe is not base-paired to the target, no ligation product comprising that mismatched probe will be formed (see, e.g., probe B in FIGS. 8(2) to 8(4).

In FIGS. 8(2) and 8(3), the first probe B is not hybridized to a target. In certain embodiments, the failure of a probe with a mismatched terminal pivotal complement to ligate to a second probe may arise from the failure of the probe with the mismatch to hybridize to the target under the conditions employed. In certain embodiments, the failure of a probe with a mismatched terminal pivotal complement to ligate to a second probe may arise when that probe with the mismatch is hybridized to the target, but the nucleotide at the pivotal complement is not base-paired to the target.

In certain embodiments, the reaction volume that is subjected to the ligation reaction forms a test composition. In certain embodiments, one then forms an amplification reaction composition comprising the test composition, at least one primer set, a polymerase, and a different labeled probe (LBP-A and LBP-B) for each different first probe, wherein the different labeled probes can provide detectably different signals (see, e.g., FIG. 8(4)). The labeled probes in the depicted embodiment are different 5'-nuclease fluorescent probes that comprise a quenching moiety (Q) linked to a detectably different fluorescent moiety (F) through a different oligonucleotide link element. The different oligonucleotide link elements comprise a sequence that is complementary to one of the different addressable portions of the different first ligation probes.

In the depicted embodiment, the first labeled probe (LBP-A) comprises a first fluorescent moiety (FA) that is linked to the quenching moiety (Q) through an oligonucleotide link element that comprises a sequence complementary to the sequence of the addressable portion (ASP-A) of the first probe A. In the depicted embodiment, the second labeled probe (LBP-B) comprises a second fluorescent moiety (FB) that is linked to the quenching moiety (Q) through an oligonucleotide link element that comprises a sequence that is complementary to the sequence of the addressable portion (ASP-B) of the first probe B. The fluorescent moieties of each of the different labeled probes emit detectably different signals from one another when they are not quenched by the quenching moiety.

In certain appropriate salts, buffers, and nucleotide triphosphates, the amplification reaction composition is subjected to at least one cycle of amplification. In the first amplification cycle, the second primer (P2), which comprises a sequence complementary to the sequence of the 3' primer-specific portion of the ligation product, hybridizes with the ligation product and is extended in a template-dependent fashion to create a double-stranded molecule.

Also during the first amplification cycle, the 5'-nuclease activity of the polymerase results in cleavage of the labeled probe that is hybridized to the addressable portion of the ligation product (see, e.g., labeled probe LBP-A in FIG. 8(5). Cleavage results in the fluorescent moiety (FA) no longer being quenched by the quenching moiety (Q) and a fluorescent signal is detected. Detection of the fluorescent signal from fluorescent moiety (FA) indicates the presence of the target nucleic acid sequence in the sample that has a pivotal nucleotide (A) that is complementary to the nucleotide (T) at the pivotal complement of the ligation product.

In this example, no target nucleic acid sequence in the sample has a pivotal nucleotide (C) that is complementary to the nucleotide of the pivotal complement of probe B. Thus, in this example, no ligation product comprising the addressable portion of probe B and the 3' primer-specific portion is formed. Accordingly, no labeled probe (LBP-B) comprising fluorescent moiety (FB) would bind to a ligation product or an amplification product and there would be no cleavage of a labeled probe (LBP-B) during the amplification reaction. Thus, the absence of a detectable signal from fluorescent moiety (FB) during or after the amplification reaction would indicate the absence of target nucleic acid sequence having pivotal nucleotide (C) in the sample. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide. In certain such embodiments, one can set an appropriate threshold difference between detectable signal values to differentiate between samples that include the appropriate target nucleic acid sequence and samples that do not include the appropriate target nucleic acid sequence.

In certain embodiments, when a 5'-nuclease probe hybridizes to an addressable portion or the complement of an addressable portion, the quenching moiety may be separated enough from the signal moiety such that a signal may be detected. In certain embodiments, the detectable signal value of such a signal (prior to cleavage) is less than the detectable signal value after cleavage of the 5'-nuclease probe. Thus, in certain such embodiments, one may set a threshold difference in detectable signal values such that a signal value that is detected after hybridization of the 5'-nuclease probe to a given sequence without cleavage does not result in the set threshold difference. A signal value that is detected with cleavage of the 5'-nuclease probe, however, will result in the set threshold difference.

In certain embodiments, subsequent amplification cycles may result in exponential amplification (see, e.g., FIG. 8(4)-(11)). Thus, with each cycle the signal value that is detected from the cleavage of labeled probes (LBP-A) will increase, while the signal value that is detected from labeled probes (LBP-B) will stay substantially the same.

In certain embodiments, one employs a ligation probe set that includes an addressable portion on both the first probe and the second probe, and the first probe and the second probe will ligate together when they hybridize adjacent to one another on the target nucleic acid sequence. In certain such embodiments, one employs different labeled probes for different addressable portions such that one of the labeled probes provides a control signal and the other labeled probe provides a target identification or quantitation signal.

For example, in certain embodiments, such a control could be added to the embodiment illustrated by FIG. 8 in the following nonlimiting manner. One forms a ligation reaction composition that comprises the same two first probes depicted in FIG. 8, which comprise two different nucleotides at the pivotal complement and two different addressable portions. The second probe, however, includes a third different addressable portion ASP-C between the target-specific portion and the 3' primer-specific portion.

Thus, the presence of the target nucleic acid that is shown in FIG. 8 during a ligation reaction, results in a ligation product that comprises the 5' primer-specific portion, addressable portion ASP-A, the two target specific portions, addressable portion ASP-C, and the 3' primer-specific portion. The same amplification reaction composition as discussed above for FIG. 8 is employed, except that composition further comprises an additional labeled probe LBP-C. The labeled probe LBP-C in the depicted embodiment is a 5'-nuclease fluorescent probe that comprises a quenching moiety (Q) linked to a third different fluorescent moiety (FC) that is linked to the quenching moiety (Q) through an oligonucleotide link element that comprises the same sequence as the addressable portion (ASP-C) of the second probe Z. The fluorescent moiety (FC) emits a detectably different signal than either of fluorescent moieties (FA) and (FB) when (FA), (FB), and (FC) are not quenched by the quenching moieties.

The first cycle of amplification of these modified embodiments of FIG. 8, should result in a threshold difference between the first and second detectable signal values from the fluorescent moiety (FA) of the cleaved labeled probe LBP-A. Also, the first cycle of amplification of these modified embodiments illustrated in FIG. 8, should also result in no threshold difference between the first and second detectable signal values from the fluorescent moiety (FB) of the uncleaved labeled probe LBP-B. (This is the same result that should occur in the embodiment illustrated in FIG. 8 without the third addressable portion ASP-C.)

The first cycle of amplification of these modified embodiments of FIG. 8, should also result in no threshold difference between the first and second detectable signal values from the fluorescent moiety (FC) of the uncleaved labeled probe LBP-C. (The labeled probe LBP-C comprises the sequence of addressable portion ASP-C of the ligation product, and thus should not be cleaved during the first amplification cycle.)

The first cycle of amplification of these modified embodiments of FIG. 8, also will result in an amplification product that is the complement of the ligation product. In these modified embodiments of FIG. 8, the labeled probe LBP-C will hybridize to that amplification product comprising the complement of the addressable portion ASP-C of the ligation product.

The second cycle of amplification of these modified embodiments of FIG. 8, should result in a doubling of signal value from the fluorescent moiety (FA) of labeled probe LBP-A from the first cycle of amplification. The second cycle of amplification of these modified embodiments of FIG. 8, should also result in a threshold difference between the first and second detectable signal values from the fluorescent moiety (FC) of the cleaved labeled probe LBP-C. The second cycle of amplification of these modified embodiments of FIG. 8, should also result in no threshold difference between the first and second detectable signal values from the fluorescent moiety (FB) of the uncleaved labeled probe LBP-B.

Subsequent cycles of amplification should result in exponential amplification of products corresponding to the ligation product and its complement, and thus, should result in corresponding increases of the detectable signal values from labeled probes LBP-A and LBP-C. If one observes a discrepancy between the expected increases in signal values from labeled probes LBP-A and LBP-C, one may conclude that the assay may not be progressing properly. If one observes the appropriate increases in signal values from labeled probes LBP-A and LBP-C, one may have confidence in the results from the assay.

The control may also be illustrated in embodiments in which the embodiment in FIG. 8 is modified by the presence of both possible target nucleic acids in the sample. In such embodiments, subsequent amplification cycles after the second amplification cycle should result in an increase in the signal value from the fluorescent moiety (FC) from labeled probe LBP-C that is similar to the combined increase in signal value from fluorescent moieties (FA) and (FB) from labeled probes LBP-A and LBP-B. This should be the result since a portion of the ligation products should have addressable portion ASP-A, a portion of the ligation products should have addressable portion ASP-B, but all of the ligation products should have addressable portion ASP-C.

Assume, e.g., that one observes a large increase in the detectable signal value from fluorescent moiety (FC), a significantly smaller increase in the detectable signal value from fluorescent moiety (FB), but observes no threshold difference in the detectable signal value from fluorescent moiety (FA). One may conclude from such results that the assay is not proceeding properly. It may be that ligation product with addressable portion ASP-A is present and is being amplified, but the labeled probe LBP-A is not functioning properly.

In certain embodiments, one employs a ligation probe set that includes two different addressable portions on at least one of the first probe and the second probe. In certain such embodiments, one employs different labeled probes for different addressable portions such that one of the labeled probes provides a control signal and the other labeled probe provides a target identification or quantitation signal.

For example, in certain embodiments, such a control could be added to the embodiment illustrated by FIG. 8 in the following nonlimiting manner. One forms a ligation reaction composition that comprises the same second probe that is depicted in FIG. 8. Similar to FIG. 8, one employs two first probes that comprise two different nucleotides at the pivotal complement and two different addressable portions. Each of the first probes, however, also includes a third different addressable portion ASP-C which is also located between the target-specific portion and the 3' primer-specific portion.

Thus, the presence of the target nucleic acid that is shown in FIG. 8 during a ligation reaction, results in a ligation product that comprises the 5' primer-specific portion, addressable portion ASP-A and addressable portion ASP-C, the two target specific portions, and the 3' primer-specific portion. The same amplification reaction composition as discussed above for FIG. 8 is employed, except that composition further comprises an additional labeled probe LBP-C. The labeled probe LBP-C in the depicted embodiment is a 5'-nuclease fluorescent probe that comprises a quenching moiety (Q) linked to a third different fluorescent moiety (FC) that is linked to the quenching moiety (Q) through an oligonucleotide link element that comprises a sequence that is complementary to the sequence of the addressable portion (ASP-C) of the first probes A and B. The fluorescent moiety (FC) emits a detectably different signal than either of fluorescent moieties (FA) and (FB) when (FA), (FB), and (FC) are not quenched by the quenching moieties.

The first cycle of amplification of these modified embodiments of FIG. 8, should result in a threshold difference between the first and second detectable signal values from the fluorescent moiety (FA) of the cleaved labeled probe LBP-A. Also, the first cycle of amplification of these modified embodiments illustrated in FIG. 8, should also result in no threshold difference between the first and second detectable signal values from the fluorescent moiety (FB) of the uncleaved labeled probe LBP-B. (This is the same result that should occur in the embodiment illustrated in FIG. 8 without the third addressable portion ASP-C.)

The first cycle of amplification of these modified embodiments of FIG. 8, should also result in a threshold difference between the first and second detectable signal values from the fluorescent moiety (FC) of the cleaved labeled probe LBP-C. The first cycle of amplification of these modified embodiments of FIG. 8, also will result in an amplification product that is the complement of the ligation product.

The second cycle of amplification of these modified embodiments of FIG. 8, should result in a doubling of signal value from the fluorescent moiety (FA) of labeled probe LBP-A from the first cycle of amplification. The second cycle of amplification of these modified embodiments of FIG. 8, should also result in a doubling of signal value from the fluorescent moiety (FC) of labeled probe LBP-C from the first cycle of amplification. The second cycle of amplification of these modified embodiments of FIG. 8, should also result in no threshold difference between the first and second detectable signal values from the fluorescent moiety (FB) of the uncleaved labeled probe LBP-B.

Subsequent cycles of amplification should result in exponential amplification of products corresponding to the ligation product and its complement, and thus, should result in corresponding increases of the detectable signal values from labeled probes LBP-A and LBP-C. If one observes a discrepancy between the expected increases in signal values from labeled probes LBP-A and LBP-C, one may conclude that the assay may not be progressing properly. If one observes the appropriate increases in signal values from labeled probes LBP-A and LBP-C, one may have confidence in the results from the assay.

The control may also be illustrated in embodiments in which the embodiment in FIG. 8 is modified by the presence of both possible target nucleic acids in the sample. In such embodiments, amplification cycles should result in an increase in the signal value from the fluorescent moiety (FC) from labeled probe LBP-C that is similar to the combined increase in signal value from fluorescent moieties (FA) and (FB) from labeled probes LBP-A and LBP-B. This should be the result since a portion of the ligation products should have addressable portion ASP-A, a portion of the ligation products should have addressable portion ASP-B, but all of the ligation products should have addressable portion ASP-C.

Assume, e.g., that one observes a large increase in the detectable signal value from fluorescent moiety (FC), a significantly smaller increase in the detectable signal value from fluorescent moiety (FB), but observes no threshold difference in the detectable signal value from fluorescent moiety (FA). One may conclude from such results that the assay is not proceeding properly. It may be that ligation product with addressable portion ASP-A is present and is being amplified, but the labeled probe LBP-A is not functioning properly.

In certain embodiments, a single-stranded amplification product is synthesized by, for example, without limitation, asymmetric PCR, asynchronous PCR, primer extension, RNA polymerase (see, e.g., FIG. 4), or asymmetric reamplification. In exemplary embodiments of asymmetric PCR, the amplification reaction composition is prepared with at least one primer set, wherein either the at least one first primer, or the at least one second primer, but not both, are added in excess. Thus, in certain embodiments, the excess primer to limiting primer ratio may be approximately 100:1, respectively. One of ordinary skill in the art will recognize that the optimal amounts of the primers according to certain embodiments may be determined empirically. In certain embodiments, amounts will range from about 2 to 50 nM for the limiting primer, and from about 100 to 900 nM for the primer in excess. Empirically, in certain embodiments, the concentration of one primer in the primer set is typically kept below 5 pmol per 100 µl of amplification reaction composition.

Since both primers are initially present in substantial excess at the beginning of the PCR reaction in certain embodiments, both strands are exponentially amplified. In certain embodiments, prior to completing all of the cycles of amplification, however, the limiting primer is exhausted. During the subsequent cycles of amplification, only one strand is amplified, thus generating an excess of single-stranded amplification products.

For example, but without limitation, in certain embodiments, after approximately 40 to 45 cycles of amplification are performed, the amplification process is completed with a long extension step. In certain embodiments, the limiting primer is typically exhausted by the $25^{th}$ cycle of amplification. During subsequent cycles of amplification only one strand of the amplification product is produced due to the presence of only one primer of the primer set. In certain embodiments, the labeled probe is a 5' nuclease probe that is designed to hybridize with a template strand that is not being produced during such subsequent cycles, such that each subsequent cycle results in an additional amount of signal. In certain embodiments, the labeled probe is a hybridization dependent probe that is designed to hybridize with a template strand that is being produced during such subsequent cycles, such that each subsequent cycle results in an additional amount of signal.

In certain exemplary asymmetric reamplification protocols, an air-dried first amplification composition containing double-stranded amplification product, is resuspended in 30 µl of 0.1×TE buffer, pH 8.0. The second amplification reaction composition is prepared by combining two microliters of the resuspended amplification product in a 0.2 ml MicroAmp reaction tube with 9 µl sterile filtered deionized water, 18 µl AmpliTaq Gold® mix (PE Biosystems, Foster City, Calif.), an appropriate amount of labeled probe, and 20–40 pmol of either the at least one first primer or the at least one second primer suspended in 1 µl 1×TE buffer.

The tubes are heated to 95° C. for 12 minutes, then cycled for ten cycles of (94° C. for 15 seconds, 60° C. for 15 seconds, and 72° C. for 30 seconds), followed by twenty-five cycles of (89° C. for 15 seconds, 53° C. for 15 seconds, and 72° C. for 30 seconds), and then 45 minutes at 60° C. The labeled probes are designed such that the detectable signal changes during the subsequent reamplification procedure, if the corresponding ligation product is present prior to the initial amplification reaction.

For example, in certain embodiments, one will form a ligation product from: a first probe that comprises a 5' primer-specific portion, an addressable portion, and a target-specific portion; and a second probe comprising a target specific portion and a 3' primer-specific portion. The primer set will include a first primer that comprises the sequence of the 5' primer-specific portion and a second primer that comprises a sequence that is complementary to the sequence of the 3' primer-specific portion. The labeled probe will comprise a sequence that is complementary to the sequence of the addressable portion and the second primer will be included in excess of the first primer.

In certain embodiments, a double-stranded amplification product is generated and subsequently converted into single-stranded sequences. Processes for converting double-stranded nucleic acid into single-stranded sequences include, without limitation, heat denaturation, chemical denaturation, and exonuclease digestion. Detailed protocols for synthesizing single-stranded nucleic acid molecules or converting double-stranded nucleic acid into single-stranded sequences can be found, among other places, in Ausbel et al., Sambrook et al., the Novagen Strandase™ product insert (Novagen, Madison, Wis.), and Sambrook and Russell.

In certain embodiments, the methods of the invention comprise universal primers, universal primer sets, or both. In certain embodiments, one may use a single universal primer set for any number of amplification reactions for different target sequences.

In certain embodiments, 5' primer-specific portions of at least two different ligation products comprise a sequence that is the same as at least a portion of one first primer in the reaction composition (see, e.g., primer PA in FIG. 9(A)). In certain embodiments, the 5' primer-specific portions of most ligation products in a reaction composition comprise a sequence that is the same as at least a portion of the at least one first primer (see, e.g., primer PA in FIG. 9(B)). In certain embodiments, the 5' primer-specific portions of all ligation products in a reaction composition comprise a sequence that is the same as at least a portion of the at least one first primer (see, e.g., primer PA in FIG. 9(C)). In certain embodiments, a reaction composition comprises more than one universal primer, more than one universal primer set, or both.

Such ligation products can be used in, for example, but are not limited to, a multiplex reaction wherein multiple target nucleic acid sequences are quantitated. According to certain embodiments, at least one universal primer, at least one universal primer set, or both, are used in a multiplex reaction.

According to certain embodiments, a multiplex reaction may include, for example, but is not limited to, six ligation products, each comprising a unique addressable portion corresponding to different target sequences or alleles or a combination of both (see, e.g., the six different ASP's in FIG. 9). In FIG. 9(A), the 5' primer-specific portions of two ligation products (A-Z) comprise a sequence that is the same as at least a portion of one first primer (PA) in the reaction composition. The 3' primer-specific portions of the same two ligation products comprise a sequence that is complementary to at least a portion of one second primer in the reaction composition. Thus, to exponentially amplify these six ligation products, one uses five primer sets (PA-PZ, PC-PZ, PD-PZ, PE-PZ, and PF-PZ).

FIG. 9(B) shows the same six ligation products, except that the 5' primer-specific portions of most of the ligation products comprise a sequence that is the same as at least a portion of one first primer in the reaction composition. The 3' primer-specific portions of all of the ligation products comprise a sequence that is complementary to at least a portion of one second primer in the reaction composition. To exponentially amplify these six ligation products, three primer sets are used (PA-PZ, PE-PZ, and PF-PZ).

FIG. 9(C) shows the same six ligation products, except that the 5' primer-specific portions of all of the ligation products comprise a sequence that is the same as at least a portion of one first primer in the reaction composition. The 3' primer-specific portions of all of the ligation products comprise a sequence that is complementary to at least a portion of one second primer in the reaction composition. To exponentially amplify these six ligation products, only one primer set is used (PA-PZ).

Thus, the same primer set will be used for at least two ligation products in the reaction composition (see, e.g., primers PA and PZ of FIG. 9(A)). In certain embodiments, most ligation products in the reaction composition will use the same primer set (see, e.g., primers PA and PZ of FIG. 9(B)). In certain embodiments, all of the ligation products in the reaction composition will use the same primer set (see, e.g., primers PA and PZ of FIG. 9(C)).

In the embodiments depicted in FIG. 9, the ligation probe comprising the 3' primer-specific portion also comprises an addressable portion (ASP). The embodiments depicted in FIG. 9 may be modified such that the ligation probe comprising the 5' primer-specific portion comprises an addressable portion and the ligation probe comprising the 3' primer-specific portion does not comprise an addressable portion. The embodiments depicted in FIG. 9 may be modified such that both the ligation probe comprising the 5' primer-specific portion and the ligation probe comprising the 3' primer-specific portion comprise an addressable portion.

According to certain embodiments, as few as one universal primer or one universal primer set can be used to amplify one or more ligation or amplification products, since the probes may be designed to share primer-specific portions but comprise different addressable portions and/or target-specific portions.

The methods of the instant invention according to certain embodiments may comprise universal primers or universal primer sets that decrease the number of different primers that are added to the reaction composition, reducing the cost and time required. For example, without limitation, in a 100-target-sequence multiplex reaction, typically 100 different primer sets are required using certain conventional methods. According to certain embodiments of the present invention, anywhere from 100 primer sets to as few as one primer set may be employed in the same 100 target multiplex. For example, in certain embodiments, all of the ligation or amplification products to be amplified by a universal primer or universal primer set comprise the same 5' primer-specific portion and the same 3' primer-specific portion. The skilled artisan will appreciate that, in certain embodiments, more than one universal primer set may be employed in a multiplex reaction, each specific to a different subset of ligation or amplification products in the reaction. In certain embodiments, the amplification reaction composition may comprise at least one universal primer or universal primer set and at least one primer or primer set that hybridizes to only one species of probe, ligation product, or amplification product.

In certain embodiments, because only one or a limited number of primers or primer sets are used for amplification, the methods are more cost-efficient and less time-consuming than conventional methods of detecting or quantitating target nucleic acid sequences in a sample. In certain embodiments, using a limited number of primers may also reduce variation in amplification efficiency and cross-reactivity of the primers. Additionally, in certain embodiments, quantitative results may be obtained from multiplex reactions for those ligation products or amplification products that are amplified by a universal primer or universal primer set, respectively.

The skilled artisan will appreciate that in certain embodiments, including, but not limited to, detecting multiple alleles, the ligation reaction composition may comprise more than one first probe or more than one second probe for each potential allele in a multiallelic target locus. In certain embodiments, those methods employ different probes with different addressable portions for each different allele at each locus. In certain such embodiments, the amplification reaction composition may include a different labeled probe for each different addressable portion. In certain embodiments, each different labeled probe may have a detectably different signal for each different addressable portion.

FIG. 12 illustrates certain such embodiments in which there are three biallelic loci. For each locus, one employs a ligation probe set comprising two first probes. In FIG. 12, there is a different probe set for each of the three different loci. Each probe set comprises two first probes for the two different alleles at each locus. Each of the first probes of each probe set comprises the same 5' primer-specific portion (P-SP(A)), a target-specific portion that is complementary to a portion of the given locus and includes a different nucleotide at the pivotal complement (A or G for the first locus; T or G for the second locus; G or C for the third locus), and a different addressable portion (AP1 or AP2 for the first locus; AP3 or AP4 for the second locus; AP5 or AP6 for the third locus). Each of the second probes of each probe set comprises the same 3' primer-specific portion (P-SP(Z)) and a different target-specific portion for each different locus.

In certain embodiments shown in FIG. 12, after ligation, one can perform a multiplex amplification reaction for all of the loci with the same primer set (PA) and (PZ) and six different labeled probes (LBP-1, LBP-2, LBP-3, LBP-4, LBP-5, and LBP-6) that comprise sequences complementary to (or the same as) each of the six different addressable portions. Also, the six different labeled probes provide six detectably different signals.

Thus, in this example, if amplification results in a threshold difference in detectable signal value from all six labeled probes, one would conclude that the sample was heterozygous at all three loci. If a threshold difference in signal value is only detected from labeled probes LBP-1, LBP-3, LBP-4, and LBP-5, one would conclude that the sample is homozygous at locus 1 with (C) as the pivotal nucleotide at locus 1, heterozygous at locus 2, and homozygous at locus 3 with (G) as the pivotal nucleotide.

In certain embodiments, one may employ the same two different addressable portions for the two different allelic options at more than one locus. In certain such embodiments, one may distinguish between the different loci by employing a different reaction composition for each locus.

Thus, if one wants to determine a single nucleotide difference in the alleles at three different biallelic loci, in certain such embodiments, one may employ three different reaction compositions that each have a different ligation probe set specific for the two options at each locus. FIG. 13 illustrates certain such embodiments in which one employs three different reaction compositions for three biallelic loci. In FIG. 13, there is a different probe set for each of the three different loci. Each probe set comprises two first probes for the two different alleles at each locus. Each of the first probes of each probe set comprises the same 5' primer-specific portion (P-SP(A)), a target-specific portion that is complementary to a portion of the given locus and includes a different nucleotide at the pivotal complement (A or G for the first locus; T or G for the second locus; G or C for the third locus), and a different addressable portion (AP1 or AP2) corresponding to one of the two allelic nucleotide options for each locus. The same set of addressable portions (AP1 and AP2) can be used on the two first probes of each of the three different probe sets. Each of the second probes of each probe set comprises the same 3' primer-specific portion (P-SP(Z)) and a different target-specific portion for each different locus.

In certain embodiments shown in FIG. 13, after separate ligation reactions for each locus, one can perform three separate amplification reactions for each locus with the same primer set (PA) and (PZ) and the same two labeled probes (LBP-1, which comprises a sequence that is complementary to (or is the same as) the sequence of the addressable portion AP1; and LBP-2, which comprises a sequence that is complementary to (or is the same as) the sequence of the addressable portion AP2). Also, the two different labeled probes provide two detectably different signals.

Thus, in this example, if amplification results in a threshold difference in detectable signal value from both labeled probes (LBP-1 and LBP-2) in all three reaction compositions, one would conclude that the sample was heterozygous at all three loci. Another possible result from the amplification reactions may be as follows: the first amplification reaction composition results in a threshold difference in detectable signal value from labeled probe LBP-1, the second amplification reaction composition results in a threshold difference in detectable signal value from labeled probes LBP-1 and LBP-2, and the third amplification reaction composition results in a threshold difference in detectable signal value from labeled probe LBP-1. One would conclude from such results that the sample is homozygous at locus 1 with (C) as the pivotal nucleotide, heterozygous at locus 2, and homozygous at locus 3 with (G) as the pivotal nucleotide.

In certain embodiments, one may analyze many different target sequences employing specific different probe sets in separate reaction compositions. For example, one could employ a 96 well plate with 96 different ligation probe sets for 96 different target nucleic acid sequences. In certain embodiments, one may want to detect the presence or absence of (or to quantitate) a single target nucleic acid sequence with each of the 96 probe sets. In certain such embodiments, one may employ the same set of two primers and the same labeled probe in each of the different 96 wells to obtain results for 96 different target sequences.

In certain embodiments, one may want to detect the presence or absence of (or to quantitate) two different alleles at 96 different loci with 96 different ligation probe sets. In certain embodiments, each probe set comprises two first probes and one second probe. In certain embodiments, each of the first probes of each probe set comprises a target-specific portion that is complementary to a portion of the given locus and includes a different nucleotide at the pivotal complement, and one of two different addressable portions corresponding to one of the two allelic nucleotide options for each locus. In certain embodiments, the same two different addressable portions can be used on the two first probes of each of the 96 probe sets. In certain embodiments, each of the second probes of each probe set comprises a different target-specific portion for each locus. In certain embodiments, the two first probes of each of the 96 probe sets may further comprise the same primer-specific portion. In certain embodiments, each of the second probes of each of the 96 probe sets may further comprise another primer-specific portion.

In certain such embodiments, after ligation, one may perform 96 separate amplification reactions in the 96 different wells. In certain such embodiments, one may use in all of the 96 wells the same primer set and the same two labeled probes. One labeled probe may comprise a sequence that is complementary to (or is the same as) one of the sequences of the two addressable portions, and the other labeled probe may comprise a sequence that is complementary to (or is the same as) the sequence of the other of the two addressable portions. Also, the two different labeled probes provide two detectably different signals. One may detect which allele or alleles are present in each of 96 wells by detecting a change in detectable signal value from the labeled probes.

In certain embodiments, one may want to detect the presence or absence of (or to quantitate) two different alleles at 288 different loci with 288 ligation probe sets. One may employ a 96 well plate in which each well includes three different probe sets for three different loci. Each of the three probe sets for each well may comprise two first probes that each comprise a different addressable portion for each of the allele options at each locus. See, e.g., FIG. 12, where there are six different first probes with six different addressable portions (AP1, AP2, AP3, AP4, AP5, and AP6). One may employ the same six different addressable portions on the three different probe sets in each of the wells. In certain such embodiments, one may employ the same set of two primers and the same six labeled probes in each of the different 96 wells to obtain results for 288 different biallelic loci.

The skilled artisan will understand that, in various embodiments, ligation probes can be designed with a pivotal complement at any location in either the first probe or the second probe. Additionally, in certain embodiments, ligation probes may comprise multiple pivotal complements.

In certain embodiments that employ ligation probe sets that comprise multiple first probes for a given locus that comprise target-specific portions with different pivotal complements, the target-specific portions of each of the different first probes for a given locus may have the same sequence except for a different nucleotide at the pivotal complement. In certain embodiments, the target-specific portions of each of the first probes for a given locus may have a different nucleotide at the pivotal complement and may have different length sequences 5' to the pivotal complement. In certain such embodiments, such target-specific portion sequences 5' to the pivotal complement may all be complementary to a portion of the same locus nucleic acid sequence adjacent to the pivotal nucleotide, but may have different lengths. For example, in such embodiments in which there are two different first probes, the target-specific portion sequences 5' to the pivotal complement may be the same except one of them may have one or more additional nucleotides at the 5' end of the target-specific portion.

In certain embodiments that employ ligation probe sets that comprise multiple second probes for a given locus that comprise target-specific portions with different pivotal complements, the target-specific portions of each of the different second probes for a given locus may have the same sequence except for a different nucleotide at the pivotal complement. In certain embodiments, the target-specific portions of each of the second probes for a given locus may have a different nucleotide at the pivotal complement and may have different length sequences 3' to the pivotal complement. In certain such embodiments, such target-specific portion sequences 3' to the pivotal complement may all be complementary to a portion of the same locus nucleic acid sequence adjacent to the pivotal nucleotide, but may have different lengths. For example, in such embodiments in which there are two different second probes, the target-specific portion sequences 3' to the pivotal complement may be the same except one of them may have one or more additional nucleotides at the 3' end of the target-specific portion.

In certain embodiments, one may add additional nucleotides to the end of a target specific portion of a ligation probe to affect its melting temperature. For example, in certain embodiments, the different nucleotide at the pivotal nucleotide of two first probes of a ligation probe set may result in different melting temperatures for such probes if they have the same length target-specific portion. In certain such embodiments, one may minimize such melting temperature differences by adding one or more additional nucleotides to the end of target-specific portion opposite the end that aligns with an adjacent ligation probe of a probe set.

In certain embodiments, one may employ probes that include one or more spacer nucleotides between an addressable portion and a target-specific portion. In certain embodiments, such a spacer nucleotide may be included to affect the melting temperature of a ligation probe. For example, in certain embodiments, one or more nucleotides of an addressable portion may be complementary to the target nucleic acid sequence in the region adjacent to the sequence that hybridizes to the target-specific portion of a ligation probe. For example, the end of a target-specific portion (TSP) adjacent to an addressable portion (ASP), and the end of the addressable portion adjacent to the target-specific portion may hybridize to a target nucleic acid as follows:

ASP/TSP(hybridizingportionsshownwithdouble underlining)
. . . <u>ACG</u>/<u>ATC</u> . . . (ligation probe)
. . . TGC/TAG . . . (target nucleic acid)

In certain such embodiments, the hybridization of the one or more nucleotides of the addressable portion to the target influences the melting temperature of the probe.

In certain such embodiments, one may introduce one or more spacer nucleotides between the addressable portion and the target-specific portion of the probe such that the spacer nucleotide(s) and the addressable portion will not hybridize to the target nucleic acid. In the specific example above, for example, one may introduce a spacer "C" between the target-specific portion and the addressable portion as follows:

ASP//TSP(hybridizingportionsshownwithdouble underlining)
. . . <u>ACG</u>/C/<u>ATC</u> . . . (ligation probe)
. . . TGC/TAG . . . (target nucleic acid)

In certain embodiments, one or more spacer nucleotides may be included between different portions of a ligation probe. For example, in certain embodiments, one or more spacer nucleotides may be included between a primer-specific portion and an addressable portion. In certain embodiments, one or more spacer nucleotides may be included between a primer-specific portion and a target-specific portion.

In certain embodiments, the target-specific portions of two ligation probes that are intended to hybridize to the same portion of a target nucleic acid sequence may include different nucleotides as long as such differences do not prevent appropriate ligation. For example, in certain embodiments, as long as appropriate ligation is not prevented, two probes that comprise target-specific portions that are designed to hybridize to an identical portion of a target, but have different pivotal complements A and C at their 3' ends, may include variation within the target-specific portion as follows (see lower case nucleotide):

```
5' CATGCcAATGACGGA-3'      (SEQ ID NO:24)

5' CATGCgAATGACGGC-3'      (SEQ ID NO:25)
```

In certain embodiments, the number of ligation probes used to detect any number of target sequences, is the product of the number of targets to be detected times the number of alleles to be detected per target plus one (i.e., (number of target sequences×[number of alleles+1]). Thus, to detect 3 biallelic sequences, for example, nine probes are used (3× [2+1]). In certain embodiments, to detect 4 triallelic sequences, 16 probes are used (4×[3+1]), and so forth.

The significance of the decrease in the number of primers and labeled probes in certain embodiments, and therefore the cost and number of manipulations, becomes readily apparent when performing genetic screening of an individual for a large number of multiallelic loci or of many individuals. In certain embodiments, to amplify the ligation product of a target sequence, two primers are used. One primer is complementary to the sequence of the 3' primer-specific portion of the ligation products, and one primer comprises the sequence of the 5' primer-specific portion. Using certain conventional methods, one employs three different primers for each different ligation product. Thus, to amplify the ligation products for three biallelic loci potentially present in an individual using certain conventional methodology, one would use 9 (3n, where n=3) primers.

In contrast, certain embodiments of the present invention can effectively reduce this number to as few as one amplification primers. According to certain embodiments of the present invention, as few as two "universal" primers, can be used to amplify one or more ligation or amplification products, since the probes may be designed to share primer-specific portions but comprise different addressable portions. A sample containing 100 possible biallelic loci would require 200 primers in certain conventional detection methods, yet only one universal primer can be used in certain embodiments of the present invention.

Also, if one were to use certain conventional methods employing labeled probes, a different labeled probe for each different allele at each different locus would be used. According to certain embodiments of the present invention, one can employ two labeled probes to detect the sequence of one or more different loci. For example, in certain conventional methods, one would use 200 different labeled probes to detect the 200 possible sequences at 100 biallelic loci. Using certain embodiments of the present invention, one can use 2 labeled probes to detect 200 possible sequences at 100 biallelic loci.

Also, in certain embodiments one may prescreen a sample for the presence or absence of certain sequences. For example, in certain embodiments, one may employ different ligation probes sets to detect nucleotides at different loci, but each ligation probe set includes probes with the same addressable portion. If no threshold difference in detectable signal value is detected, one concludes that the sample is negative for all of the sequences in question. If there is a threshold difference in detectable signal value during or after an amplification reaction, one concludes that at least one of the sequences in question is present. In certain such embodiments, one could further screen the sample to determine which specific sequence(s) are present.

E. Certain Exemplary Applications

According to certain embodiments, the present invention may be used to detect the presence or absence of (or to quantitate) splice variants in a target nucleic acid sequence. For example, genes, the DNA that encodes for a protein or proteins, may contain a series of coding regions, referred to as exons, interspersed by non-coding regions referred to as introns. In a splicing process, introns are removed and exons are juxtaposed so that the final RNA molecule, typically a messenger RNA (mRNA), comprises a continuous coding sequence. While some genes encode a single protein or polypeptide, other genes can code for a multitude of proteins or polypeptides due to alternate splicing.

For example, a gene may comprise five exons each separated from the other exons by at least one intron, see FIG. 10. The hypothetical gene that encodes the primary transcript, shown at the top of FIG. 10, codes for three different proteins, each encoded by one of the three mature mRNAs, shown at the bottom of FIG. 10. Due to alternate splicing, exon 1 may be juxtaposed with (a) exon 2a-exon 3, (b) exon 2b-exon 3, or (c) exon 2c-exon 3, the three splicing options depicted in FIG. 10, which result in the three different versions of mature mRNA.

The rat muscle protein, troponin T is but one example of alternate splicing. The gene encoding troponin T comprises five exons (W, X, α, β, and Z), each encoding a domain of the final protein. The five exons are separated by introns. Two different proteins, an α-form and a β-form are produced by alternate splicing of the troponin T gene. The α-form is translated from a mRNA that contains exons W, X, α, and Z. The β-form is translated from a mRNA that contains exons W, X, β, and Z.

Certain exemplary embodiments involving splice variants follow. In this application, the use of the terms "first exon" and "second exon" are not limited to the actual first exon and the actual second exon of a given nucleic acid sequence, unless such terms are explicitly used in that manner. Rather, those terms are used to differentiate between any adjoining exons. Thus, one may want to distinguish between two different splice variants of Sequence A, one of which comprises Exons 2 and 3 of Sequence A and one of which comprises Exons 2 and 5 of Sequence A. In the embodiments discussed herein, Exon 2 of Sequence A would be the "first exon" and Exons 3 and 5 of Sequence A would be two "second exons."

In certain embodiments, a method is provided for detecting the presence or absence of (or quantitating) at least one splice variant of at least one given nucleic acid sequence in a sample, wherein the at least one splice variant comprises a sequence that corresponds to a juncture between a first exon and one of a plurality of second exons. In certain embodiments, the method comprises forming a ligation reaction composition comprising the sample and a ligation probe set for each given nucleic acid sequence. In certain embodiments, the ligation probe set for each given nucleic acid sequence comprises: (1) a first probe that comprises (a) a target-specific portion that is complementary to a portion of the given nucleic acid sequence that corresponds to a portion of the first exon and (b) a 5' primer-specific portion, and (2) at least one a second probe that comprises: (a) a splice-specific portion that is complementary to a portion of the given nucleic acid sequence that corresponds to a portion of one of the plurality of second exons; (b) a 3' primer-specific portion; and (c) an addressable portion located between the splice-specific portion and the 3' primer-specific portion, wherein the addressable portion is specific for the one of the plurality of second exons.

If the sample comprises a sequence corresponding to the juncture of the first exon and the one of the plurality of second exons, the first probe and the second probe, which comprises the splice-specific portion that is complementary to the portion of the given nucleic acid sequence that corresponds to the portion of the one of the plurality of second exons, hybridize to the given nucleic acid sequence adjacent to one another so that they are suitable for ligation together.

In certain embodiments, one forms a test composition by subjecting the ligation reaction composition to at least one cycle of ligation, wherein adjacently hybridized probes are ligated together to form a ligation product comprising the 5' primer-specific portion, the target-specific portion, the splice-specific portion, the addressable portion, and the 3' primer-specific portion.

In certain embodiments, one forms an amplification reaction composition comprising: (1) the test composition; (2) a polymerase; (3) at least one labeled probe that (a) comprises the sequence of the addressable portion that is specific for the one of the plurality of second exons, or (b) comprises a sequence that is complementary to the sequence of the addressable portion that is specific for the one of the plurality of second exons, wherein the at least one labeled probe has a first detectable signal value when it is not hybridized to a complementary sequence; and (4) a primer set comprising at least one first primer comprising the sequence of the 5' primer-specific portion of the ligation product and at least one second primer comprising a sequence complementary to the sequence of the 3' primer-specific portion of the ligation product.

In certain embodiments, one subjects the amplification reaction composition to an amplification reaction. In certain embodiments, one detects a second detectable signal value from the at least one labeled probe at least one of during and after the amplification reaction. In certain embodiments, a threshold difference between the first detectable signal value from the at least one labeled probe and the second detectable signal value from the at least one labeled probe indicates the presence of the at least one splice variant of the at least one given target nucleic acid sequence. In such embodiments, no threshold difference between the first detectable signal value from the at least one labeled probe and the second detectable signal value from the at least one labeled probe indicates the absence of the at least one splice variant of the at least one given target nucleic acid sequence.

In certain embodiments, one may desire to detect the presence or absence of (or to quantitate) more than one splice variant of a given nucleic acid sequence. In certain such embodiments, one may employ multiple second probes each comprising a different splice-specific sequence and a different addressable portion for each different second exon sought to be detected or quantitated. In such embodiments, one may employ different labeled probes that each comprise the sequence of one of the different addressable portions, or comprise a sequence that is complementary to the sequence of one of the different addressable portions. In certain such embodiments, each of the different labeled probes may also comprise a different signal moiety that each provide a detectably different signal. If two different labeled probes have a detectable signal value of zero, one would not be able to detect different signals at that value. When a signal value is greater than zero, however, one would be able to detect different signals from the two different labeled probes comprising different signal moieties.

In certain embodiments, the quantity of the at least one splice variant in the at least one target nucleic acid sequence is determined.

In certain embodiments, a method is provided for detecting the presence or absence of (or quantitating) at least one splice variant of at least one given nucleic acid sequence in a sample comprising forming a ligation reaction composition comprising the sample and a ligation probe set for each given nucleic acid sequence. In certain embodiments, the ligation probe set for each given nucleic acid sequence comprises: (1) at least one first probe that comprises: (a) a 5' primer-specific portion, (b) a splice-specific portion that is complementary to a portion of the given nucleic acid sequence that corresponds to a portion of one of the plurality of second exons, and (c) an addressable portion located between the splice-specific portion and the 5' primer-specific portion; and (2) a second probe that comprises: (a) a target-specific portion that is complementary to a portion of the given nucleic acid sequence that corresponds to the first exon and (b) a 5' primer-specific portion.

If the target nucleic acid comprises a sequence corresponding to the juncture of the first and second exon, the first and second probe of the probe set hybridize to the given nucleic acid sequence adjacent to one another so that they are suitable for ligation together.

In certain embodiments, one forms a test composition by subjecting the ligation reaction composition to at least one cycle of ligation, wherein adjacently hybridized probes are ligated together to form a ligation product comprising the 5' primer-specific portion, the addressable portion, the splice-specific portion, the target-specific portion, and the 3' primer-specific portion.

In certain embodiments, one forms an amplification reaction composition comprising: (1) the test composition; (2) a polymerase; (3) at least one labeled probe that (a) comprises the sequence of the addressable portion that is specific for the one of the plurality of second exons, or (b) comprises a sequence that is complementary to the sequence of the addressable portion that is specific for the one of the plurality of second exons, wherein the labeled probe has a first detectable signal value when it is not hybridized to a complementary sequence; and (4) a primer set comprising at least one first primer comprising the sequence of the 5' primer-specific portion of the ligation product and at least one second primer comprising a sequence complementary to the sequence of the 3' primer-specific portion of the ligation product.

In certain embodiments, one subjects the amplification reaction composition to an amplification reaction. In certain embodiments, one detects a second detectable signal value from the at least one labeled probe at least one of during and after the amplification reaction. In certain embodiments, a threshold difference between the first detectable signal value from the at least one labeled probe and the second detectable signal value from the at least one labeled probe indicates the presence of the at least one splice variant of the at least one given target nucleic acid sequence. In such embodiments, no threshold difference between the first detectable signal value from the at least one labeled probe and the second detectable signal value from the at least one labeled probe indicates the absence of the at least one splice variant of the at least one given target nucleic acid sequence.

In certain embodiments, one may desire to detect the presence or absence of (or to quantitate) more than one splice variant of a given nucleic acid sequence. In certain such embodiments, one may employ multiple first probes each comprising a different splice-specific sequence and a different addressable portion for each different second exon sought to be detected or quantitated. In such embodiments, one may employ different labeled probes that each comprise the sequence of one of the different addressable portions, or comprise a sequence that is complementary to the sequence of one of the different addressable portions. In certain such embodiments, each of the different labeled probes may also comprise a different signal moiety that each provide a detectably different signal. If two different labeled probes have a detectable signal value of zero, one would not be able to detect different signals at that value. When a signal value is greater than zero, however, one would be able to detect different signals from the two different labeled probes comprising different signal moieties.

In certain embodiments, the quantity of the at least one splice variant in the at least one target nucleic acid sequence is determined.

In certain embodiments, the at least one target nucleic acid sequence comprises at least one complementary DNA (cDNA) generated from an RNA. In certain embodiments, the at least one cDNA is generated from at least one messenger RNA (mRNA). In certain embodiments, the at least one target nucleic acid sequence comprises at least one RNA target sequence present in the sample.

In various embodiments for detecting the presence or absence of (or quantitating) splice variants, one can use any of the various embodiments employing addressable portions disclosed in this application. In various embodiments, either the first probe or the second probe or both may comprise splice specific portions for detecting the presence or absence of (or to quantitate) different splice variants. Also, in certain embodiments, if one desires to identify and quantify but one splice variant, they can use only one probe that comprises a splice-specific portion (specific to that one splice variant).

Certain nonlimiting embodiments for identifying splice variants are illustrated by FIG. 11. With such embodiments, one detects the presence or absence of (or quantitates) two different splice variants. One splice variant includes exon 1, exon 2, and exon 4. The other splice variant includes exon 1, exon 3, and exon 4.

In the depicted embodiments, one employs a ligation probe set that comprises a first probe (Probe EX1) that comprises a 5' primer-specific portion (PSPa) and a target-specific portion that corresponds to at least a portion of exon 1 (TSP). The probe set further comprises two different second probes (Probe EX2 and Probe EX3). Probe EX2 comprises a 3' primer-specific portion PSPb, an addressable portion ASP1, and a splice-specific portion (SSP-EX2) that corresponds to at least a portion of exon 2. Probe EX3 comprises a 3' primer-specific portion PSPb, an addressable portion ASP2, and a splice-specific portion (SSP-EX3) that corresponds to at least a portion of exon 3.

In the embodiments depicted in FIG. 11, if a splice variant is present, the first and second probes corresponding to that splice variant hybridize adjacent to one another and are ligated together to form a ligation product. In the embodiments depicted in FIG. 11, two labeled probes are employed. One labeled probe (LBP1) comprises the sequence of addressable portion (ASP1) and fluorescent moiety (F1). The other labeled probe (LBP2) comprises the sequence of addressable portion (ASP2) and fluorescent moiety (F2). In the embodiments depicted in FIG. 11, the complements of the ligation products are generated using primers (Pb).

If the complement of a particular ligation product corresponding to a particular splice variant is present, the labeled probe corresponding to that splice variant will hybridize to the corresponding complement of the addressable portion for that splice variant. The labeled probes that are hybridized to such complements of the ligation products will be cleaved during extension with primer (Pa), which results in a threshold difference in detectable signal value.

Thus, in FIG. 11, both labeled probes (LBP1) and (LBP2) hybridize to complementary addressable portions (ASP1') and (ASP2'), respectively, and are cleaved during extension with primer (Pa). Fluorescent moieties F1 and F2 are no longer quenched and one may detect a threshold difference in signal value for both labeled probes LBP1 and LBP2. With such results, one concludes that the sample comprises both splice variants.

In certain embodiments, when the gene expression levels for several target nucleic acid sequences for a sample are known, a gene expression profile for that sample can be compiled and compared with other samples. For example, but without limitation, samples may be obtained from two aliquots of cells from the same cell population, wherein one aliquot was grown in the presence of a chemical compound or drug and the other aliquot was not. By comparing the gene expression profiles for cells grown in the presence of drug with those grown in the absence of drug, one may be able to determine the drug effect on the expression of particular target genes.

In certain embodiments, one may quantitate the amount of mRNA encoding a particular protein within a cell to determine a particular condition of an individual. For example, the protein insulin, among other things, regulates the level of blood glucose. The amount of insulin that is produced in an individual can determine whether that individual is healthy or not. Insulin deficiency results in diabetes, a potentially fatal disease. Diabetic individuals typically have low levels of insulin mRNA and thus will produce low levels of insulin, while healthy individuals typically have higher levels of insulin mRNA and produce normal levels of insulin.

Another human disease typically due to abnormally low gene expression is Tay-Sachs disease. Children with Tay-Sachs disease lack, or are deficient in, a protein(s) required for sphingolipid breakdown. These children, therefore, have abnormally high levels of sphingolipids causing nervous system disorders that may result in death.

In certain embodiments, it is useful to identify and detect additional genetic-based diseases/disorders that are caused by gene over- or under-expression. Additionally, cancer and certain other known diseases or disorders may be detected by, or are related to, the over- or under-expression of certain genes. For example, men with prostate cancer typically produce abnormally high levels of prostate specific antigen (PSA); and proteins from tumor suppressor genes are believed to play critical roles in the development of many types of cancer.

Using nucleic acid technology, in certain embodiments, minute amounts of a biological sample can typically provide sufficient material to simultaneously test for many different diseases, disorders, and predispositions. Additionally, there are numerous other situations where it would be desirable to quantify the amount of specific target nucleic acids, in certain instances mRNA, in a cell or organism, a process sometimes referred to as "gene expression profiling." When the quantity of a particular target nucleic acid within, for example, a specific cell-type or tissue, or an individual is known, in certain cases one may start to compile a gene expression profile for that cell-type, tissue, or individual. Comparing an individual's gene expression profile with known expression profiles may allow the diagnosis of certain diseases or disorders in certain cases. Predispositions or the susceptibility to developing certain diseases or disorders in the future may also be identified by evaluating gene expression profiles in certain cases. Gene expression profile analysis may also be useful for, among other things, genetic counseling and forensic testing in certain cases.

F. Certain Exemplary Kits

In certain embodiments, the invention also provides kits designed to expedite performing certain methods. In certain embodiments, kits serve to expedite the performance of the methods of interest by assembling two or more components used in carrying out the methods. In certain embodiments, kits may contain components in pre-measured unit amounts to minimize the need for measurements by end-users. In certain embodiments, kits may include instructions for performing one or more methods of the invention. In certain embodiments, the kit components are optimized to operate in conjunction with one another.

In certain embodiments, a kit for detecting at least one target nucleic acid sequence in a sample is provided. In certain embodiments, a kit comprises: a ligation probe set for each target sequence, the probe set comprising (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence. The probes in each set are suitable for ligation together when hybridized adjacent to one another on a complementary target sequence. One probe in each probe set further comprises an addressable portion located between the primer-specific portion and the target-specific portion, wherein the addressable portion comprises a sequence. In certain embodiments, the kit further comprises a labeled probe comprising the sequence of the addressable portion or comprising a sequence complementary to the sequence of the addressable portion.

In certain embodiments, the kit comprises a labeled probe that has a first detectable signal value when it is not hybridized to a complementary sequence and a second detectable signal value of the labeled probe can be detected at least one of during and after an amplification reaction. In certain embodiments, a threshold difference between the first detectable signal value and the second detectable signal value indicates the presence of the target nucleic acid sequence, and no threshold difference between the first detectable signal value and the second detectable signal value indicates the absence of the target nucleic acid sequence.

In certain embodiments, a kit for detecting at least one target nucleic acid sequence in a sample is provided. In certain embodiments, a kit comprises: a ligation probe set for each target sequence, the probe set comprising:

(a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence; and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence.

The probes in each set are suitable for ligation together when hybridized adjacent to one another on a complementary target sequence.

In certain embodiments, the kit further comprises:

a first labeled probe comprising the addressable sequence of the first addressable portion or comprising a sequence complementary to the sequence of the first addressable portion; and a second labeled probe comprising the sequence of the second addressable portion or comprising a sequence complementary to the sequence of the second addressable portion.

In certain embodiments, the kit comprises:

a first labeled probe that has a first detectable signal value when it is not hybridized to a complementary sequence, and a second detectable signal value of the first labeled probe can be detected at least one of during and after an amplification reaction; and a second labeled probe that has a first detectable signal value when it is not hybridized to a complementary sequence, and a second detectable signal value of the second labeled probe can be detected at least one of during and after an amplification reaction.

In certain embodiments, a threshold difference between the first detectable signal value and the second detectable signal value of the first labeled probe and a threshold difference between the first detectable signal value and the second detectable signal value of the second labeled probe indicates the presence of the target nucleic acid sequence; and no threshold difference between the first detectable signal value and the second detectable signal value of the first labeled probe and no threshold difference between the first detectable signal value and the second detectable signal value of the second labeled probe indicates the absence of the target nucleic acid sequence.

In certain embodiments, kits further comprise primers. In certain embodiments, kits further comprise at least one primer set comprising (i) at least one first primer comprising the sequence of the 5' primer-specific portion of the at least one first probe, and (ii) at least one second primer comprising a sequence complementary to the sequence of the 3' primer-specific portion of the at least one second probe.

In certain embodiments, kits comprise one or more additional components, including, without limitation, at least one of: at least one polymerase, at least one transcriptase, at least one ligation agent, oligonucleotide triphosphates, nucleotide analogs, reaction buffers, salts, ions, and stabilizers. In certain embodiments, kits comprise one or more reagents for purifying the ligation products, including, without limitation, at least one of dialysis membranes, chromatographic compounds, supports, and oligonucleotides.

The following examples are intended for illustration purposes only, and should not be construed as limiting the scope of the invention in any way.

EXAMPLE 1

The following Table 1 is referred to throughout the following Example 1:

TABLE 1

| Probe Set For Assay 1 | | |
|---|---|---|
| First Probe-CYC (1) | 5' TTGCCTGCTCGACTTAGAT*CAAAGGAGACGCGG*CTGCTTTCAGCCTCAT3' | (SEQ ID NO:1) |
| First Probe-RNA (1) | 5' TTGCCTGCTCGACTTAGAG*GGTCACAGTAGGTGG*TGCTTTCAGCCTCAC3' | (SEQ ID NO:2) |
| Second Probe (1) | 5' P-*GGGGATAGTGGCTGC*ATCACTGGATAGCGACGT3' | (SEQ ID NO:3) |
| Probe Set For Assay 2 | | |
| First Probe-CYC (2) | 5' TTGCCTGCTCGACTTAGAT*CAAAGGAGACGCGG*CAGTGGTTTTCCAACG3' | (SEQ ID NO:4) |
| First Probe-RNA (2) | 5' TTGCCTGCTCGACTTAGAG*GGTCACAGTAGGTGG*ACAGTGGTTTTCCAACA3' | (SEQ ID NO:5) |
| Second Probe (2) | 5' P-*TGAACACACCGGGT*ATCACTGGATAGCGACGT3' | (SEQ ID NO:6) |
| PCR Primers | | |
| Forward Primer | 5' TTGCCTGCTCGACTTAGA3' | (SEQ ID NO:7) |
| Reverse Primer | 5' ACGTCGCTATCCAGTGAT3' | (SEQ ID NO:8) |
| TaqMan ® Probe Sequences | | |
| CYCLOPHILIN: | 5' CCGCGTCTCCTTTGA3'-MGBNFQ (labeled with VIC) | (SEQ ID NO:9) |
| RNASE P: | 5' CCACCTACTGTGACCC-MGBNFQ (labeled with FAM) | (SEQ ID NO:10) |

(MGB = minor groove binder and NFQ = nonfluorescent quencher, which are both included on Taq-Man ® probes available from Applied Biosystems, Foster City, CA)

A. Ligation Probes

In these examples, a ligation probe set for each target nucleic acid sequence comprised first and second ligation probes designed to adjacently hybridize to the appropriate target nucleic acid sequence. These adjacently hybridized probes were, under appropriate conditions, ligated to form a ligation product.

This illustrative embodiment used two different ligation probe sets for detecting two biallelic loci. Three different samples of genomic DNA were tested. Table 1 shows the two probe sets that were used. Table 1 also shows the two Taqman® probes that were used in these examples. The ligation probes included a target-specific portion, shown in italic letters in Table 1. As shown by bold letters in Table 1, the ligation probes also included universal primer-specific portion sequences (18 nucleotides at the 5' end of the first listed probes in each probe set and 18 nucleotides at the 3' end of the second listed probe in each probe set). As shown by underlined letters in Table 1, the first two probes in each ligation probe set also included the same two different addressable portions that are complementary to the different sequences of the two TaqMan® probes.

The ligation probes were synthesized using conventional automated DNA synthesis chemistry.

B. Exemplary Ligation Reactions (Oligonucleotide Ligation Assay "OLA")

Ligation reactions were performed in separate reaction volumes with each of the two different ligation probe sets shown in Table 1. The concentrations of the component materials prior to forming the ligation reaction composition are shown below in Table 2.

TABLE 2

| Component Materials | Concentration |
| --- | --- |
| Thermus aquaticus (Taq) DNA Ligase | 40 units/µL |
| 10X OLA Buffer 2 Mixture: pH 7.5 @ 50° C. | |
| Sodium (3-[N-Morpholino]propanesulfonate) (MOPS) | 200 mM |
| Triton X-100 | 1% (w/v) |
| Dithiothreitol (DTT) | 10 mM |
| Magnesium Chloride | 70 mM |
| β-Nicotinamide Adenine Dinucleotide (NAD) | 2.5 mM |
| poly (dIC) | 300 ng/µL |
| Genomic DNA (DNase 1 digested) | 100 ng/µL |
| OLA Probe Set: | |
| First probe - CYC | 5 nM |
| First probe - RNA | 5 nM |
| Second probe | 10 nM |
| Nuclease Free Water | |

Taq Ligase was diluted to 2.0 units/µL in the 1×OLA Buffer 2 Mixture. The volume of Taq Ligase was sufficient to form the following stock of OLA reagent. The common working stock of OLA reagent was formed as specified in the following Table 3. The following volumes of components are based on a single 10 µL OLA reaction volume. Depending on the number of OLA reactions that are desired, one can form the particular volume of stock OLA reagent.

TABLE 3

| OLA Reaction Component | 1X OLA Reaction Volume (µL) | X number of OLA Reactions = Total Volume (µL) |
| --- | --- | --- |
| 10X OLA Buffer 2 Mixture | 1.0 | |
| Nuclease Free Water | 5.4 | |
| Taq DNA Ligase (2.0 units/µL) | 0.6 | |

For each reaction with one of the two probe sets of Table 1, 7 µL of the stock OLA reaction composition of Table 3 was combined with 2.0 µL of the given probe set using the OLA probe set concentrations in Table 2, and 1.0 µL genomic DNA using the genomic DNA concentration in Table 2. The final assay component concentrations for the OLA reactions are set forth in Table 4 below.

TABLE 4

| OLA Component | Concentration |
| --- | --- |
| Thermus aquaticus (Taq) DNA Ligase | 0.12 units/µL |
| Sodium (3-[N-Morpholino]propanesulfonate) (MOPS) | 20 mM |

TABLE 4-continued

| OLA Component | Concentration |
| --- | --- |
| Triton X-100 | 0.1% (w/v) |
| Dithiothreitol (DTT) | 1 mM |
| Magnesium Chloride | 7 mM |
| β-Nicotinamide Adenine Dinucleotide (NAD) | 0.25 mM |
| poly (dIC) | 30 ng/µL |
| Genomic DNA (DNase 1 digested) | 10 ng/µL |
| OLA Probe Set: | |
| First probe - CYC | 1 nM |
| First probe - RNA | 1 nM |
| Second probe | 2 nM |

For these examples, each of the two different probe sets in Table 1 were included in different reactions for three different genomic DNA samples. Thus, there were six different reactions volumes, each with a different combination of probe set and genomic DNA sample. The three genomic DNA samples were obtained from Coriell Cell Repositories (Camden, N.J.) and were designated as follows: NA17103, NA17212, and NA17247. Prior to combining each of the genomic DNA samples in the ligation reaction composition, the genomic DNA was fragmented by DNase I digestion.

The ligation reaction volumes were subjected to the reaction conditions shown in Table 5 below using an ABI 9700 Thermal Cycler (Applied Biosystems, Foster City, Calif.). The reaction volumes were kept on ice until they were transferred to the thermal cycler. The OLA reaction tubes were transferred from ice to the thermal cycler when the thermal cycler reached the first hold temperature of 90° C.

TABLE 5

| Step | Step Type | Temperature (° C.) | Time |
| --- | --- | --- | --- |
| 1 | Hold | 90 | 3 minutes |
| 2 | 14 cycles | 90 | 5 seconds |
| | | 54 | 4 minutes |
| 3 | Hold | 99 | 10 minutes |
| 4 | Hold | 4 | ∞ |

C. Exemplary Amplification Reactions

A 10× primer/labeled probe composition was formed by combining the forward and reverse primers of Table 1 and the two TaqMan® probes labeled with VIC and FAM so that they were in final concentrations as follows:

| Forward Primer | 9 µM |
| --- | --- |
| Reverse Primer | 9 µM |
| TaqMan® [VIC] | 2 µM |
| TaqMan® [FAM] | 2 µM. |

Each PCR reaction volume included the following components:

12.5 µL—2× TaqMan® Universal PCR Mix (Applied Biosystems, Foster City, Calif.). The PCR Mix includes PCR buffer, dNTPs, $MgCl_2$, uracil-N-glucosidase, and AmpliTaq Gold® DNA polymerase (Applied Biosystems, Foster City, Calif.);

2.5 µL—10× primer/labeled probe composition discussed above;

8 µL—water; and

2 μL—OLA reaction volume after the ligation reaction from Example 1B above.

Thus, the total PCR reaction volume for each PCR reaction was 25 μL. Each PCR reaction volume was subjected to the reaction conditions shown in Table 6 below using an ABI 7700 Thermal Cycler (Applied Biosystems, Foster City, Calif.).

TABLE 6

| Step | Step Type | Temperature (° C.) | Time |
|------|-----------|--------------------|------|
| 1 | Hold | 50 | 2 minutes |
| 2 | Hold | 95 | 10 minutes |
| 3 | 40 cycles | 92 | 15 seconds |
|   |           | 60 | 1 minute |

In Assay 1, the signal from the TaqMan® probe labeled with FAM indicated that the genomic DNA NA17103 was homozygous for the allele corresponding to the First Probe-RNA (1), which has a "C" as the nucleotide at the pivotal complement. Thus, the genomic DNA NA17103 correctly was determined to be homozygous at the locus analyzed in Assay 1 with "G" at the pivotal nucleotide.

In Assay 1, the signal from the TaqMan® probe labeled with VIC indicated that the genomic DNA NA17212 was homozygous for the allele corresponding to the First Probe-CYC (1), which has a "T" as the nucleotide at the pivotal complement. Thus, the genomic DNA NA17212 correctly was determined to be homozygous at the locus analyzed in Assay 1 with "A" at the pivotal nucleotide.

In Assay 1, the signals from the TaqMan® probes labeled with FAM and VIC indicated that the genomic DNA NA17247 was heterozygous for the alleles corresponding to both the First Probe-CYC (1) and the First Probe-RNA (1). Thus, the genomic DNA NA17247 correctly was determined to be heterozygous at the locus analyzed in Assay 1 with "G" and "A" at the pivotal nucleotides.

In Assay 2, the signal from the TaqMan® probe labeled with FAM indicated that the genomic DNA NA17103 was homozygous for the allele corresponding to the First Probe-RNA (2), which has an "A" as the nucleotide at the pivotal complement. Thus, the genomic DNA NA17103 correctly was determined to be homozygous at the locus analyzed in Assay 2 with "T" at the pivotal nucleotide.

In Assay 2, the signals from the TaqMan® probes labeled with FAM and VIC indicated that the genomic DNA NA17212 was heterozygous for the alleles corresponding to both the First Probe-CYC (2) and the First Probe-RNA (2). Thus, the genomic DNA NA17212 correctly was determined to be heterozygous at the locus analyzed in Assay 2 with "T" and "C" at the pivotal nucleotides.

In Assay 2, the signal from the TaqMan® probe labeled with VIC indicated that the genomic DNA NA17247 was homozygous for the allele corresponding to the First Probe-CYC (2), which has a "G" as the nucleotide at the pivotal complement. Thus, the genomic DNA NA17247 correctly was determined to be homozygous at the locus analyzed in Assay 2 with "C" at the pivotal nucleotide.

Other assays that employed the same concentrations of materials and same thermal cycling conditions as assays 1 and 2, but that employed different probe sets to detect the presence or absence of two alleles at different loci, were also performed. Some of those assays resulted in false negative signal. It was concluded that the second probes of those probe sets were defective, which inhibited appropriate ligation.

EXAMPLE 2

The following Table 7 is referred to throughout the following Example 2:

TABLE 7

Probe Set For Assay 3

First Probe-CYC (3)
5' TTGCCTGCTCGACTTAGATCCGCGTCTCCTTTGATTTGTACCACTCTTTTT*CGGTCAAAAACGAGATCAA*3'  (SEQ ID NO:11)

First Probe-RNA (3)
5' TTGCCTGCTCGACTTAGATCCACCTACTGTGACCCTTTGTACCACTCTTTTT*CGGTCAAAAACGAGATCAG*3'  (SEQ ID NO:12)

Second Probe (3)
5' P-*TACCAGCTTAACACATAGC*ATCACTGGATAGCGACGT3'  (SEQ ID NO:13)

Probe Set For Assay 4

First Probe-CYC (4)
5' TTGCCTGCTCGACTTAGATCCGCGTCTCCTTTGATTTGTACCACTCTTTTT*CAATAACTAAAGGTACAACAT*3'  (SEQ ID NO:14)

First Probe-RNA (4)
5' TTGCCTGCTCGACTTAGATCCACCTACTGTGACCCTTTGTACCACTCTTTTT*CAATAACTAAAGGTACAACAC*3'  (SEQ ID NO:15)

Second Probe (4)
5' P-*GGCATAATAATCTCCAAAG*ATCACTGGATAGCGACGT3'  (SEQ ID NO:16)

Probe Set For Assay 5

First Probe-CYC (5)
5' TTGCCTGCTCGACTTAGATCCGCGTCTCCTTTGATTTGTACCACTCTTTTT*CAGTGGTTTTCCAACG*3'  (SEQ ID NO:17)

First Probe-RNA (5)
5' TTGCCTGCTCGACTTAGATCCACCTACTGTGACCCTTTGTACCACTCTTTTT*CACAGTGGTTTTCCAACA*3'  (SEQ ID NO:18)

Second Probe (5)
5' P-*TGAACACACCGGGT*ATCACTGGATAGCGACGT3'  (SEQ ID NO:19)

TABLE 7-continued

PCR Primers

Forward Primer
5' TTGCCTGCTCGACTTAGA3' (SEQ ID NO:20)

TaqMan ® Probe Sequences

CYCLOPHILIN:
5' CCGCGTCTCCTTTGA3'-MGBNFQ (labeled with VIC) (SEQ ID NO:22)

RNASE P:
5' CCACCTACTGTGACCC-MGBNFQ (labeled with FAM) (SEQ ID NO:23)

(MGB = minor groove binder and NFQ = nonfluorescent quencher, which are both included on Taq-Man ® probes available from Applied Biosystems, Foster City, CA)

A. Ligation Probes

In these examples, a ligation probe set for each target nucleic acid sequence comprised first and second ligation probes designed to adjacently hybridize to the appropriate target nucleic acid sequence. These adjacently hybridized probes were, under appropriate conditions, ligated to form a ligation product.

This illustrative embodiment used three different ligation probe sets for detecting three biallelic loci. Three different samples of genomic DNA were tested. Table 7 shows the three probe sets that were used. Table 7 also shows the two Taqman® probes that were used in these examples. The ligation probes included a target-specific portion, shown in italic letters in Table 7. As shown by bold letters in Table 7, the ligation probes also included universal primer-specific portion sequences (18 nucleotides at the 5' end of the first listed probes in each probe set and 18 nucleotides at the 3' end of the second listed probe in each probe set). As shown by underlined letters in Table 7, the first two probes in each ligation probe set also included the same two different addressable portions that have the same sequences as the two different sequences of the two TaqMan® probes.

The ligation probes were synthesized using conventional automated DNA synthesis chemistry.

B. Exemplary Ligation Reactions (Oligonucleotide Ligation Assay "OLA") and Amplification Reactions Each of the three different ligation probe sets shown in Table 7 were used in separate reaction volumes. In each reaction volume both ligation and amplification reactions were performed. For this example, each of the three different probe sets in Table 7 were included in different reactions for three different genomic DNA samples. Thus, there were nine different reaction volumes, each with a different probe set and a different genomic DNA sample. Also, one set of such reactions included dithiothreitol (DDT) and another set did not include DDT. Thus, there were 18 different reaction volumes. The reactions were replicated.

The three genomic DNA samples were obtained from Coriell Cell Repositories (Camden, N.J.) and were designated as follows: NA17103, NA17212, and NA17247. Prior to combining each of the genomic DNA samples in the ligation reaction composition, the genomic DNA was fragmented as follows. The genomic DNA was diluted in 1×TE (10 mM Tris, pH 8, 1 mM Sodium EDTA, Sigma Pt. No. T-9285) solution to a concentration of approximately 300 ng/μl. The diluted genomic DNA solution was dispensed into PCR tubes, at a volume of 150 μl per tube.

The tubes of diluted genomic DNA solution were then incubated at 4° C. for 1 minute, 99° C. for 15 minutes, then held at 4° C. for an indefinite period until the fragmented genomic DNA was needed. Samples of genomic DNA that were divided into multiple tubes were then pooled into one tube again.

The stock concentrations and final concentrations of the component materials for each of the reactions are shown below in Table 8. The reaction volumes were 25 μl.

TABLE 8

All of the components other than the primer/labeled probe composition and gDNA were included in the master mix, and the primer/labeled probe composition and gDNA were added later.

| WITH DTT | | 1× | | | 20× |
|---|---|---|---|---|---|
| component | stock concentration | μl | actual $C_f$ | desired $C_f$ | μl |
| Taq ligase | 4 units/μl | 0.75 | 0.12 units/μl | 0.12 units/μl | 15 |
| OLA Probe Set | | 1 | | | |
| First Probe-CYC | 25 nM | NA | 1 nM | 1 nM | NA |
| First Probe-RNA | 25 nM | | 1 nM | 1 nM | |
| Second Probe | 50 nM | | 2 nM | 2 nM | |
| TaqMan Universal Mix | 2× | 12.5 | 1× | 1× | 250 |
| primer/labeled probe | 10× | 2.5 | 1× | 1× | 50 |
| Forward primer | 9 μM | NA | 0.9 μM | 0.9 μM | NA |
| Reverse primer | 9 μM | | 0.9 μM | 0.9 μM | |
| TaqMan [VIC] probe | 2 μM | | 0.2 μM | 0.2 μM | |
| TaqMan [FAM] probe | 2 μM | | 0.2 μM | 0.2 μM | |
| DTT | 100 mM | 0.25 | 1 mM | 1 mM | 5 |
| NAD | 2.5 mM | 2.5 | 0.25 mM | 0.25 mM | 50 |
| water | | 4.2 | | | 84 |

TABLE 8-continued

All of the components other than the primer/labeled probe composition
and gDNA were included in the master mix, and the primer/labeled
probe composition and gDNA were added later.

| gDNA | use 100 ng gDNA | 1.3 | | | NA |
|---|---|---|---|---|---|
| TOTAL | | 25 | | | 454 |

| WITHOUT DTT | | 1× | | | 20× |
|---|---|---|---|---|---|
| component | stock concentration | µl | actual $C_f$ | desired $C_f$: | µl |
| Taq ligase | 4 units/µl | 0.75 | 0.12 units/µl | 0.12 units/µl | 15 |
| OLA Probe Set | | 1 | | | NA |
| First Probe-CYC | 25 nM | NA | 1 nM | 1 nM | NA |
| First Probe-RNA | 25 nM | | 1 nM | 1 nM | |
| Second Probe | 50 nM | | 2 nM | 2 nM | |
| TaqMan Universal Mix | 2× | 12.5 | 1× | 1× | 250 |
| primer/labeled probe | 10× | 2.5 | 1× | 1× | 50 |
| Forward primer | 9 µM | NA | 0.9 µM | 0.9 µM | NA |
| Reverse primer | 9 µM | | 0.9 µM | 0.9 µM | |
| TaqMan [VIC] probe | 2 µM | | 0.2 µM | 0.2 µM | |
| TaqMan [FAM] probe | 2 µM | | 0.2 µM | 0.2 µM | |
| NAD | 2.5 mM | 2.5 | 0.25 mM | 0.25 mM | 50 |
| water | | 4.45 | | | 89 |
| gDNA | use 100 ng gDNA | 1.3 | | | NA |
| TOTAL | | 25 | | | 454 |

VIC probe is the Cyclophilin TaqMan ® Probe
FAM probe is the RNASE P TaqMan ® Probe
NAD is nicotinamide adenine dinucleotide
This application claims the benefit under 35 U.S.C. § 119(e) of prior U.S. Provisional Patent Application No. 60/412,189, filed Sep. 19, 2002, which is incorporated herein by reference. TaqMan ® Universal Mix is the 2× TaqMan ® Universal PCR Mix (Applied Biosystems, Foster City, CA). The PCR Mix includes PCR buffer, dNTPs, $MgCl_2$, uracil-N-glucosidase, and AmpliTaq Gold ® DNA polymerase (Applied Biosystems, Foster City, CA)

Each reaction volume was subjected to the following thermal cycling conditions set forth in Table 9 below.

TABLE 9

Thermal cycling conditions:

| Step | Step Type | Temperature | Time |
|---|---|---|---|
| 1 | Hold | 50 | 2 minutes |
| 2 | Hold | 90 | 3 minutes |
| 3 | 14 cycles | 90 | 5 seconds |
| | | 54 | 4 minutes |
| 4 | Hold | 95 | 10 minutes |
| 5 | 40 cycles | 92 | 15 seconds |
| | | 60 | 1 minute |

In Assay 3, the signal from the TaqMan® probe labeled with VIC indicated that the genomic DNA NA17103 was homozygous for the allele corresponding to the First Probe-CYC (3), which has an "A" as the nucleotide at the pivotal complement. Thus, the genomic DNA NA17103 correctly was determined to be homozygous at the locus analyzed in Assay 3 with "T" at the pivotal nucleotide.

In Assay 3, the signals from the TaqMan® probes labeled with FAM and VIC indicated that the genomic DNA NA17212 was heterozygous for the alleles corresponding to both the First Probe-CYC (3) and the First Probe-RNA (3). Thus, the genomic DNA NA17212 correctly was determined to be heterozygous at the locus analyzed in Assay 3 with "T" and "C" at the pivotal nucleotides.

In Assay 3, the signal from the TaqMan® probe labeled with FAM indicated that the genomic DNA NA17247 was homozygous for the allele corresponding to the First Probe-RNA (3), which has a "G" as the nucleotide at the pivotal complement. Thus, the genomic DNA NA17247 correctly was determined to be homozygous at the locus analyzed in Assay 2 with "C" at the pivotal nucleotide.

In Assay 4, the signal from the TaqMan® probe labeled with VIC indicated that the genomic DNA NA17103 was homozygous for the allele corresponding to the First Probe-CYC (4), which has a "T" as the nucleotide at the pivotal complement. Thus, the genomic DNA NA17103 correctly was determined to be homozygous at the locus analyzed in Assay 4 with "A" at the pivotal nucleotide.

In Assay 4, the signal from the TaqMan® probe labeled with FAM indicated that the genomic DNA NA17212 was homozygous for the allele corresponding to the First Probe-RNA (4), which has a "C" as the nucleotide at the pivotal complement. Thus, the genomic DNA NA17212 correctly was determined to be homozygous at the locus analyzed in Assay 4 with "G" at the pivotal nucleotide.

In Assay 4, the signals from the TaqMan® probes labeled with FAM and VIC indicated that the genomic DNA NA17247 was heterozygous for the alleles corresponding to both the First Probe-CYC (4) and the First Probe-RNA (4). Thus, the genomic DNA NA17247 correctly was determined to be heterozygous at the locus analyzed in Assay 4 with "A" and "G" at the pivotal nucleotides.

In Assay 5, the signal from the TaqMan® probe labeled with FAM indicated that the genomic DNA NA17103 was homozygous for the allele corresponding to the First Probe-RNA (5), which has an "A" as the nucleotide at the pivotal complement. Thus, the genomic DNA NA17103 correctly was determined to be homozygous at the locus analyzed in Assay 5 with "T" at the pivotal nucleotide.

In Assay 5, the signals from the TaqMan® probes labeled with FAM and VIC indicated that the genomic DNA NA17212 was heterozygous for the alleles corresponding to both the First Probe-CYC (5) and the First Probe-RNA (5). Thus, the genomic DNA NA17212 correctly was determined to be heterozygous at the locus analyzed in Assay 2 with "C" and "T" at the pivotal nucleotides.

In Assay 5, the signal from the TaqMan® probe labeled with VIC indicated that the genomic DNA NA17247 was homozygous for the allele corresponding to the First Probe-CYC (5), which has a "G" as the nucleotide at the pivotal complement. Thus, the genomic DNA NA17247 correctly was determined to be homozygous at the locus analyzed in Assay 5 with "C" at the pivotal nucleotide.

For the most part, the three assays correctly identified the presence or absence of the appropriate alleles at the three different loci of the three genomic DNA samples being analyzed with the three probe sets. The data for the replicates were not always as tight as may be desired according to certain embodiments.

Other assays that employed the same concentrations of materials and same thermal cycling conditions as assays 3 to 5, but that employed different probe sets to detect the presence or absence of two alleles at different loci, were also performed. Some of those assays included problems with the controls and at least one other had an erroneous result most likely due to a manual pipetting error.

Although the invention has been described with reference to certain applications, methods, and compositions, it will be appreciated that various changes and modifications may be made without departing from the invention.

What is claimed is:

1. A method for detecting at least one target nucleic acid sequence in a sample comprising: forming a ligation reaction composition comprising the sample and a ligation probe set for each target nucleic acid sequence, the probe set comprising (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence, and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence, wherein the probes in each set are suitable for ligation together when hybridized adjacent to one another on a complementary target nucleic acid sequence; forming a test composition by subjecting the ligation reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion; forming an amplification reaction composition comprising: the test composition; a polymerase; a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion; a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product; subjecting the amplification reaction composition to at least one amplification reaction; and detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence; and wherein no threshold difference between the first detectable signal value and the second detectable signal value of the first labeled probe and no threshold difference between the first detectable signal value and the second detectable signal value of the second labeled probe indicates the absence of the target nucleic acid sequence.

2. The method of claim 1, wherein the labeled probe is a 5' nuclease probe.

3. The method of claim 2, wherein the 5' nuclease probe comprises at least one signal moiety and at least one quencher moiety.

4. The method of claim 3, wherein the least one signal moiety comprises at least one fluorescent moiety.

5. The method of claim 2, wherein the 5' nuclease probe comprises at least one signal moiety and at least one donor moiety.

6. The method of claim 1, wherein the labeled probe is a hybridization dependent probe.

7. The method of claim 6, wherein the hybridization dependent probe comprises at least one signal moiety and at least one quencher moiety.

8. The method of claim 7, wherein the least one signal moiety comprises at least one fluorescent moiety.

9. The method of claim 6, wherein the hybridization dependent probe comprises at least one signal moiety and at least one donor moiety.

10. The method of claim 1, wherein the labeled probe is a cleavable RNA probe.

11. The method of claim 10, wherein the cleavable RNA probe comprises at least one signal moiety and at least one quencher moiety.

12. The method of claim 11, wherein the least one signal moiety comprises at least one fluorescent moiety.

13. The method of claim 10, wherein the cleavable RNA probe comprises at least one signal moiety and at least one donor moiety.

14. The method of claim 1, wherein the at least one second probe further comprises a flap portion and a FEN cleavage position nucleotide, such that the target-specific portion of the at least one second probe is located between the FEN cleavage position nucleotide and the 3' primer-specific portion, and such that the FEN cleavage position nucleotide is located between the flap portion and the target-specific portion of the at least one second probe.

15. The method of claim 14, wherein the target-specific portion of the at least one first probe comprises a pivotal complement on an end of target-specific portion, such that the remainder of the target-specific portion is located between the 5' primer-specific portion and the pivotal complement, and wherein the FEN cleavage position nucleotide of the at least one second probe is the same as the pivotal complement of the at least one first probe.

16. The method of claim 15, wherein the ligation reaction composition further comprises flap endonuclease.

17. The method of claim 14, wherein the target-specific portion of the at least one first probe comprises (a) a pivotal complement that is at a penultimate position to an end of the target-specific portion and (b) a given nucleotide at that end of the target-specific portion, such that the remainder of the target-specific portion is located between the 5' primer-specific portion and the pivotal complement, and wherein the FEN cleavage position nucleotide of the at least one second probe is the same as the given nucleotide of the at least one first probe.

18. The method of claim 17, wherein the ligation reaction composition further comprises flap endonuclease.

19. The method of claim 14, wherein the target-specific portion of the at least one second probe comprises a pivotal complement at an end of the target-specific portion that is adjacent the FEN cleavage position nucleotide, and wherein the target-specific portion of the at least one first probe comprises a given nucleotide at an end of the target-specific portion, such that the remainder of the target-specific portion is located between the 5' primer-specific portion and the given nucleotide, and wherein the FEN cleavage position nucleotide of the at least one second probe is the same as the given nucleotide of the at least one first probe.

20. The method of claim 19, wherein the ligation reaction composition further comprises flap endonuclease.

21. A method for detecting at least one target nucleic acid sequence in a sample comprising: forming a ligation reaction composition comprising the sample and a ligation probe set for each target nucleic acid sequence, the probe set comprising (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence; wherein the probes in each set are suitable for ligation together when hybridized adjacent to one another on a complementary target nucleic acid sequence; wherein at least one of said at least one first probe and said at least one second probe further comprises (a) a first addressable portion located between the primer-specific portion and the target-specific portion, wherein the first addressable portion comprises a sequence, and (b) a second addressable portion located between the primer-specific portion and the target-specific portion, wherein the second addressable portion comprises a sequence; forming a test composition by subjecting the ligation reaction composition to at least one cycle of ligation, wherein adjacently hybridizing complementary probes are ligated to one another to form a ligation product comprising the 5' primer-specific portion, the first addressable portion, the second addressable portion, the target-specific portions, and the 3' primer-specific portion; forming an amplification reaction composition comprising: the test composition; a polymerase; a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion; a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product; subjecting the amplification reaction composition to at least one amplification reaction; and detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence; and wherein no threshold difference between the first detectable signal value and the second detectable signal value of the first labeled probe and no threshold difference between the first detectable signal value and the second detectable signal value of the second labeled probe indicates the absence of the target nucleic acid sequence.

22. A method for detecting at least one target nucleic acid sequence in a sample comprising: (a) forming a reaction composition comprising: the sample; a ligation probe set for each target nucleic acid sequence, the probe set comprising: (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence, and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence; wherein the probes in each set are suitable for ligation together when hybridized adjacent to one another on a complementary target nucleic acid sequence; a polymerase; a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion; a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product; (b) subjecting the reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion; (c) after the at least one cycle of ligation, subjecting the reaction composition to at least one amplification reaction; and (d) detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence; and wherein no threshold difference between the first detectable signal value and the second detectable signal value of the first labeled probe and no threshold difference between the first detectable signal value and the second detectable signal value of the second labeled probe indicates the absence of the target nucleic acid sequence.

23. A method for detecting at least one target nucleic acid sequence in a sample comprising: (a) forming a reaction composition comprising: the sample; a ligation probe set for each target nucleic acid sequence, the probe set comprising (a) at least one first probe, comprising a target-specific portion and a 5' primer-specific portion, wherein the 5' primer-specific portion comprises a sequence, and (b) at least one second probe, comprising a target-specific portion and a 3' primer-specific portion, wherein the 3' primer-specific portion comprises a sequence; wherein the probes in each set are suitable for ligation together when hybridized adjacent to one another on a complementary target nucleic acid sequence; wherein at least one of said at least one first probe and said at least one second probe further comprises (a) a first addressable portion located between the primer-specific portion and the target-specific portion, wherein the first addressable portion comprises a sequence, and (b) a second addressable portion located between the primer-specific portion and the target-specific portion, wherein the second addressable portion comprises a sequence; a polymerase; a first labeled probe, wherein the first labeled probe has a first detectable signal value when it is not hybridized to a complementary sequence, and wherein the first labeled probe comprises the sequence of the first addressable portion or comprises a sequence complementary to the sequence of the first addressable portion; a second labeled probe, wherein the second labeled probe has a first detectable signal value when it is not hybridized to a complementary sequence, and wherein the second labeled probe comprises the sequence of the second addressable portion or comprises a sequence complementary to the sequence of the second addressable portion; and at least one primer set, the primer set comprising (i) at least one first primer comprising the sequence of the 5' primer-specific portion of the ligation product, and (ii) at least one second primer comprising a sequence complementary to the sequence of the 3' primer-specific portion of the ligation product; (b) subjecting the reaction composition to at least one cycle of ligation, wherein adjacently hybridizing complementary probes are ligated to one another to form a ligation product comprising the 5' primer-specific portion, the first addressable portion, the target-specific portions, the second addressable portion, and the 3' primer-specific portion; (c) after the at least one cycle of ligation, subjecting the reaction composition to at least one amplification reaction; and (d) detecting a second detectable signal value from the first labeled probe and from the second labeled probe at least one of during and after the amplification reaction, wherein a threshold difference between the first detectable signal value and the second detectable signal value of the first labeled probe and a threshold difference between the first detectable signal value and the second detectable signal value of the second labeled probe indicates the presence of the target nucleic acid sequence; and wherein no threshold difference between the first detectable signal value and the second detectable signal value of the first labeled probe and no threshold difference between the first detectable signal value and the second detectable signal value of the second labeled probe indicates the absence of the target nucleic acid sequence.

24. A kit for detecting at least one target nucleic acid sequence in a sample comprising: a ligation probe set for each target nucleic acid sequence, the probe set comprising (a) at least one first probe, comprising a target-specific portion, a 5' primer-specific portion, wherein the 5' primer-specific portion comprises a sequence, and a first addressable portion located between the 5' primer-specific portion and the target-specific portion, wherein the first addressable portion comprises a sequence, and (b) at least one second probe, comprising a target-specific portion, a 3' primer-specific portion, wherein the 3' primer-specific portion comprises a sequence, and a second addressable portion located between the 3' primer-specific portion and the target-specific portion, wherein the second addressable portion comprises a sequence, wherein the probes in each set are suitable for ligation together when hybridized adjacent to one another on a complementary target nucleic acid sequence; a first labeled probe comprising the addressable sequence of the first addressable portion or comprising a sequence complementary to the sequence of the first addressable portion; and a second labeled probe comprising the sequence of the second addressable portion or comprising a sequence complementary to the sequence of the second addressable portion.

25. The kit of claim 24, wherein the first labeled probe has a first detectable signal value when it is not hybridized to a complementary sequence, and a second detectable signal value of the first labeled probe can be detected at least one of during and after an amplification reaction; and wherein the second labeled probe has a first detectable signal value when it is not hybridized to a complementary sequence, and a second detectable signal value of the second labeled probe can be detected at least one of during and after an amplification reaction; and wherein a threshold difference between the first detectable signal value and the second detectable signal value of the first labeled probe and a threshold difference between the first detectable signal value and the second detectable signal value of the second labeled probe indicates the presence of the target nucleic acid sequence; and wherein no threshold difference between the first detectable signal value and the second detectable signal value of the first labeled probe and no threshold difference between the first detectable signal value and the second detectable signal value of the second labeled probe indicates the absence of the target nucleic acid sequence.

26. The kit of claim 24, further comprising at least one primer set comprising (i) at least one first primer comprising the sequence of the 5' primer-specific portion of the at least one first probe, and (ii) at least one second primer comprising a sequence complementary to the sequence of the 3' primer-specific portion of the at least one second probe.

* * * * *